US009200297B2

(12) United States Patent
Chen et al.

(10) Patent No.: US 9,200,297 B2
(45) Date of Patent: Dec. 1, 2015

(54) ACIDOGENIC CLOSTRIDIA AND PROCESSES OF USING THEREOF FOR PRODUCING VOLATILE FATTY ACIDS

(71) Applicant: GREEN CELLULOSITY CORPORATION, Hsinchu (TW)

(72) Inventors: Chang-Chieh Chen, Taipei (TW); Yi-Te Chou, Taipei (TW); Shao-Wen Wu, Nantou County (TW); Shi-Chan Tseng, Tainan (TW); Hsin-Tzu Kuo, Kaohsiung (TW); Wan-Ting Ma, New Taipei (TW)

(73) Assignee: GREEN CELLULOSITY CORPORATION, Hsinchu (TW)

( * ) Notice: Subject to any disclaimer, the term of this patent is extended or adjusted under 35 U.S.C. 154(b) by 0 days.

(21) Appl. No.: 14/044,453

(22) Filed: Oct. 2, 2013

(65) Prior Publication Data

US 2014/0120591 A1    May 1, 2014

Related U.S. Application Data

(60) Provisional application No. 61/709,294, filed on Oct. 3, 2012.

(51) Int. Cl.
| | |
|---|---|
| *C12P 7/56* | (2006.01) |
| *C12P 7/40* | (2006.01) |
| *C12P 7/54* | (2006.01) |
| *C12P 7/52* | (2006.01) |
| *C12N 1/20* | (2006.01) |
| *C12R 1/145* | (2006.01) |

(52) U.S. Cl.
CPC ... *C12P 7/54* (2013.01); *C12P 7/40* (2013.01); *C12P 7/52* (2013.01); *C12R 1/145* (2013.01)

(58) Field of Classification Search
CPC .............. C12P 7/54; C12P 1/145; C12P 7/52; C12P 7/40
USPC ........................ 435/139, 136, 140, 141, 252.7
See application file for complete search history.

(56) References Cited

U.S. PATENT DOCUMENTS

| 5,173,429 A | 12/1992 | Gaddy et al. |
| 7,704,723 B2 | 4/2010 | Huhnke et al. |
| 8,143,037 B2 | 3/2012 | Zahn et al. |
| 8,178,329 B2 | 5/2012 | Kohn et al. |
| 2007/0275447 A1 | 11/2007 | Lewis et al. |
| 2011/0008860 A1 | 1/2011 | Reeves et al. |
| 2011/0229947 A1 | 9/2011 | Zahn et al. |
| 2011/0238941 A1 | 9/2011 | Xu et al. |
| 2012/0064587 A1 | 3/2012 | Papoutsakis et al. |
| 2012/0156747 A1 | 6/2012 | Zahn et al. |
| 2012/0309075 A1 | 12/2012 | Simpson et al. |
| 2013/0109066 A1 | 5/2013 | Simpson |

OTHER PUBLICATIONS

Clostridium tyrobutyricum Gene Locus GI: 144904 dated Apr. 26, 1993; 3 pages down-loaded from http://www.ncbi.nlm.nih.gov/ on Apr. 22, 2015.*
Henstra, A.M. et al., "Microbiology of Synthesis Gas Fermentation for Biofuel Production", Current Opinion in Biotechnology, vol. 18, pp. 200-206 (2007).
Köpke, M., et al., "Clostridium Ljungdahlil Represents a Microbial Production Platform Based on Syngas", PNAS, vol. 107, pp. 13087-13092 (Jul. 20, 2010).
Munasinghe, P.R., et al., "Biomass-Derived Syngas Fermentation Into Biofuels: Opportunities and Challenges", Bioresource Technology 101, pp. 5013-5022 (2010).
Köpke, M., at al., "2,3-Butanediol Production by Acetogenic Bacteria, an Alternative Route to Chemical Synthesis, Using Industrial Waste Gas", Applied and Environmental Microbiology, vol. 77, No, 15, pp. 5467-5475 (Aug. 2011).
Wilkins, M. R., et al., "Microbial Production of Ethanol from Carbon Monoxide", Current Opinion in Biotechnology 22, po. 326-330 (2011).
Abubackar. H,N., et al., Biological Conversion of Carbon Monoxide to Ethanol: Effect of pH, Gas Pressure, Reducing, Agent and Yeast Extract, Bioresource Technology 114, pp. 518-522 (2012).
Drake, H.L., et al., "Old Acetogens, New Light", Annals of the New York Academy of Sciences 1125, pp. 100-128 (2006).
Guo, Y., at al., "Medium Optimization for Ethanol Production with Clostridium Autoethanogenum with Carbon Monoxide as Sole Carbon Source", Bioresource Technology 101, pp. 8784-8789 (2010).
Kundiyana, D.K., et al., "Effect of Temperature, pH and Buffer Presence on Ethanol Production from Synthesis Gas by 'Clostridium Ragsdale'", Bioresource Technology 102, pp. 5794-5799 (2011).
Kundiyana, D.K. at al., "Effect of Nutrient Limitation and Two-stage Continuous Fermentor Design on Productivities during 'Clostridium Ragsdale' Syngas Fermentation", Bioresource Technology 102, pp. 6058-6064 (2011).
Liou, J. S.C., et al., "*Clostridium carboxidivorans* sp. nov., A Solvent-Producing Clostridium Isolated From an Agricultural Settling Lagoon, and Reclassification of the Acetogen Clostridium Scatologenes Strain SL1 as *Clostridium drakei* sp. Nov.", International Journal of Systematic and Evolutionary Microbiology 55, pp. 2085-2091 (2005).
Tanner, R.S, et al., "*Clostridium ljungdahlii* Sp. Nov., An Acetogenic Species in Clostridial rRNA Homology Group I", International Journal of Systematic Bacteriolgy, vol. 43, No. 2, pp. 232-236 (Apr. 1993).

* cited by examiner

*Primary Examiner* — Ganapathirama Raghu
(74) *Attorney, Agent, or Firm* — Ping Wang; Andrews Kurth LLP

(57) ABSTRACT

An isolated biologically pure culture of *Clostridium tyrobutyricum* ITRI04001 or an isolated biologically pure culture of *Clostridium tyrobutyricum* having the genotypic characteristics of ITRI04001 useful for syngas fermentation. Volatile free acids are produced by a method comprising culturing a microorganism having the genotypic characteristics of ITRI04001 in a medium; providing at least one substrate comprising at least one carbon source chosen from CO and $CO_2$ to the microorganism; and recovering at least one free volatile free acid. Syngas can be the at least one substrate in these processes for producing volatile free acids.

17 Claims, 10 Drawing Sheets

Figure 7

Figure 1:
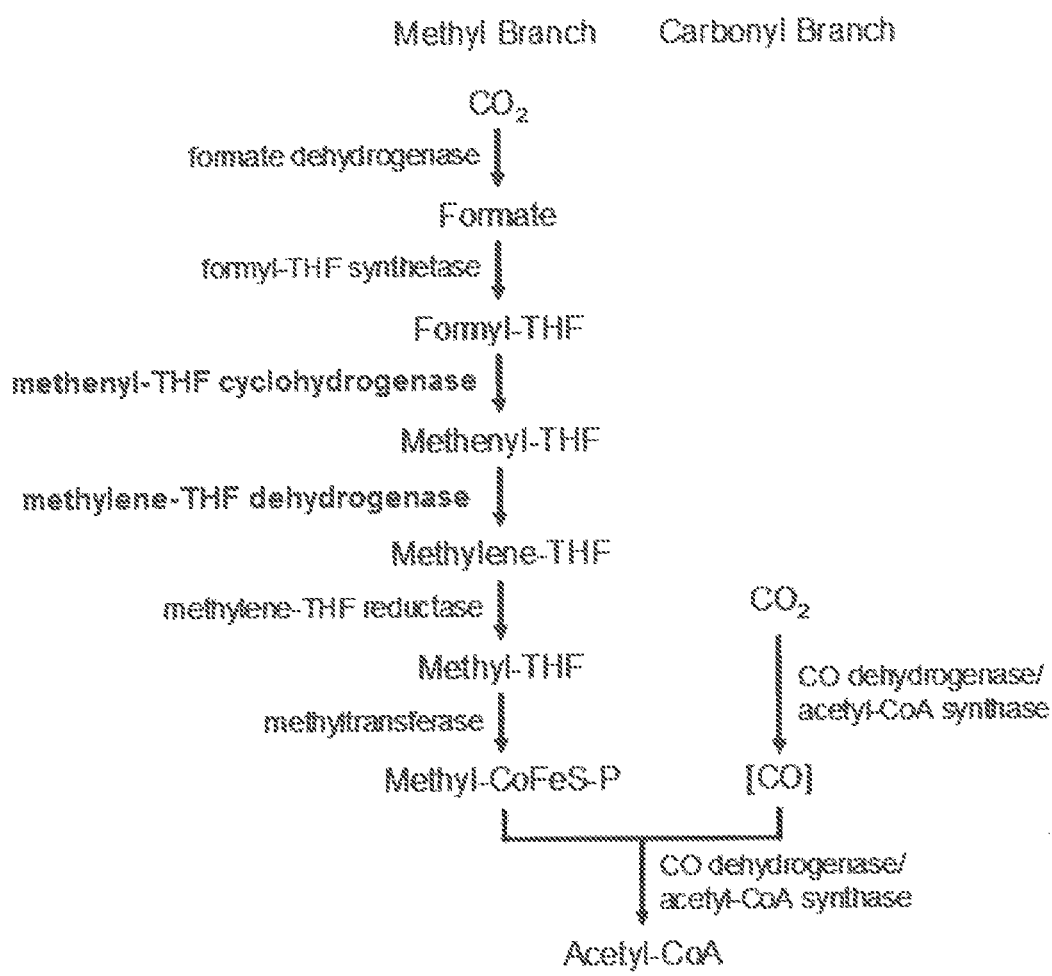

```
Identities = 251/272 (92%), Gaps = 0/272 (0%)

ATCC 25755   22   ATGGGAACAATGCATTAAGAAATATGAACGTCAATTCAATAATCATCAAAGCCATG   81
                  |||||  |||||||||||||||||||||| |||||||   ||||||||||||||||
ITRI 04001        ATGGCAAACAATGCATTAAGAAATATAACATCAATTCAGGAAATGCATCAAAGCCAATG

ATCC 25755   82   GAAAAACTTTCTTGNGTTCTTAGAATAAACAGAGCTGAGCGGATGCGCAGCACTAGCA   141
                  |||||||||||||||||||||||||||||||||||||||| || |||||||||  |||
ITRI 04001        GAAAAACTTTCTTGCGGTCTTAGAATAAACGGAGCTGAGATGCGCAGCACGATTACCA

ATCC 25755   142  ATATCAGAAAAATGAGAGGACAGATAAATGTTTGAATCAGGCATCAAGTAATCCACAG   201
                  ||||||||||||||||||||||||||||||||||  ||  |||||||||||  ||||
ITRI 04001        ATATCAGAAAAATGAGAGGACAGATAAATGATTAAACCAGGCATCAAGCAACTCACAG

ATCC 25755   202  GATTCAATATCACTTATACAGACTGCTGAAGGTGCATTAAAGGAAGCTCACACCATACTT   261
                  ||| | ||||| ||||||||||||||||||||| |||||||||||||||||| |||||
ITRI 04001        GATGCTATAGCCTTATACAGACTGTTGAAGGTGCATTAATGAAACTCACAGTATACTT

ATCC 25755   262  CAGAGAATGAGAACACTTGCTGTTCAATCATC   293
                  ||||||||||||||||||| |||||||||||
ITRI 04001        CAGAGAATGAGAACGCTTGCAGTTCAATCATC

Identities = 148/162 (91%), Gaps = 0/162 (0%)

ATCC 25755   958  AATAGATTGAACATACAATAAATAACTTAGGAACTTCATCAGAAACTTGACTTCTTCT   1017
                  |||||||||||||||| ||||| | ||||||||||||||||| ||||||||||||||
ITRI 04001        AATAGATTGAACATACTATAAACAATCTTGGAACTTCATCAGAAATTTGACTTCTTCT

ATCC 25755   1018 GAATCAAGAATAAGAGATGTTGATATGGCATCAGAAATCTCTGAGTACTCAAAGAATAAC   1077
                  ||||||||||| ||||||| ||||||  ||||||||||||  |||| |||||||||  |
ITRI 04001        GAATCAAGAATCAGAGATCGGATATGGCATCAGAGATCTCTGAGTACTCAAAGAACAAT

ATCC 25755   1078 ATTCTTTCTCAGACTGCTCAGGCAATGCTTGCACAAGCAAAT   1119
                  |||||||||||||| |||||  ||||  ||||| ||||||||
ITRI 04001        ATTCTTTCTCAGGCTGCTCAGGAAATGCTGCACAAGCAAAT
```

ACIDOGENIC CLOSTRIDIA AND PROCESSES OF USING THEREOF FOR PRODUCING VOLATILE FATTY ACIDS

This application claims priority to U.S. Provisional Application No. 61/709,294, filed on Oct. 3, 2012.

SEQUENCE LISTING

The instant application contains a Sequence Listing which has been submitted electronically in ASCII format and is hereby incorporated by reference in its entirety. Said ASCII copy, created on Dec. 23, 2013, is named 06720.0370_SL.txt and is 58,791 bytes in size.

Synthesis gas ("syngas") is a fuel gas mixture comprising primarily carbon monoxide (CO), carbon dioxide ($CO_2$), and hydrogen ($H_2$). Syngas can be produced by steam reforming of natural gas or gasification of various organic materials such as biomass, organic waste, coal, petroleum, plastics, or other carbon containing materials.

Catalytic processes have been developed to convert syngas into a variety of fuels and chemicals such as methane, methanol, formaldehyde, acetic acid and ethanol. Microorganisms have also been used to convert syngas into fuels and chemicals. For instance, syngas has been converted into liquid fuel and chemicals by acetogenic Clostridia microorganisms such as *Clostridium autoethanogenum*, *Clostridium ljungdahlii*, *Clostridium carboxidivorans*, and *Clostridium ragsdalei*.

Anaerobic bacteria, such as those from the genus *Clostridium*, produce ethanol from CO, $CO_2$, and $H_2$ via the acetyl-CoA biochemical pathway (also known as the Wood-Ljungdahl pathway) as shown in FIG. 1.

Microbial processes used for converting syngas are generally referred to as syngas fermentation. Compared to chemical catalytic processes, syngas fermentation processes may be conducted at lower temperature and pressure, have higher reaction specificity, and do not require a specific ratio of CO to $H_2$.

There remains, however, an ongoing need to discover and develop additional microorganisms that are capable of producing chemicals or biofuels by syngas fermentation. In particular, it would be advantageous to use bacterial species that may grow on different types of substrates and also provide good yields of products of interest.

One embodiment of the present disclosure is to provide an isolated biologically pure culture of *Clostridium tyrobutyricum* ITRI04001 suitable for converting, for example, syngas or a gas mixture comprising primarily CO and/or $CO_2$ to fuels such as butanol and/or chemicals such as volatile fatty acids (e.g., butyric acid). For instance, in some embodiments, the bacteria disclosed herein may convert CO and/or $CO_2$ to volatile fatty acids such as formic acid, acetic acid, lactic acid, propanoic acid, butyric acid, and mixtures thereof.

Another embodiment of the present disclosure is to provide a process for producing volatile fatty acids such as formic acid, acetic acid, lactic acid, propanoic acid, butyric acid, and mixtures thereof, comprising culturing a microorganism having the genotypic characteristics of ITRI04001 in a medium, providing at least one substrate comprising at least one carbon source chosen from CO and $CO_2$ to the microorganism, and recovering volatile free acid from the culture.

Additional objects and advantages of the present disclosure will be set forth in part in the description which follows, and in part will be obvious from the description, or may be learned by practice of the present disclosure. The objects and advantages of the present disclosure will be realized and attained by means of the elements and combinations particularly pointed out in the appended claims.

It is to be understood that both the foregoing general description and the following detailed description are exemplary and explanatory only, and are not restrictive of the invention as claimed.

The accompanying drawings, which are incorporated in and constitute a part of this specification, illustrate embodiments of the invention and together with the description, serve to explain embodiments of the invention.

BRIEF DESCRIPTION OF THE DRAWINGS

FIG. 1 shows the Wood-Ljungdahl pathway in microorganisms.

FIGS. 2A and 2B show the HPLC spectrum of a liquid sample taken 48 hours after the ITRI04001 was cultivated in CGM medium containing 5 g/L of glucose as described in Example 1.

FIG. 3A shows the concentrations of various products of ITRI04001 in CGM medium containing 5 g/L of glucose after 18 hours of cultivation as described in Example 1.

FIG. 3B shows the concentrations of various products of ITRI04001 in CGM medium containing 5 g/L of glucose and 5 g/L of lactate after 36 hours of cultivation as described in Example 1.

FIG. 4 shows the growth rate of ITRI04001 and ATCC 25755 with different dilution ratios in CGM medium containing 5 g/L of glucose as described in Example 2.

FIG. 5 shows the growth rate of ITRI04001 and ATCC 25755 with different dilution ratios in CGM medium containing 5 g/L of glucose and 5 g/L of lactate.

FIG. 6 shows the butyrate production rate, glucose consumption rate, and lactate consumption rate of both ITRI 04001 and ATCC 25755 as described in Example 2.

FIG. 7 shows sequence comparisons between two segments of the flagellin gene in ITRI04001 (SEQ ID NO:34, top alignment and SEQ ID NO:36, bottom alignment) and ATCC 25755 (SEQ ID NO 33, top alignment and SEQ ID NO:35, bottom alignment) as described in Example 2.

FIG. 8 shows (A) the changes of $OD_{600}$, (B) formate, (C) acetate, (D) propionate, and (E) butyrate in the medium cultivated with ITRI04001 and provided with syngas comprising 10% $H_2$, 20% CO, 20% $CO_2$, and 50% $N_2$ as described in Example 3.

FIG. 9 shows the HPLC spectrum of a liquid sample taken from medium cultivated for 24 hours with ITRI04001 and provided with syngas comprising 10% $H_2$, 20% CO, 20% $CO_2$, and 50% $N_2$ as described in Example 3.

DESCRIPTION OF THE EMBODIMENTS

Below, exemplary embodiments will be described in detail with reference to accompanying drawings so as to be easily understood by a person having ordinary skill in the art. The inventive concept may be embodied in various forms without being limited to the exemplary embodiments.

Reference will now be made in detail to exemplary embodiments of the invention, examples of which are illustrated in the accompanying drawings.

The term "acid" as used here includes both carboxylic acids and the associated carboxylate anion. The ratio of molecular acid to carboxylate in the fermentation broth may dependent upon the pH of the system.

The term "volatile free acids" refers to fatty acids with a carbon chain of six carbons or fewer. For instance, volatile fatty acids include formic acid (formate), acetic acid (acetate), lactic acid (lactate), propanoic acid (propionate), and butyric acid (butyrate).

Anaerobic Bacterial Species

The present disclosure provides an isolated anaerobic bacterial species capable of producing volatile free acids from relatively common substrates. In some embodiments, the disclosed bacteria can produce volatile fatty acids such as formic acid, acetic acid, lactic acid, propanoic acid, butyric acid, and mixtures thereof. In some embodiments, the bacteria disclosed herein may produce salts chosen from formate salts, acetate salts, lactate salts, propionate salts, butyrate salts, and mixtures thereof.

In some embodiments, the disclosed isolated anaerobic bacterial species relate to an acidogenic *Clostridium*, *C. tyrobutyricum* comprising 16S rRNA sequences as set forth in SEQ ID NO:1, or any nucleotide sequence with at least 80%, such as 85%, 90%, 95%, 98%, or 99% identity with SEQ ID NO:1.

In some embodiments, the disclosed isolated anaerobic bacterial species is an isolated biologically pure culture of *Clostridium tyrobutyricum* ITRI04001, deposited at the Deutsche Sammlung von Mikroorganismen and Zellkulturen GmbH with accession number DSM 27751.

In some embodiments, the isolated anaerobic bacteria species is an isolated biologically pure culture of *Clostridium tyrobutyricum* having the genotypic characteristics of ITRI04001.

In some embodiments, the isolated anaerobic bacterial species comprises at least two groups of genetic sequences encoding key enzymes for producing volatile fatty acids from syngas: one coding for acetyl-CoA synthesis from syngas, and another coding for production of volatile fatty acids such as formic acid, acetic acid, lactic acid, propanoic acid, butyric acid, and mixtures thereof. The enzymes of the acetyl-CoA pathway include formate dehydrogenase, formyl-THF synthetase, methenyl-THF cyclohydrogenase, methylene-THF dehydrogenase, methylene-THF reductase, methyltransferase, and CO dehydrogenase/acetyl-CoA synthase.

The genetic sequence encoding for the production of formic acid, acetic acid, lactic acid, propanoic acid, and butyric acid are as follows:

For formic acid or formate synthesis: pfl (SEQ ID NO:11), pflA (SEQ ID NO:12), pflD (SEQ ID NO:13)

For acetic acid or acetate synthesis: pta (SEQ ID NO:14), ack (SEQ ID NO:15), ctf (SEQ ID NO:16)

For lactic acid or lactate synthesis: ldh (SEQ ID NOs 17-19), dldh (SEQ ID NO:20)

For propanoic acid or propionate synthesis: pct (SEQ ID NOs 21, 22)

For butyric acid or butyrate synthesis: thl (SEQ ID NO:23), hbd (SEQ ID NOs 24, 25), crt (SEQ ID NOs 26, 27), bcd (SEQ ID NO:28), ptb (SEQ ID NO:29).

In some embodiments, the isolated biologically pure culture of *Clostridium tyrobutyricum* comprising sequences as set forth in SEQ ID NOs 1 through 30, or at least 80%, such as 85%, 90%, 95%, 98%, or 99% identity with SEQ ID NOs 1 through 30.

The isolated anaerobic bacterial species disclosed here may be cultivated with any culture media, substrates, conditions, and processes generally known in the art for culturing anaerobic bacteria.

For example, the disclosed isolated anaerobic bacterial species can be cultured under anaerobic conditions. "Anaerobic conditions" means the level of oxygen ($O_2$) is below 0.5 parts per million in the gas phase.

Further as an example, ITRI04001 can be cultivated in *Clostridium* Growth Medium (CGM) comprising at least one carbon source chosen from glucose, xylose, fructose, lactate, and acetate.

Processes for Producing Volatile Fatty Acids

The isolated anaerobic bacterial species disclosed here, such as ITRI04001, have the ability under anaerobic conditions to produce volatile fatty acids from substrates comprising, for example, $CO+H_2$, or $H_2+CO_2$, or $CO+H_2+CO_2$. The CO or $CO_2$ may provide the carbon source and the $H_2$ or CO may provide the electron source for the reactions producing volatile fatty acids.

Thus, the present disclosure further provides a process for producing volatile free acid comprising:

culturing a microorganism having the genotypic characteristics of ITRI04001 in a medium;

providing at least one substrate comprising at least one carbon source chosen from CO and $CO_2$ to the microorganism; and recovering at least one free volatile free acid.

In some embodiments, the medium does not comprise glucose, xylose, fructose, lactate, or acetate.

In some embodiments, the medium comprises at least one carbohydrate chosen from glucose, xylose, fructose, lactate, and acetate.

In some embodiments, the at least one substrate further comprises at least one gas chosen from $N_2$ and $H_2$.

In some embodiments, the at least one substrate comprises CO and $H_2$.

In some embodiments, the at least one substrate comprises $CO_2$ and $H_2$.

In some embodiments, the at least one substrate comprises CO, $CO_2$, and $H_2$.

In some embodiments, the at least one substrate is a "waste" gas such as syngas, oil refinery waste gases, steel manufacturing waste gases, autothermal reforming of natural gas, and coal gasification.

In some embodiments, the at least one substrate is syngas.

Syngas may be provided from any known source. In one embodiment, syngas may be sourced from gasification of carbonaceous materials. Gasification involves partial combustion of biomass in a restricted supply of oxygen, and the resultant gas may comprise mainly CO.

In some embodiments, syngas suitable for used in the processes disclosed here comprises CO, $CO_2$, $H_2$, and $N_2$.

In some embodiments, syngas may comprise CO in an amount ranging from 10% to 100%, relative to the total moles of the syngas. For instance, the syngas may comprise from 20% to 90%, from 30% to 80%, or from 40% to 70%, relative to the total moles of the syngas.

Generally, the syngas can be added to the fermentation reaction in a gaseous state. However, the present disclosure is not limited to addition of the substrate in this state. For example, a liquid may be saturated with a syngas and that liquid added to the bioreactor.

In some embodiments, syngas may be supplemented with gas from other sources to alter the concentration of gaseous components (e.g., CO, $CO_2$, and/or $H_2$) provided to the microorganism. For example, syngas may be supplemented with gas with a higher level of CO (e.g., steel mill waste gas is enriched in CO) to enrich the level of CO.

For the growth of the microorganism and CO (or $CO_2$)-to-volatile free acid fermentation to occur, in addition to the syngas, the medium may be supplemented with additional nutrients or ingredients suitable for growing the microorganism. Thus, in addition to the at least one carbon source, the medium used for culturing the microorganism may also comprise vitamins, salts, extracts, and/or minerals sufficient to permit growth of the microorganism.

In some embodiments, the process for producing volatile free acids may be carried out under conditions for the desired fermentation to occur (e.g. CO (or $CO_2$)-to-volatile free acids). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

The processes disclosed herein may be carried out in any suitable bioreactor in which the substrate can be contacted with one or more microorganisms, such as a continuous stirred tank reactor (CSTR), an immobilized cell reactor, a gas-lift reactor, a bubble column reactor (BCR), a membrane reactor such as a Hollow Fiber Membrane Bioreactor (HFMBR) or a trickle bed reactor (TBR), monolith bioreactor, or loop reactors. Also, in some embodiments of the invention, the bioreactor may comprise a first, growth reactor in which the micro-organisms are cultured, and a second, fermentation reactor, to which fermentation broth from the growth reactor is fed and in which most of the fermentation product (e.g. volatile fatty acids) is produced.

In some embodiments, fermentation will be allowed to proceed until a desired level of volatile fatty acids is produced in the culture media. Alternatively, production may be halted when a certain rate of production is achieved, e.g. when the rate of production of a desired product has declined due to, for example, build-up of bacterial waste products, reduction in substrate availability, feedback inhibition by products, reduction in the number of viable bacteria, or for any reasons known to those of skill in the art. In addition, continuous culture techniques are known which allow the continual replenishment of fresh culture medium with concurrent removal of used medium, including any liquid products.

The fermentation will result in fermentation broth comprising volatile free acids, as well as bacterial cells such as ITRI04001.

Free volatile free acid can be removed from the typically aqueous fermentation broth by any known methods such as precipitation, extraction (e.g., organic solvent liquid-liquid extraction), adsorption, dialysis (e.g., electrodialysis), ion exchange, and pressure-driven membrane separation processes. For example, the methods may the ones described in but not limited to Schügerl K., 2000 Biotechnol Adv. 18:581-599; Yang, S.-T. and Lu, C. (2013) Extraction-Fermentation Hybrid (Extractive Fermentation), in Separation and Purification Technologies in Biorefineries, UK. doi: 10.1002/9781118493441.ch15.

For example, precipitation has been widely used for recovering fumaric and lactic acid, which have a low solubility when present in their calcium salt form. As an example, for recovering lactic acid, a conventional fermentation process produces calcium lactate precipitate, which can then be collected and re-acidified.

As another example, the butyric acid present in the fermentation broth may be recovered and purified by extraction using an aliphatic amine, such as Alamine 336 (tri-octyl/decyl amine; Alamine336®, Cognis, Cincinnati, Ohio, USA), or other water-immiscible solvents.

Other embodiments of the invention will be apparent to those skilled in the art from consideration of the specification and practice of the invention disclosed herein. It is intended that the specification and examples be considered as exemplary only, with a true scope and spirit of the invention being indicated by the claims.

Examples

Media

The composition of the Reinforced Clostridial Medium (RCM) and *Clostridium* Growth Medium (CGM) used in the following tables.

| Reinforced Clostridial Medium (RCM) | |
|---|---|
| Beef Extract | 10 g/L |
| Peptone | 10 g/L |
| Sodium Chloride | 5 g/L |
| Dextrose | 5 g/L |
| Yeast Extract | 3 g/L |
| Sodium Acetate | 3 g/L |
| Soluble Starch | 1 g/L |
| L-Cysteine HCl | 0.5 g/L |
| Agar | 0.5 g/L |

Final pH: 6.8 ± 0.2 at 25° C.

| *Clostridium* Growth Medium (CGM) | |
|---|---|
| Yeast extract | 5 g/L |
| Peptone | 5 g/L |
| $(NH_4)_2SO_4$ | 3 g/L |
| $K_2HPO_4$ | 1.5 g/L |
| $MgSO_4 \cdot 7H_2O$ | 0.6 g/L |
| $FeSO_4 \cdot 7H_2O$ | 0.03 g/L |

Final pH: 6.0 ± 0.2 at 25° C.

Example 1

Production of *Clostridium tyrobutyricum* ITRI04001

Raw milk samples from dairy cattle were collected in Taiwan and subsequently heated at 70° C. for 10 min. After cooling to room temperature, the samples were mixed with Reinforced Clostridial Medium (RCM) supplemented with 20% sodium lactate, and then incubated at 37° C. under anaerobic conditions.

To isolate Clostridia bacterial species, PCR-based assays specific for 16S rRNA sequence with a pair of primers (forward: GCGGCGTGCYTAAYACATGC (SEQ ID NO: 31), and reverse: GGGTTGCGCTCGTTGCRGGA (SEQ ID NO: 32)) was used to evaluate the samples. When the expected size of PCR products was detected in the samples, the samples were then diluted serially and spread on *Clostridium* Growth Medium (CGM) agar plates containing 5 g/L glucose and 5 g/L sodium lactate. The resulting plates were incubated at 37° C. anaerobically until colonies appeared. Single colonies were picked up from the CGM agar plates and analyzed by PCR-based assays specific for 16S rRNA sequence with a pair of primers: forward: GCGGCGTGCYTAAYACATGC (SEQ ID NO: 31), and reverse: GGGTTGCGCTCGTTGCRGGA (SEQ ID NO: 32). The PCR products were sequenced and analyzed by Basic Local Alignment Search Tool on NCBI website (NCBI BLASTN, database selected: Nucleotide collection, optimized for megablast).

Characteristic of ITRI04001

The ITRI04001 colonies grown on CGM agar plates appeared to have irregular margins, brownish yellow color, and slightly raised centers.

When observed under the microscope, ITRI04001 appeared motile and exhibited endospores morphology.

Phylogenetic analysis of the 16S rRNA gene sequence (SEQ 1) of ITRI04001 indicated that ITRI04001 belongs to *Clostridium tyrobutyricum*. ITRI04001 and *Clostridium tyrobutyricum* ATCC® 25755 ("ATCC 25755") shared about 99% of sequence similarity with regard to their 16S rRNA genes.

ITRI04001 was cultivated in CGM medium containing 5 g/L of glucose, xylose, fructose, lactate, or acetate at 37° C., under anaerobic conditions. Growth was monitored by measuring optional density (OD) at a wavelength of 600 nm $OD_{600}$). After 72 hours, growth of ITRI04001 was observed in all types of media. Accordingly, ITRI04001 can be cultivated using glucose, xylose, fructose, lactate, or acetate as a carbon source.

ITRI04001 was plated on RCM agar containing various antibiotics with different concentrations and then cultivated for 72 hours at 37° C., under anaerobic conditions. Colonies of ITRI04001 were observed on the surface of the agar plates containing apramycin (25 ug/ml), spectinomycin (250 ug/ml), streptomycin (500 ug/ml), or Kanamycin (25 ug/ml).

Figure 2A:
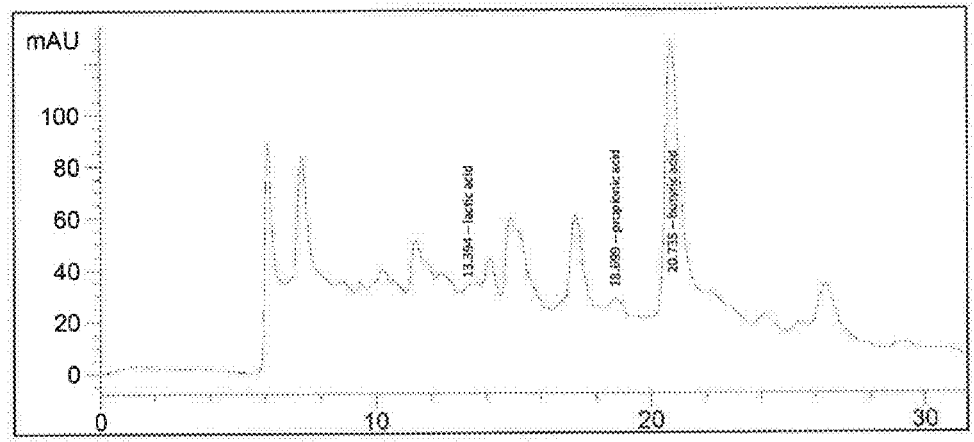
Figure 2B:
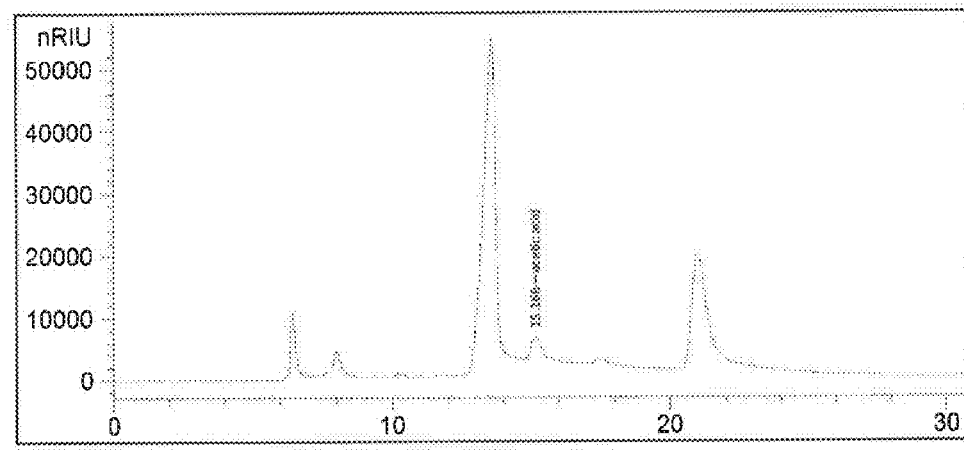

ITRI04001 was cultivated in CGM medium containing 5 g/L of glucose, and liquid samples of the culture were taken every 24 hours and were analyzed with HPLC. FIGS. 2A and 2B shows the HPLC spectrum of a liquid sample taken 48 hours after the ITRI04001 was cultivated in CGM medium containing 5 g/L of glucose. The HPLC spectrum shows that butyrate, acetate, lactate, and propionate were produced.

Figure 3A:
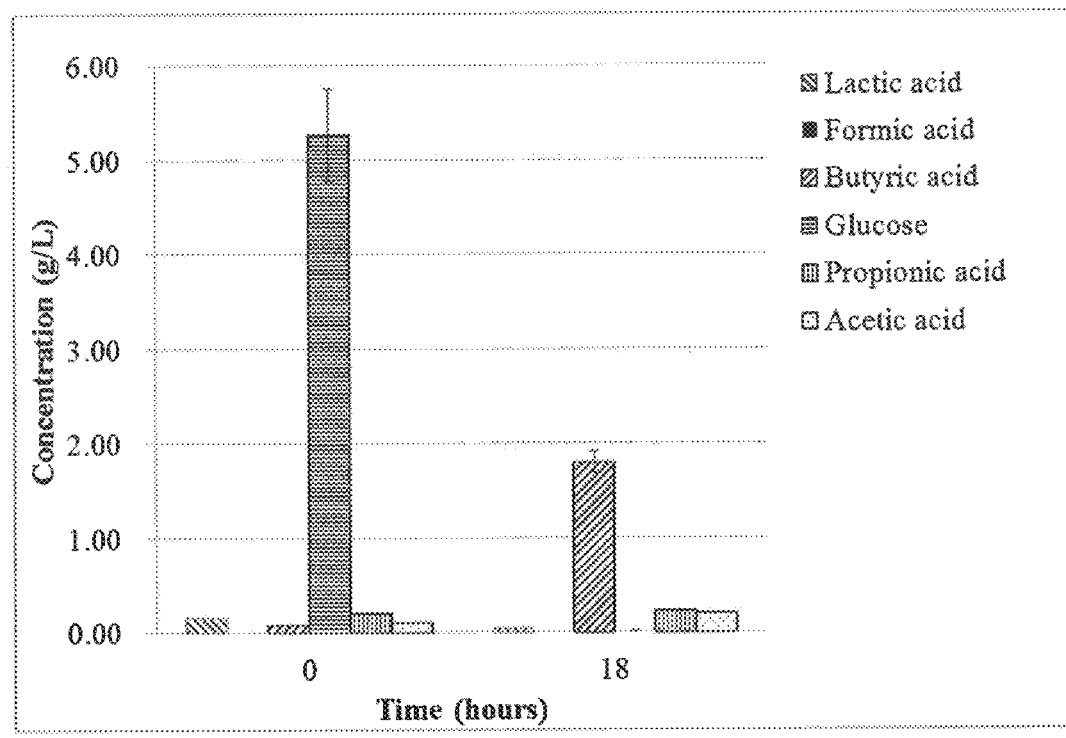

FIG. 3A shows the concentrations of various products of ITRI04001 in CGM medium containing 5 g/L of glucose after 18 hours of cultivation at 37° C., under anaerobic conditions.

Figure 3B:
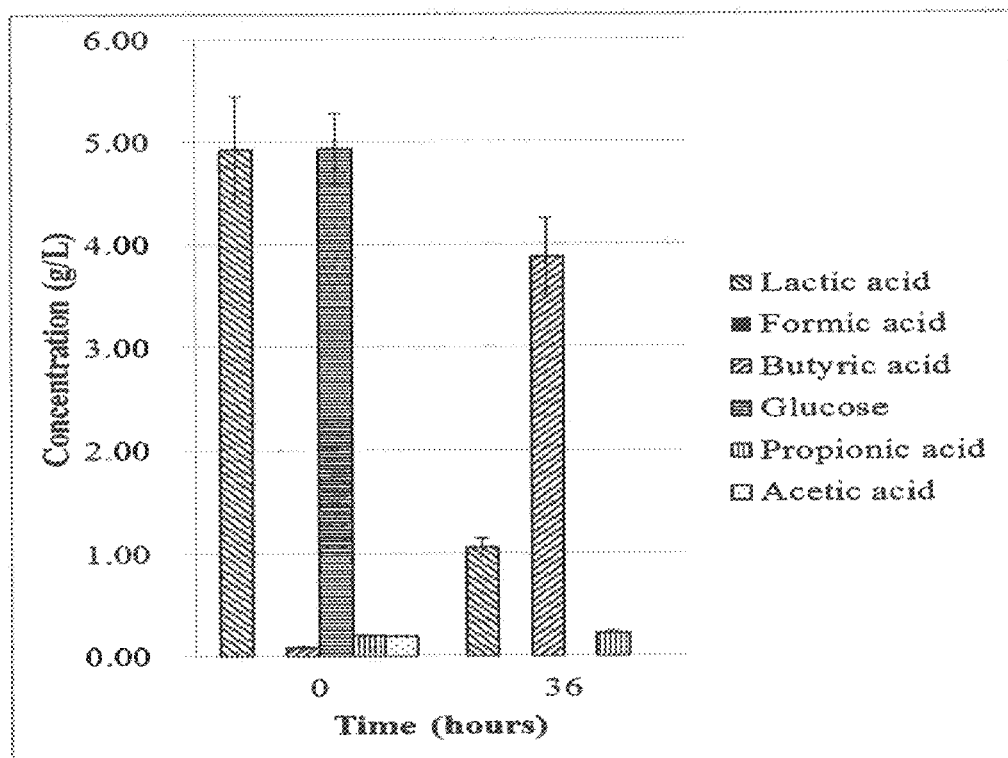

FIG. 3B shows the concentrations of various products of ITRI04001 in CGM medium containing 5 g/L of glucose and 5 g/L of lactate after 36 hours of cultivation at 37° C., under anaerobic conditions.

Example 2

Comparison of ITRI04001 with *Clostridium tyrobutyricum* van Beynum and Pette (ATCC® 25755)

Growth Rate

After ITRI04001 and ATCC® 25755 were cultivated in RCM medium until mid-log phase. Samples of the cultures were taken out and seeded into CGM medium containing (1) 5 g/L of glucose or (2) 5 g/L of glucose and 5 g/L of lactate at different dilution ratios. Growth of either ITRI04001 or ATCC® 25755 was monitored by measuring OD at 600 nm.

Figure 4:
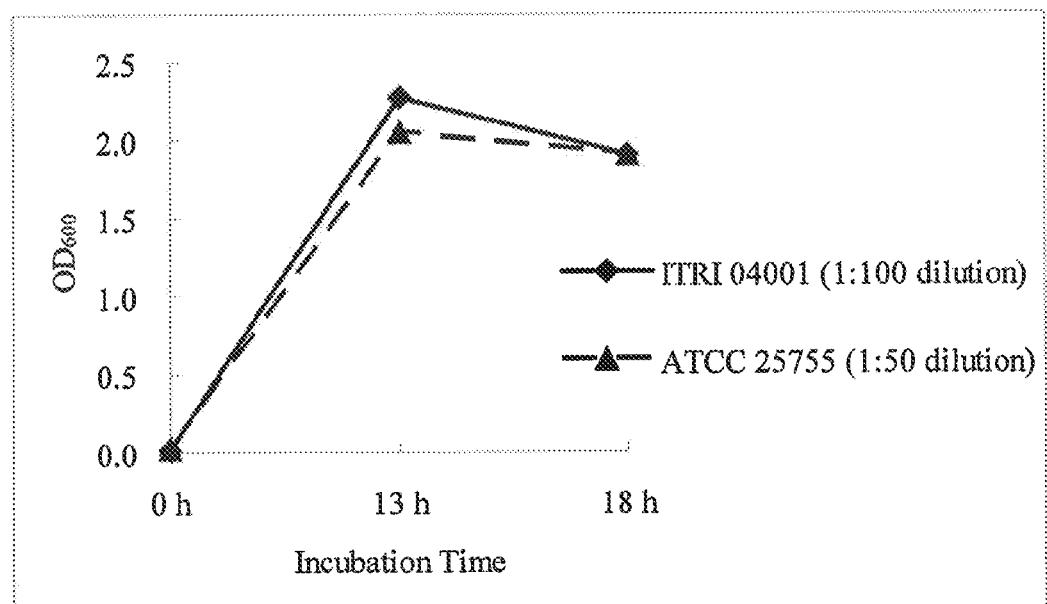

FIG. 4 shows that in CGM medium containing 5 g/L of glucose, the growth rate of ITRI04001 diluted at 1:100 ratio was higher than that of ATCC® 25755 diluted at 1:50 ratio.

Figure 5:
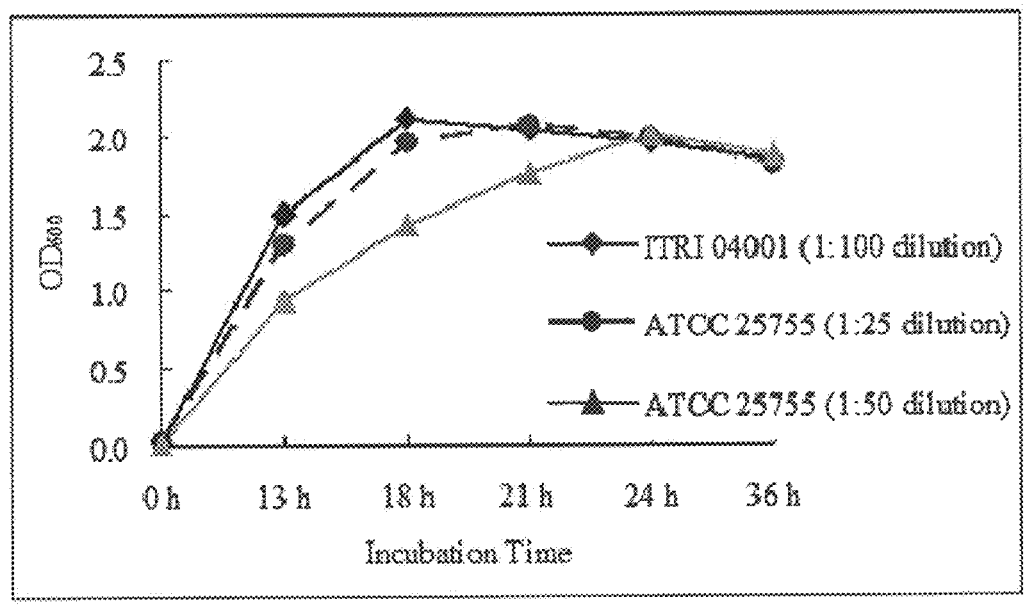

FIG. 5 shows that, in CGM medium containing 5 g/L of glucose and 5 g/L of lactate, the growth rate of ITRI04001 diluted at 1:100 ratio was higher than that of ATCC® 25755 diluted at either 1:25 or 1:50 ratio.

Butyrate Production

ITRI04001 and ATCC® 25755 were inoculated into CGM medium containing 8 g/L of lactate and 5 g/L of glucose at the same dilution ratio on stationary phase and cultivated at 37° C., under anaerobic conditions. After 24 hours of culture, samples of the culture media were taken for measuring the concentrations of butyrate, glucose, and lactate by HPLC.

Figure 6:
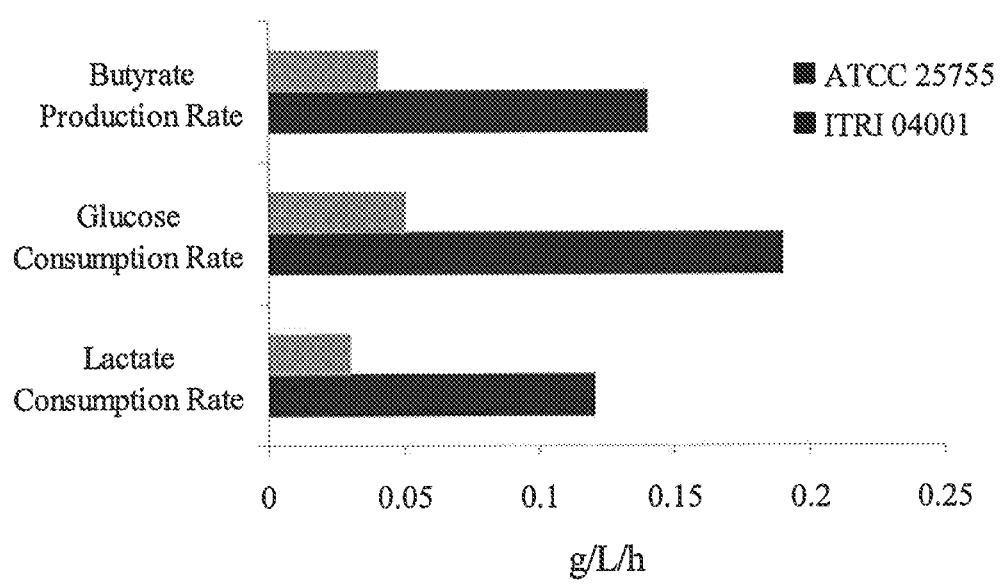

FIG. 6 shows the butyrate production rate, glucose consumption rate, and lactate consumption rate of both ITRI04001 and ATCC® 25755. The data shows that, in CGM medium containing 8 WI. of lactate and 5 g/L of glucose, ITRI04001 exhibited a higher glucose consumption rate and a higher butyrate production rate than ATCC® 25755.

Flagellin Gene

Two fragments of ITRI04001's flagellin gene (SEQ ID NO:34 and SEQ ID NO:36) were sequenced and compared to similar sequence segments in ATCC® 25755 (SEQ ID NO:33 and SEQ ID NO:35). ITRI04001 and ATCC® 25755 shared about 92% of sequence similarity with regard to the fragment 251/272 and 91% of sequence similarity with regard to the fragment 148/162. See FIG. 7, which shows the sequence comparisons between two segments of the flagellin gene in ITRI 04001 (SEQ ID NO:34, top alignment ans SEQ ID NO:36, bottom alignment) and ATCC 2577 (SEQ ID NO:33, top alignment ans SEQ ID NO:35, bottom alignment) as described in Example 2.

Example 3

Syngas Fermentation Using ITRI04001

Syngas fermentation using ITRI04001 was performed in a 200 mL bottle containing 50 mL CGM medium, pH 6.0, and without any carbohydrate. The sole carbon source provided to the ITRI04001 during the fermentation was from syngas comprising 10% $H_2$, 20% CO, 20% $CO_2$, and 50% $N_2$, which was pressurized to 20 psi gauge in the headspace of the bottle. All experiments were performed on a rotary shaker with 100 r.p.m. in 37° C. Culture medium was sampled at 0, 24, 48 and 62 hours culturing time and analyzed with HPLC (Agilent 1100 series with Aminex HPX-87H (300 mm×7.8 mm) column).

Figure 8:
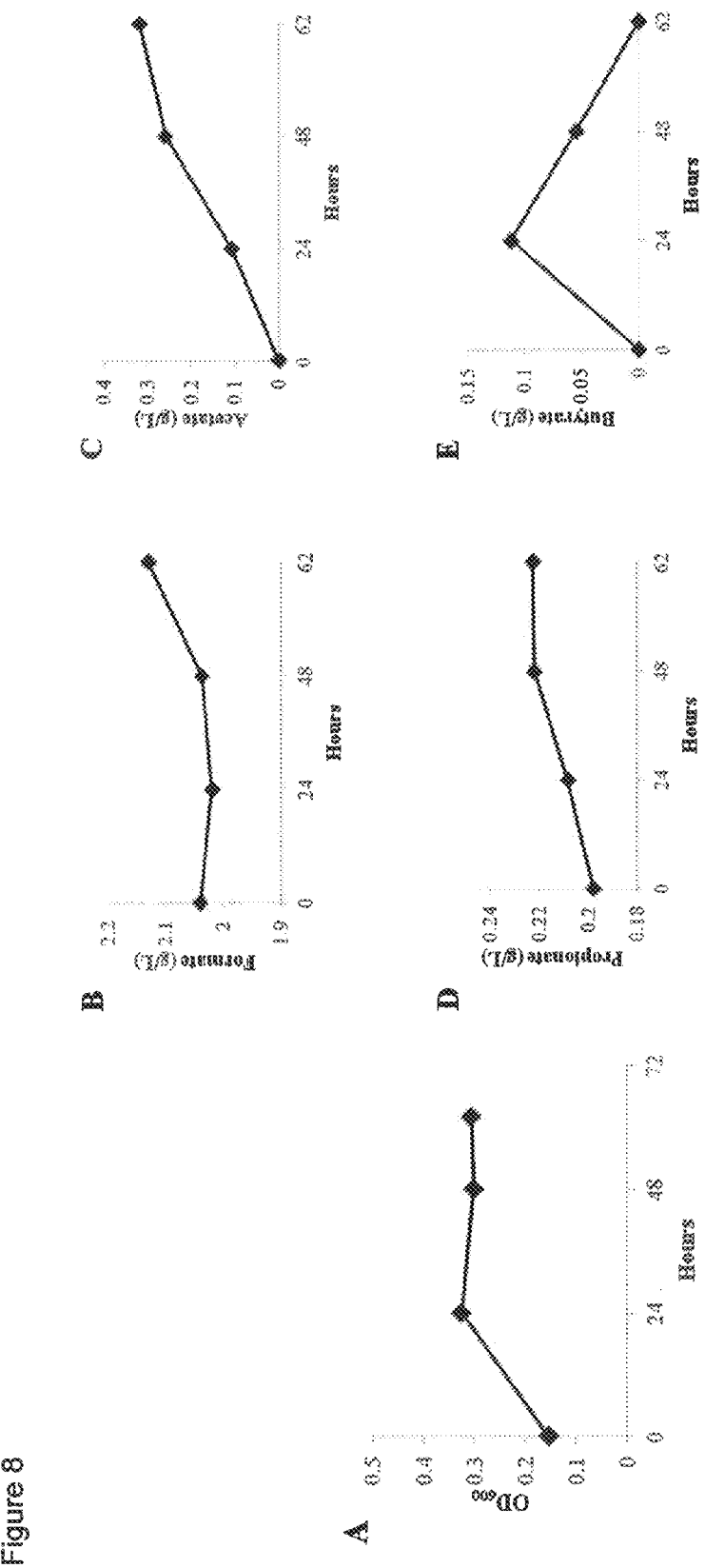

FIG. 8 shows (A) the changes of $OD_{600}$, (B) formate. (C) acetate, (D) propionate, and (E) buyrate in the medium cultivated for 62 hours with ITRI04001 and provided with syngas comprising 10% $H_2$, 20% CO, 20% $CO_2$, and 50% $N_2$.

Figure 9:
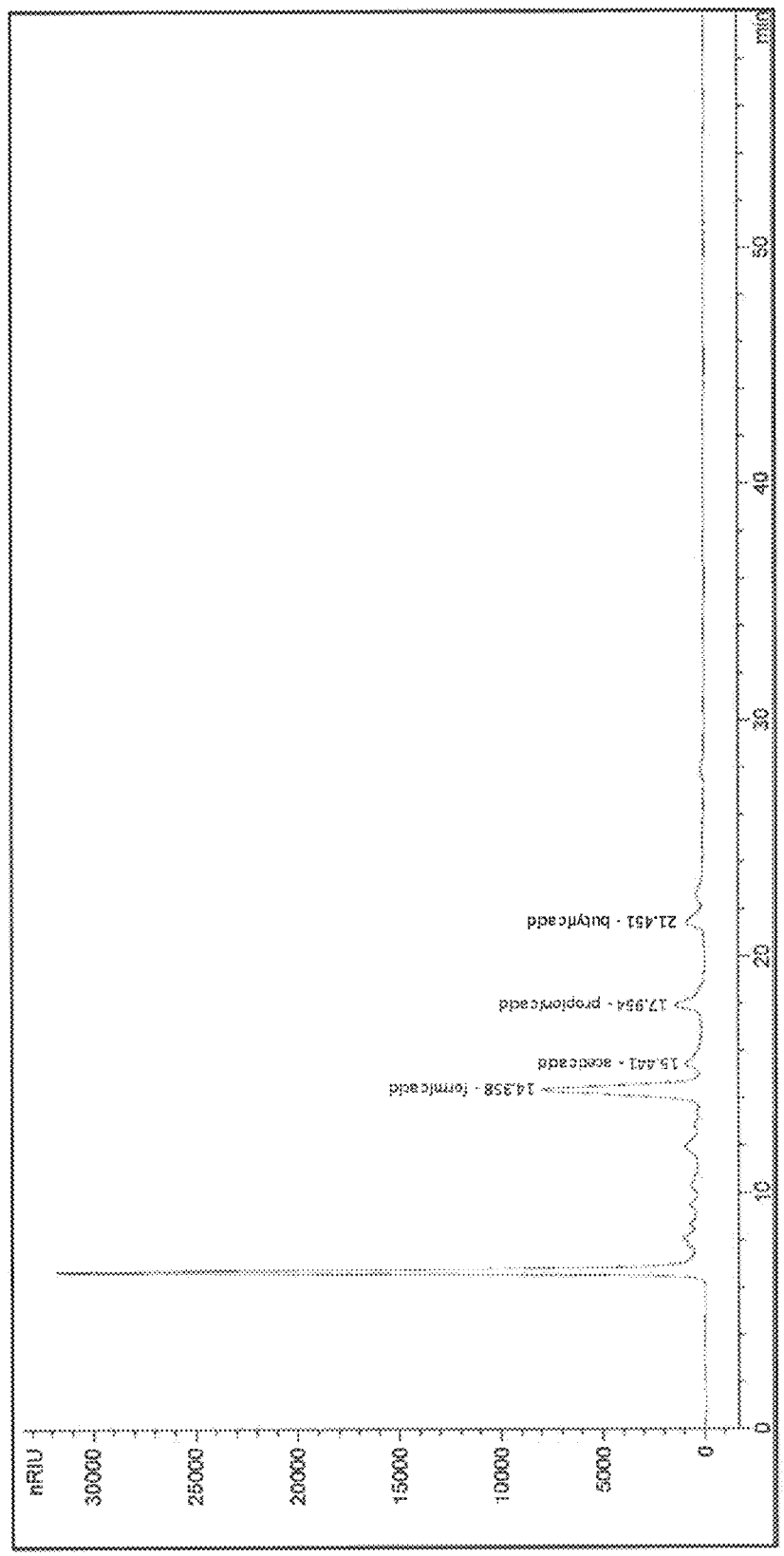

FIG. 9 shows the HPLC spectrum of a liquid sample taken at 24 hours from the medium cultivated with ITRI04001 and provided with syngas comprising 10% $H_2$, 20% CO, 20% $CO_2$, and 50% $N_2$.

It will be apparent to those skilled in the art that various modifications and variations can be made to the disclosed embodiments. It is intended that the specification and examples be considered as exemplary only, with a true scope of the disclosure being indicated by the following claims and their equivalents.

```
(16S rRNA)
>ITRI 04001_16S rRNA gene
                                                     SEQ ID NO: 1
TTTTAAATTGAGAGTTTGATCCTGGCTCAGGACGAACGCTGGCGGC

GTGCCTAACACATGCAAGTCGAGCGATGAAACCCCTTCGGGGGTGGATTAGCGGC

GGACGGGTGAGTAACACGTGGGTAACCTGCCTCAAAGTGGGGGATAGCCTTCCG

AAAGGAAGATTAATACCGCATAAAGCCAAGTTTCACATGGAATTTGGATGAAAGGA
```

-continued

GTAATTCGCTTTGAGATGGACCCGCGGCGCATTAGTTAGTTGGTGGGGTAATGGC

CTACCAAGACAGCGATGCGTAGCCGACCTGAGAGGGTGATCGGCCACATTGGAAC

TGAGATACGGTCCAGACTCCTACGGGAGGCAGCAGTGGGGAATATTGCACAATGG

GCGAAAGCCTGATGCAGCAACGCCGCGTGAGTGATGAAGGTCTTCGGATTGTAAA

GCTCTGTCTTTTGGGACGATAATGACGGTACCAAAGGAGGAAGCCACGGCTAACT

ACGTGCCAGCAGCCGCGGTAATACGTAGGTGGCGAGCGTTGTCCGGATTTACTGG

GCGTAAAGGGTGCGTAGGCGGATGTTTAAGTGAGATGTGAAATACCCGGGCTTAA

CTTGGGTGCTGCATTTCAAACTGGATATCTAGAGTGCAGGAGAGGAGAATGGAATT

CCTAGTGTAGCGGTGAAATGCGTAGAGATTAGGAAGAACACCAGTGGCGAAGGCG

ATTCTCTGGACTGTAACTGACGCTGAGGCACGAAAGCGTGGGTAGCAAACAGGAT

TAGATACCCTGGTAGTCCACGCCGTAAACGATGAGTACTAGGTGTAGGAGGTATC

GACCCCTTCTGTGCCGCAGTAAACACATTAAGTACTCCGCCTGGGAAGTACGATC

GCAAGATTAAAACTCAAAGGAATTGACGGGGGCCCGCACAAGCAGCGGAGCATGT

GGTTTAATTCGAAGCAACGCGAAGAACCTTACCTGGACTTGACATCCCCTGAATAA

CCTAGAGATAGGCGAAGCCCTTCGGGGCAGGGAGACAGGTGGTGCATGGTTGTC

GTCAGCTCGTGTCGTGAGATGTTAGGTTAAGTCCTGCAACGAGCGCAACCCTTATT

GTTAGTTGCTAACATTCAGTTGAGCACTCTAACGAGACTGCCGCGGTTAACGCGGA

GGAAGGTGGGGATGACGTCAAATCATCATGCCCCTTATGTCCAGGGCAACACACG

TGCTACAATGGGCAGAACAAAGAGAAGCAATACCGCGAGGTGGAGCCAAACTCAA

AAACTGCTCTCAGTTCGGATTGCAGGCTGAAACTCGCCTGCATGAAGCTGGAGTT

GCTAGTAATCGCGAATCAGCATGTCGCGGTGAATACGTTCCCGGGCCTTGTACAC

ACCGCCCGTCACACCATGAGAGCTGGCAACACCCGAAGTCCGTAGTCTAACGTAA

GAGGACGCGGCCGAAGGTGGGGTTAGTGATTGGGGTGAAGTCGTAACAAGGTAG

CCGTAGGAGAACCTGCGGCTGGATCACCTCCTTTCT (coos gene encoding carbon monoxide dehydrogenase)
>ITRI 04001_coos
                                                                          SEQ ID NO: 2

ATGGAAAATTGTAAAAGTTGTAGTATTTGTAATTCGGCAGACAAGGT

ATTGGAAGATTTCATTGAAACATTGGATATAGAGACTTCTCTTCATCGTGTAGAGAG

TCAGAAGTATAAATGCAACTTTGGGAAAAATGGTGTATGCTGTAAACTCTGTGCAAA

TGGTCCCTGTAGAATAAGTGAGAAATCTCCTAGAGGAATATGCGGAGCAACTGCC

GATACAATAGTTGCAAGAAATTTTTTAAGGGCTGTAGCAGCAGGTACTGCATGTTAT

CTTCATGTAGTTGAAAATACTGCCAGGAATTTAAAATCTACTGGTGAATCAAATGGA

AAAATCAAAGGAGAAGCTGCACTTAACAGACTTGCGGATACATTTGGAATATCAGA

GGCAGATATTCATAAGAAAGCTGTATTGGTAGCAGATAAAGTATTGAGCGATTTGT

ACAAACCTAGATTTGAAAAAATGGATTTGGTGAATAAATTAGGCTATGCTCCTAGAA

TTGAAAACTGGCAAAAATTGGGCATAATGCCTGGAGGAGCAAAATCCGAAGTATTT

GATGCTATAGTAAAACCTCTACAAATTTGAACAGTGATGCCAAGGACATGATGGT

AAACTGTTTAAATCTTGGAATAAGTACAGGAATTTATGGACTTACCCTTACAAACCT

ACTGAACGACATTCTACTTGGAGAACCTTCAATAAGGCCAGCTAAAGTAGGATTCA

AAGTAGTTGACCCTTCCTATATAAATATAATGGTAACAGGTCACCAACAATCAATCA

TATCATATCTTGAAGATATTCTTACAACTCCTGAAGTAATAAAAAAAGCACAGAAAG

-continued

```
CCGGAGCCAAAGGTTTCAAACTTGTAGGATGCACATGTGTAGGTCAGGATCTTCAA

TTAAGAGGAGAGCATTACAAGGATGTATTTTCAGGACATGCAGGCAACAACTTTAC

CAGTGAAGCACTAATTGCAACTGGCGGCATAGATTCCATAGTATCAGAATTCAATT

GTACACTTCCAGGAATAGAGCCTGTCTCAGATAAATTCATGGTAAAAATGATATGTG

TTGATGATGTAGCCAAAAAATCGAATGCAGAATATGTAGAGTACTCCTTCGATAAAA

GAAAGGAAATAAGCAATCATATAATAGACGAATCAATAAAGAGTTATTTAGACAGAC

GTCCTAAAATAAAGATAAACATACCTGAAAATCACGGTTTTGATAATGTTATAACGG

GCGTAAGCGAAGGATCACTTAAAGAATTTCTTGGAGGAACCTGGAAACCATTAGTT

GATTTAATTGCTGCAGGCAAAATCAAAGGAGTTGCAGGAATAGTTGGCTGCTCAAA

TCTTACTGCAAAAGGTCATGATGTATTTACTGTTGGACTTGCAAAGGAACTTATAAA

AAGAGACATTATAGTACTGTCCGCAGGATGCTCAAGTGGGGGCTTGAAAATGTG

GGATTGATGTCTCCCGAAGCTTCAAAACTTGCAGGTTCAAATTTAAGGGCAGTTTG

TGAAAGTCTTGGAATACCTCCTGTACTAAATTTTGGTCCATGCCTTGCTATAGGAAG

GCTTGAAATTGTAGCAAAGGAACTAGCTGAATATTTGAATATAGACATTCCAGCTCT

TCCATTAGTGCTTTCAGCTCCTCAGTGGTTGGAAGAACAGGCTCTTGCAGATGGAT

GCTTTGGATTGTCCCTTGGACTTCCACTTCATCTTGCAATTTCACCTTTTATAGATG

GAAGTGAAACTGTTTCAAGATTACTTACAGAAGACATGGAAAGTCTAACTGGAGGA

AAATTAATTATTGAAGGTGACATTAAAAAGGCTGCTGACAAACTTGAAGAAATAGTT

CTAGCTAAAAGAAAAGGCCTGGGACTTAGATAG (fchA gene encoding formyltetrahydrofolate cyclohydrolase)
>ITRI 04001_fchA
                                                 SEQ ID NO:3
ATGAAAATTATAGATATTCCATGTAGAAATTTTATAGAAGAACTTTCA

TCTAAAAGCGCTATACCGGGTGGTGGTGGAGCAGCAGCTTTAGATGGAGCCATGG

GAGCGGCTTTATTAAGTATGGTCTGTAATTFAACTATTGGAAAGAAAAGATATGTAC

AATATACAGATAAACTGACATCAGTGTTAAATAAATCAGCAGAATTAAAAAGTAATTT

TTTGAATATGGTAGATGAGGATGCAGAAAATTTTATCCCACTTTCAAAAGCTTATGG

TTTACCTAATAATACGGCAGAAGCAAAGCATGAAAGAGAAGAAATTTTAGAAAAGT

GTTTAAAATCTGCTTGTGGTGTTCCAATTAAGGTTGTGAAAAAGTCATACGAAACTA

TTCTTCTTCACCAATCCATATTAGAAAGTTGTTCTACTCTCGTACTAAGTGATGTTG

GAGTAGGTGTTCAATGTTTAAAATCTGCACTTACTGGTGCTTATCTCAATATAATTAT

AAATGTAAAGTCTATGAAAGATAGATGTTATGTAGATAATATTAAAGAGGAAATAGA

ACCATTATTAAAAGATGGAGTAAAAATTGCAGAGAAAGTTTATGATAGAGTTGTAGA

AAGACTTTCAGATTGA (fhs gene encoding formyl-THF synthetase)
>ITRI 04001_fhs
                                                 SEQ ID NO: 4
ATGAAATTTAAATCTGACATAGAAATAGCTCAGCAGTGTGATATCCAG

AACATAGTTAGTATAGCAAAAAAATTAAATATACCAGAAGATGATTTGGAACTGTAT

GGTAGATATAAAGCTAAAGTAGACTACAATATTCTAAAACGGACTACAAGTAAAAAT

GGAAAGTTGATATTGTGTACAGCAATAAATCCAACACCAGCAGGGGAAGGTAAGAC

TACTACATCCATAGGTCTTGCAGATGCATTTTCAAAATTGGGAAAGTCTACAGTAGT

TGCACTTAGGGAACCATCTATGGGACCGGTATTTGGAATCAAAGGCGGAGCGGCA
```

```
GGTGGAGGATATGCACAAGTCGTTCCTATGGAGGATATAAATTTACATTTTACAGG

AGATATACATGCATTGACTGCAGCAAACAATTTATTGGCTGCAATGATAGATAATCA

TATTCAGCAGGGAAATTCTCTTGACATAGATCCAAGAAGAATTACATGGAGAAGAT

GTATGGATATGAATGACAGACAATTGAGATTTGTTGTAGATGGATTAGGTGGAAAA

GTCAATGGAATGCCTCGAGAAGATGGATTTGACATAACAGTTGCTTCTGAAGTAAT

GGCTATATTCTGTCTGGCAAATGACATAAAGGATTTGAAAGATAGAATTTCAAAAT

AATCATAGGATACAACAGGAGTGGAGAACCGGTAACAGCACATGATTTAAAAGCTG

AAGGTGCCATGGCTGCACTTTTAAAAGATGCATTAAAGCCAAATTTGGTTCAAACA

CTTGAAGGTACTCCTGCATTTATACATGGTGGACCTTTTGCAAACATTGCTCATGGA

TGTAACTCTATAATGGCAACTAAAATGGCAAGACACTTTGGAGATTATGCTATTACA

GAAGCAGGATTTGGTGCTGATCTTGGAGCAGAGAAGTTTATAGACATAAAATGCAG

AATGTCAGGATTAAAACCAGATGCAGTAGTAATAGTGGCTACTATAAGAGCACTTA

AGTATAATGGAGGAGTGGAAAAGTCAAAGCTTGGAGAAGAAAATTTAGAAGCACTT

AATGCAGGTATCCCAAATTTATTAAAACATGTAGAAAATATAACCAAGGTATTTAAA

CTCCCTGCAGTGGTAGCTATAAATAAGTTCCCTACAGATACAGAATCTGAAATTAAG

CTAGTAGAATCTGAATGTAAGAAACTTGGGGTAAATGTAAAATTATCTGAAGTTTGG

GAAAAGGGCAGTGAAGGTGGAATAGAACTTGCCAAAGAAGTACTGAGAATAATAG

ATGAAGAGGAAAACAATTTTGAATTTGCATATGACATGGATTTATCTATAAAAGAAA

AGATAAAAACTATTGCAAGAAGAATATATGGTGCAAAAGATGTTGATTTTACAAAG

ATGCAGAGAAGGAAATTAAGAATTTGGAAAGGTTGGGTTTCAATAATATTCCTGTAT

GTATAGCAAAAACTCAATATTCCTTAACTGATGACAAGGCAAAACTTGGAAGACCAA

CAGATTTTACAATTACAGTAAGACAAATTTCTATTTCAGCTGGAGCTGGCTTTATAG

TTGCTGTTACAGGTTCCATAATGAAAATGCCAGGACTTCCTAAAGTTCCAGCAGCG

GAAAAAATAGATGTAGATGATAATGGAACAATAATCGGACTATTTTAG (folD gene encoding methylene-THF dehydrogenase/methenyl-THF
cyclohydrogenase)
>ITRI 04001_folD
                                                    SEQ ID NO: 5
ATGGGACAGTTAATTAAAGGGAAACCAGCAGCTGATGCTGTAACCG

TACATTTGATTGAAGAAGTAAAGAACTTAAAACGAAAAAATATTATTCCAAAGCTTAC

TATAGTTAGGGTGGGGAAAAATGGAAGTGATATGGCATATGAAAGAGGGGCAACC

AAAAGGTGTAATAGTATTGGCATAGAAATAGCTATAAAGGAACTTCCGGAGGACAT

ATCTCAACAGAGTTTTATAGATGAATTGAAAAAAATAAATGAGGATAGTACCACAGA

TGGAATAATGGTATTCAGACCATTGCCAAAACAATTAGATGAGGATATTATAAAACA

TTTGATAGATCCCAATAAGGATGTTGATTGTTTCAATCCATTAAATATGTCTAAATTG

CTGGAAGATGATAATTCTGGATTTTCGCCTTGTACTGCTGCTGCTGTAATTGAGATC

CTGGATTATTATAAGATAAAAATTGAAGGAAAAAGAGTGGTTGTAATTGGAAGGTCA

ATGGTAGTAGGAAAACCGCTTTCTCTACTTTTATTAAATAGGAATGCTACAGTTACC

ATTTGTCACTCTAGAACACAAAAGATGGAGAATATATGTTCCCAGGCTGATATTGTT

GTAGTGTGTATTGGAAAAAGTAAAATTATAAACAAAAGCTATATTAAATCAGGAGCA

GCTGTAATTGACGTTGGAATAAATGTAGACACCAATGGAGCTTTATGCGGAGATGT
```

-continued

TGATACTGAAAATTGTATAGAAAAGGTTGGTATGATAACTCCTGTACCTGGAGGAG

TTGGTTCTGTTACAACTTCTATACTTGCTAAACAAGTAGTTATGGCATGTAAGAGAC

AAAATAATATATAA (metF gene encoding methylene-THF reductase)
>ITRI 04001_metF
SEQ ID NO: 6
ATGCTTAAAGATAAAATATTGAATAGAGAAACTGGAATAATAACATAT

GCAATAACACCGCCAAAATTAAACAATTTACATCAAAAAATTGTAGAAATTTCTCAAA

AACAGGTAGAGCGGATAAAGAACATTGATGTAGATGGCCTAATTATTTATGATATTC

AAGATGAAATTGACAGACAGAAAGAAAAGAGGCCATTTCCTTTTATTGAAACATTGG

ATCCAGCTTTGTATAACGAGGAGTATTTAAAGAATTTAACTGTTCCTAAAATTATATA

CAGATGTGTAGGAAAATATGATGAAAATCAGTTTTCAAAATGGATAAAATCTGATAA

AGATAGCGATAGATTTTCTGTATTTGTTGGAGCATCTTCTAGTAAACAGGAAGTTAA

GTTGAAATTATCTGAAGCATATAGAATAAGTGAACAATTAAATCCAAATTTAATTTTA

GGTGGAGTTGTAATACCTGAAAGACATGTGACTCATAAAGATGAACATATGAGAAT

AATCAATAAAGTAGGTAAAGGATGCAAATTTTTCGTCTCACAGGTAATATATAATCT

GGAAAATTCCAAGAATTTTTTATCGGATTATTATTATTACTGTAAAAATAATAATATT

GAGATGAAACCTATAATATTTACTATTACGCCTTGTGGATCTAAAAAAACATTGCAA

TTCATGAAATGGCTTGGAATAAATGTCCCAAAGTGGATGGAAAATGATCTTATGAAT

TCACAGGATATATTGCATAAATCAGTATCTTTATCAGAGAATATTGTTGAAGAATTAT

TGGATTTTGCATTGGAGAAGGATATACCAGTTGGATTTAATATTGAAAGTTTGTCAA

TTAGAAAAGTTGAAATTGAAGCTTCAATAAAATTGGTTAAAGATATAAAATCAATAAT

TGAAAAGAGATTAAAATAG (aceE gene encoding methyltransferase)
>ITRI 04001_acsE
SEQ ID NO: 7
GTGACTTGTAATAATTTATTGGAAAAAATTAAGAATAATTTTATATTTT

TTGATGGAGCCATGGGCACTATGCTTCAAAGAGCAGGACTTAAAACAGGTGAGCTT

CCAGAAATTCTAAATATAACAAATCCAGATACTATAAAAAAAATACATGAAGCTTATC

TTAATGCAGGAGCTGACATTATAACTACCAATACTTTTTGGAGCAAATGATTTAAAAT

ATAGCTCTTCTGATTATTCATCGGAGGAGGTAATTGAAGCTGCAGTTGGAATTGCA

AGGGAAGCTGTTAAAAGCAGAGAAATAAATTTGTAGCTCTTGATATAGGACCAAT

AGGACAAGTGATGGAGCCTACTGGAAATTTAAGTTTCGATTCAGCTTATAAATTATT

CAAAAAGCAGGTAGTTGCAGGAGACAGGTCAGGAGCCGATCTTATAGTAATTGAAA

CTATGATGGATCTGTATGAGACTAAGGCTGCAGTGCTTGCTGCCAAAGAAAACAGT

TCACTTCCAGTGTTCTGTACTATGACTTTTGAAAAAAATGGAAGAAGCCTCATGGG

CACTGACCCTAAAACAATGGTATTTGTTTTAGAAGGACTTGGAGTGGATGCAATTG

GAGTTAATTGTTCCCTAGGACCTAATGAACTTCAGGGCATAGTAGATGAAATTTTGA

AGTATGCGTCTATTCCAGTTATGGTTCAGCCCAATGCAGGGCTTCCTAAATACAAT

GGAGTGGAAACTTACTATGATATAAGCATAGAAGAGTTTTCAAAAAATATAAAAATA

ATGGCTCAGAAGGGAGTAAGAATAATTGGAGGATGCTGCGGTACAAATCCTGATTT

TATAAAAGATTTTATAAAAGAATTGAAGGATATTAAACCTATAGATATAGGAGAAAAA

AACTACACAGCAGTAACTTCAGCAACTGAAACCGTAATAGTAGAAAATAAAACTAG

-continued

```
GATTATAGGTGAGAGAATAAATCCTACAGGGAAGTCCGCATATAAAAAGAACTTA

GGGAAAAGAGTATTGATTATATACAAAAGCAGGCTTTGATACAAAGAGATGAAGAA

GCGGATATACTCGAATTGAATGTAGGGCTTCCAGAGATAAACGAGGTTGAGATGAT

GAAGAAGGCAGTGAGAGCAGTACAAAAAGTAGTGTATACACCTATAAGCATAGATA

GTCCAAATGCAAGTGCACTAGAGGCAGGCGCAAGGTTATACAATGGAAAACCTCT

CATAAATTCTGTTAATGGAAAAGAAAAGACTATGGAGGATGTATTTCCAATAGTTAA

AAAGTATGGAGGATGTGTTATAGCACTTACTATAGATGAAGATGGTATCCCCAAAA

CCGCTCAGAAGAGATTTGAAATTGCGGAAAAAATAGTAAGGAGGGCAGCAGAATAT

GGAATACCAAAAAAGATATAGTAGTTGATTGTTTGTCACTTACAGCTTCAGCCCAA

CAGAAGGAAGTAATGGAGACGGTAAAGGCAATAAGGCTTGTAAAGAAGGATTGG

GTGTAAAGACTACTCTTGGTGTAAGTAATGTATCTTTTGGACTTCCACATAGAAAAC

TCTTGAACAGGACATTTTTGTTGCTTGCTCTTCAGGCTGGATTAGATCTTCCTATAA

TGAATCCTTCGGATAAGGGTATGAAGGATACTATAGCTGCATTTCAAGTACTTGCC

AATAGAGATGTAGACAGCAGGGAATTTATAGATAGATACAAGGATGAATCAGAGGA

ATCAAATAATAGCCGATTATCTGCAAAAAAAGTCAAGGATAAGAATTTTGACAATAT

AAAGTTGGATAAAAATAGCAGTGACTTAAAACAGATAATTATAAATGGTGATGAAGG

TGCAGCATCTTTAGCTACTGAAGAACTTTTAAAATCCAAACAACCCCTTGATGTGGT

AAATTCATATATAATACCAGCGCTGGATCAAGTCGGAGTAAAGTATGAAACAAAGG

AGATATTTCTACCGCAGCTCATACAGGCGGCTGAAACCGTAAAAAAATCATTTGAA

GTTATAAAAAAAATCATAGTTGAAAATGGTGGTCAGAATGTAGAAAAGGGAAAAGT

GATTTTGGCTACAGTCAAGGGAGATGTACATGACATAGGAAAGAATATAGTAAAAG

TCCTCCTTGAAAATTATGGGTTTAATGTAATTGATCTTGGGAAAGATGTAGATATAC

AGAAAGTAGTTGATGCTGCAAAAGAAAATAATATAAGACTTGTAGGGTTAAGTGCA

CTCATGACTACTACCGTTATGAATATGAAAAAAACTATAGATGCATTGAAAAAAAAT

AATTTATCATGTAAAGTTGTAGTAGGCGGCGCAGTGCTGAATCAGGAATATGCAGA

TATGATAGGCGCTGATTTTTATGCAAAAGATGCCAGAGATACAGTTAAGATAGCTG

AGGAATTATTTTCAAAAGATAAAGTAGGAACAAATTAG (fdh gene encoding formate dehydrogenase)
>ITRI_04001_fdh
                                                    SEQ ID NO: 8
ATGGAGATAAAACAGTCCACTTGTAATTATTGTTCTCTAGCCTGTAAT

CTGGAATTTTATGTAGAAGATAATATGATTAAAAAAATATTGCCTAAAAAGATTACC

CTGTGAATGGAAAATTCACCTGTTTAAAAGGTATAAATCTTGATAAACAGTGCAGTA

GATATGGAAAAGATAAACTACCTGTGCTGAAAGACGAATATGGAAATAAAAGGGCT

ATTTCATGGAATGAGGCCTTTGAATTATTTGCAGATAAAATGCGGTACATACAAAAT

AAATACGGAGTTGAAAGTGCTGCATATATAAGCACAGGCCAGATAACTACAGAAGA

ACTTGCACTTTTGGGACTTGTAGGCAGAATACACATGGGCATAAATGGAGATGGCA

ATACAAGGCTTTGCATGGCTTCTACAGTTATGGCGTATAAACAGAGTTTTGGATTTG

ACGCTCCTCCCTATACATTAAAGGATCTTGAAATTTCAGATACACTTGTATTTATAG

GAGCAAACCCCGCTATTGCCCATCCTGTAGCCTGGTCTAGAGTCAAAAAAAATAAA

TCTGCCAGTATAGTGGTCATAGATCCAAGAGAATCAGAGACAGCACAAAATGCGGA

TATTTGGCTGGATATAATTCCAAAGTCAGATATTTATCTTTTGTATACACTTGCCAAT
```

-continued

```
GTGCTTATAGAAAATAACTGGATTGACAGAGAATATATAGATAATTATACTATGGAT

TTTGATGGATTTAGAGACCACATAAAAAAGTATAATATTGCAAGTGTGGAGAAAAT

ACCGGTATATCGAGTGAAAGAGTGCTTGAACTTGCGCAGTTGATCCACAATGGAAA

GAGAGTGTCATTTTGGTGGACCATGGGTGTAAACCAGGGGTATCAGGCTGTAAGA

ACTGCACAGGCAATTATAAACATTGCAGTTATGACTGGGAATATTGGAAGAGAGGG

AACAGGACCAAATTCATTAACTGGACAGTGTAATGCAATGGGATCTAGAATGTTCA

GCAATACCACGGCCCTTTATGGAGGAAGGAACTTTGACAATCCTAAACACCGAAG

GGATACAGCTGAAATTCTTGGAGTGGATGAAGAAAGATTCCTAAAAAGCCTACTA

TACCCTACAGTGAAATAATAAACAGGATAGATAGGGGTGAGATAAAATCACTTTGG

GTTATTGCCACCAATCCCAGGCATTCATGGGCCAACAACAAGGAATTTGAAAATGC

AGTAAAAAAACTGGACTTTTTTGTAGTACAGGATCTCTATGGAGATACAGACAGTTC

AAAAATATGTGACCTGTTTCTTCCTTCCGTTCCACTTACAAAAAAGCAAGGATCCAT

TATAAATACTGAGAGAAGATTGTCGGCAGTAGTACCTGTAATTGATATGGGAAAAG

ATGAGATGAGTGACTATGATATATTCCTGGGAATAGGGAGAGCTCTTGGAATGAAA

CAAGAACTTGAAAAGTGGAAAACCCCACTTGACGCATTTAATACCATAAAAGAACT

CAGCAGGGGAATGCCCTGTGATATAACAGGCATAGATTATGAAATGCTTGTAAACT

CCAAAGGGATACAATGGCCTTTTAAAAGTGGGGACAAATTACTTCAAGATGAAAGA

AGACTTTTTGAGGACAATATATACTTTACCCAAAACGGAAGGATGAAGTTCATATAT

GAGAATGTAATGGAAAATCCGTGTCCGGTCGATTCAAAATTTCCATATATATTGAAT

ACGGGCAGAATATCCGTAGGCCAGTGGCATACTCAGAGCAGAACAAGAGAAATAA

ATTCAGGAAATTCTTCAATTGTTAAAGCAGCATATGTAATACTCAATGTGAAATTGG

CTGAAACACTTGGCATAGAAGAAGGTGACAATGTAATAATTTCATCTATAAATGGAA

ACAACAGTAAATTCAAGGCGAGATTAAGTAGTATGATTAAAGAAAACCAACTGTATG

CGCCTCTGCACTATATAGAGACAAATGTACTTTCTGTTTCAGTATTTGATACCTATT

CAAAAGAACCTTCTTATAAATATATACCTGTAAATTTAGAGAAAATCTAA
```

(pyk gene encoding pyruvate kinase)
>ITRI 04001_pyk

SEQ ID NO: 9
```
ATGATTTTTACCGTTGGTCCTGCTAGTGACACAGATGAAATTTTATC

AAAACTTATTGAGGCTGGTATGAGTGCTTCAAGACATAACTTTTCACATGGTGACCA

TGAAGAGCATAAGGGAAGAATGGATGCAATAAAGAGACTTAGGAAAAAATACAATA

AACAAATAGCTATAATTCTTGATACAAAAGGACCAGAAATAAGAACCGGGGATTTTA

AAAGCAAGCTTGAATTAAAAGAAGGTCAAAAATTCACTGTATATTGTGGAGAAGAA

TTCTTGGAGATGAAACTAAGTGTTCCATAACTTATGCAGATCTTTATAAAGATGTAA

AGCCTGGAGACAGCATACTTATTGATGATGGATTAGTAGGTATGGAAGTTGAAAGC

ATAGATGGAAACAAAATAAATTGTGTAGTTAAGAATAGTGGTTTAGTTAGCAGTCAT

AAAGGTGTTAATGTACCAGGAGTATCCATAAAGCTTCCGGCTACTACAGAAAAAGA

CGAATCAGATTTGAAATTTGGATGCGAACAAGGCGTGGATATAATAACAGCATCCT

TTATAAGAAAGCCCAAGACGTAATAACTATAAGAAATATACTTAAGAAAAATGGCG

GAGAACACATCCAGATATTCTCAAAGGTAGAAAATCAGGAAGGTGTAGACAATATA

GATGAAATAATAGAAGCTTCAGATGGAATAATGGTTGCAAGAGGAGATATGGGAGT

TGAAATTCCAATAGAAAAAGTACCTCTTATACAAAAGTCCATAATAGCTAAATGCAA
```

-continued

TAGTGTAGGTAAACCTGTTATAACAGCTACTCAAATGCTTGATTCAATGATAAGAAA

TCCAAGACCAACAAGAGCAGAAGCATCAGATATAGCAAATGCAATTTTTGATGGAA

CAGATGCTATAATGTTAAGTGGAGAATCTGCAAATGGTAAATATCCTGTAGAAGCA

GCACAGACTATGGCAAGAATAGCTCAATCTGCAGAATCCAAGATTAATTTTGATGA

ATTACTTAAAAAGAAAAGAGAAGCTAGTGTAACTGATGTATCCAATGCTATAAGTTT

TGCAGCTTGTTCTACAGCAGCTGAATTAAATGCAGATGCAATAATAACAGCTACTCA

GAGCGGAAGTACAGCTGTAAGAGTTTCAAAGTACAGACCTGCTTGTCCGGTTATTG

CAGCTACTCCAAATGAAAAGTATGTAGAAAATTAGCTCTTAATTGGGGGGTTTTTG

CAATACTTACAGATAAATATGAATCTACAGATGAAATGGTAGAAAAATCTATAGATG

CATCATTAAAAGCTGGTTATATAAAGAAAGATGATTTGGCAGTTATAACTGCAGGAG

TACCAGTTAGCACTACTGGTACTACAAACATGATCAAGGTTAATGTAGTTAAATAA (pfor gene encoding pyruvate ferredoxin oxidoreductase)
>ITRI 04001_pfor

SEQ ID NO: 10

ATGGATGGTAATACAGCCGCTGCACATGTGGCTTATGCATTTACTGA

AGTAGCAGGTATCTATCCTATCACACCATCAAGTCCAATGGCTGATGTTATTGACC

AATGGTCTGCTGCAGGACGTGAAAATATTTTTGGTAATCAAGTTAATGTTGTAGAAA

TGGAGTCTGAAGCAGGTGCTGCAGGAACTGTTCATGGTTCTCTTGCTGCTGGAGC

TATCACAACAACATTTACAGCATCACAGGGTCTTCTTTTGATGATTCCTAATATGTAT

AAAATTGCTGCTGAACAGCTTCCTTGCGTATTTGATGTATCAGCACGTACCGTTGCT

ACTCAGTCACTTAATATATTCGGTGACCACAGTGATGTATATGCTTGTCGTCAGACA

GGTTTCGCAATGCTTGCTGAAACAAATCCACAGGAAGTAATGGATTTAAGCCCAGT

TGCACATCTTTCTGCAATTGAAGGTAAAGTTCCATTTATAAACTTCTTTGATGGATTC

CGTACATCTCATGAAATTCAGAAAATAGAAAAATGGGATTATGAAGATCTTAAAGAA

ATGTGCAACATGGATGCGGTTAAAGCTTTCCGTGAACATGCATTAAACCCAGAACA

CCCAGCTATGCGTGGTTCCCACGAAAATGGAGATGTATTCTTCCAGCATCGTGAAG

CAAGCAACACAACTTACGATAAATTACCAGCTGTTGTTGAAAAATACATGGCTAAG

GTAAATGAAAAACTTGGTACAAACTATGACCTGTTCAATTACTATGGAGCTCCTGAT

GCTGACCGTGTCATCATCGCTATGGGATCTATATGTGATGTAGCTGAAGAAGTTAT

TGATTACTTAACAGCTAGGGGAGAAAAAATTGGAATAGTTAAAGTTCGTTTATATCG

TCCATGGGTATCCAATTCACTTCTTAAAGTTTTACCTAAAACAGCTAAAAAGGTTGC

AGTTCTTGACCGTACAAAAGAGCCAGGAGCACTTGGAGATCCACTATATCTTGATG

TAGCTACAACTCTTCGTGAAGCAGGACTTAATGACGTAGTATTAACAGCTGGACGT

TATGGACTTGGTTCTAAAGATACTCCACCTTCAAGTGTATTTGCTGTATATACTGAA

TTGAAGAAAGATGCTCCTAAAGCTCGTTTCACAATCGGTATAGTTGATGATGTTACA

AACTTGAGTTTGCCAGAAGTTAAACCAGCTCCTATTACATCTGCACCTGGAACTGT

AGAATGTAAATTCTGGGGTCTTGGCGGTGATGGTACAGTAGGTGCCAACAAGAAC

TCAACAAAGATCCTAGGAGACCATACAGATAAATATATTCAAGCATATTTCCAGTAT

GACTCCAAGAAAACTGGTGGTGTAACAATATCACATCTTAGATTTGGTGACAAGCC

AATCAGAAGCCCATATTATATAAATCAGGCCGATTTTGTTGCATGTCATAATCCATC

ATATGTTGTTAAAGGATATAAGATGGTTCAGGACGTTAAACCAGGTGGAACATTCAT

GATCAACTGTCAGTGGTCAGACGACGAACTGGATTCTAAGATAACTGCTGATTCTA

-continued

```
AGAAATACATAGCAGATAACAACATCCAGTTGTATACAATCAATGCTATTGACAAAG

CAATTGAAATTGGTATGGGTAAACGTACTAATACAATTCTTCAATCTGCATTCTTTAA

ATTGGCAAATGTTATGCCAATTGATGATGCTGTTAAGTTTATGAAAGCTGCTGCTAA

AAAATCCTATGGTAAAAAAGGCGATGCAATTGTAGAAATGAACTATAAAGCAATTGA

TGCCGGTGTAGATGCTGTTCATAAAATAGATGTTCCAGCTTCTTGGAAGAATCCAG

CACCAGACGCTCCAGCTCCAAAACTTGAGGGACGTCCAGAAACAGTTAAGATGGT

TAAAAATCTTATGAATCCTATTACACTTATGGATGGAGACAGTCTTCCTGTATCTGC

ATTTGAAGAAAATCCAGATGGACAGTTTGAAATTGGTGCTGCTGCATATGAAAAAC

GTGGTACTGCTGTAAATGTTCCAGAATGGGATCCAGATAAATGTATTCAGTGTAAC

AGTTGTTCATTTGTATGTTCTCATGCAACAATTCGTCCATTTATGTTAAGTGAAGCT

GAAGTAGAAGCAGCTCCTTCAAACATAAAAGTTGCTGATACTAAGCCAAAGGCTGG

AAAATTCAAGTTTACAATGAGCGTAACTCCTCTTGATTGTATGGGATGCGGAGAAT

GTATTACCGTTTGTCCTACAAAGGCTATCAAGATGGTACCTCAGGAATCACAACTA

GACCAGCAGCCAGTATTTGACTACTTAGTTGCTAACGTAGGCAAGAAGCCAGGAG

TACCAGCTGATACTACAGTTAAGGGTTCACAGTTCAATCAGCCACTTCTTGAGTTCT

CAGGAAGCTGTGCAGGATGTGCTGAAACATCTTATGCTCGTTTGCTTACACAATTG

TTTGGTGAACATATGTACATCTCAAATGCTACAGGATGTTCTTCTATCTGGGGTGGT

CCTGCTGCAACAAGTCCATTTACAGTTAATAAAGATTCAAATATGGGTCCAGCTTG

GGCTAACTCATTATTTGAAGATAATGCAGAACATGGATTTGGTATGTATCTTGGACA

GAAGACACTTCGTGACCAAGCTATAGCTAAAATCGAGAAGATGGCTGCTTCTGACA

AAGCATCTGATGAATTAAAAGCTGCTGCTAAGAAGTTTATAGAAACAAAAGATAGTA

CAAAAGAAAACACAGCTGCTGCTAATGCATTAGTAGCTGAACTTGAAAAAGCTGCT

GCTGCAGGCTGTGATACTTCTAAAGAATTACTTGCAAGTAAACAGTACCTTGCTAA

GAAGTCAGTATGGATTCTTGGTGGAGATGGATGGGCATATGATATCGGATTCGGT

GGACTTGACCATGTACTTGCTTCAGGAGAAAATGTAAATGTCATGGTATTCGATAC

AGAAATGTACTCAAATACAGGTGGACAGGCTTCGAAGGCTTCCAACATCGGTGAA

GTTTGTCAGTTCGCTGCTGCTGGTAAAGAAGTTGGAAAGAAGAGCCTTGCTGAAAT

AGCTATGAGCTACGGATATGTATATGTAGCACAGATTGCTCTTGGTGCAAACCCAG

CTCAGACTGTTAAGACTATTTCAGAAGCAGAAGCTTACAATGGACCATCACTTATAA

TCGGATATGCACCTTGTGAACTTCACGGAGTTAAGGGCGGCATGAATCATTGTCAG

GATGAGATGAAGAAAGCTGTAAAGGCTGGATACTGGAATCTGTTCTCCTTTAATCC

TCTTCTTAAGGCTGAAGGAAAGAATCCATTCACTCTTACATCTAAACCAGGTGATG

GAACTTATCAGGACTTCTTGAACAATGAAACACGTTATACTCGTTTGAAACGTGCAT

TCCCTGATCGTGCAGAGAAGTTGTTCGATAAATCTGAGGAATCTGCAAAAGATCGT

TATGACCATTTGTTAAGATTAGTAGAACTTTATAAATAA
```

(pfl gene encoding pyruvate formate-lyase)
>ITRI 04001_pfl

SEQ ID NO: 11

```
ATGCAAAATAGTAAAAATATTTTTAAAAGGAGAAATATTATGAAAAAC

CAATGGAATAATTTTAGTGATGGTGCATGGACAGAAAATATTGATGTGAGAAATTTT

ATACAGAAAAACTACAAGCCTTATGGTGGTGATGAAAGCTTTTTAACATCTCCTACT

CTTAAAACTAAAAACATATGGGAAAAATCGGAAAAACTGATTTTACAAGAAATTAAA
```

```
AAAGGCGGAGTTTTAGATGTAGATACTAAAACAGTATCTGGTGTTGACAACTTTAAA

CCTGGATATATAGATAAAGAAAATGAGGTAGTATTCGGGCTTCAAACTGATGCTCC

ACTTAAGAGAATGGTCAATCCTTTCGGGGAATAAGAATGGCTCAAGAGGCACTTG

AAGACTATGGATATAAAGTAGATGATGAAATGCATGATATATTTACAAAATATAGAA

AGACACATAATGAAGCTGTATTTGATGCATACACGGAAGAAATGAAAGCGGCAAGA

CATGTTGGACTATTAACTGGACTTCCTGATGCCTATGGCAGGGGAAGAATAATAGG

TGATTTTAGAAGAATAGCTCTATATGGTATAGATTATTTAATAGAAATGAAGAAAAGT

GATTTAAAGGCCTTAAAAGGTGATATGGATGAAACTTTAATAAGAAGGAGAAGAAGA

AGTAGCAGAGCAGGTCAAGGCACTTAAAAAGATAAAGAACATGGCATCACGTTATG

GAATAGATATATCAGATCCTGCGGCGAATGCAAAAGAAGCTGTACAGTTTACTTATT

TTGGATATCTTGCAGGAATAAAGGAGAATAATGGTGCAGCAATGTCACTTGGAAGA

GTTTCAACGTTTTTGGATATCTATATAGACAGGGATTTAAAAGCGGGAATAATAAGT

GAGCAGGGTGCACAGGAGCTAATAGACCAGTTTGTAATCAAACTAAGGCTTGAAA

GACATCTTAGAACACCTGAATACAATGAACTATTTGCAGGAGATCCTAATTGGGTTA

CTGAATCCATAGGTGGTATGGGAATCGACGGCAGGACATTGGTTACTAAAAATTCT

TATAGATTTTTAAATACACTTATAAATCTGGGGCCTGCTCCAGAACCAAATATGACT

GTATTATGGTCTGAAAATCTTCCAGAACCATTTAAAAAGTACTGCAGCAGAATATCT

ATAGAAACAGATGCAGTTCAGTATGAAAATGATGATGTGATGAGACCTATATATGG

AGATGACTATGCTATAGCATGCTGTGTATCAGCTATGGCAGTAGGAAAACAGATGC

AGTTTTTCGGAGCCAGATGCAATCTTGCAAAGTCTCTTCTCTATGCTATAAATGGAG

GAGTTGACGAGAAAAAATTCCAAAAAATAGTACCGCATATAGATAAAATGGATGAT

GAAATACTTGACTATGACAAAGTTAAAAAGAGTTATTTTAAAGTTATGGAATATGTA

GCAAAACTTTATGTFAATACCCTTAACTTGATTCACTATATGCATGACAAATATGCTT

ATGAAGCTGCACTTATGGCACTCCATGACACAGAAGTTCATAGATTTCTTGCTTGC

GGTATAGCAGGACTTTCTGTTGCAGCAGATTCATTAAGTGCAATAAAATATGCCAG

TGTAAAACCAATAAGAAATGAACAGGGTATTGCTGTAGACTTTGAAGTTGAAGGAG

ATTTTCCTAAATACGGTAATGATGATGACAGGGTAGATGACATAGCAGTTGAAATTG

TAAATAAATTTATAAGTGAACTTAGAAAAACAGAAGCATACAGAAATGCGGAACATA

CTTTGTCGGCTCTTACTATAACTTCCAATGTAATGTATGGTAAAAAGACTGGAACTA

CACCGGATGGAAGAAAATCTGGAGAACCACTTGCTCCAGGAGCCAACCCAATGCA

TGGAAGAGATAAAGAAGGGGCACTTGCATCTTTGAATTCTGTAGCCAAAATACCAT

ATAGATCCGTATGTCAGGATGGTGTTTCAAATACATTCTCAATTGTTCCTGATGCTC

TTGGAAAAGATGAGAACAACAGGGTTGACAATCTTGTTTCAATCCTAGATGGATATT

TTTCAAAAGGTGCACATCATCTGAATGTAAATGTAATGAACAGGGAAACACTTTTAG

ATGCAGTAGACAATCCAGAGAAGTACCCTACACTGACTATAAGAGTTTCAGGATAT

GCGGTTCACTTTGTAAAGCTGAATAGGGAACAACAGATGGAAGTAATACACAGAAC

TTTCCATGAGAGGGTTTAG (pflA gene encoding pyruvate formate-lyase-activating enzyme)
>ITRI 04001_pflA
                                                        SEQ ID NO: 12
ATGGGCAGGATTCATTCTATAGAAACCATGGGACTGGTTGATGGAC

CTGGAATAAGGGTAGTTGTATTTTTCCAGGGCTGCAGACTTAGGTGTGCTTTTTGT
```

-continued

```
CATAATCCTGATACATGGAAACTGGATGCCGGAGAGGACATTAGTGCAGAGCAGC

TTCTTGAAAAAGTTGAAAGATACAGAGTCTATTTTGAAAAGTCAGGAGGGGGAGTT

ACCTGTTCTGGAGGTGACCCTCTAATGCAGCCTGAATTCTTGATTGAATTTTTAAAA

CTATGCAGGGAAATGGAATAAATACCATAGTTGATACATCTGGGTTTGGAAAAGG

AAATTATAAGGAAATTTTAAAATATACGGATCTTGTAATGCTTGATATAAAACATATT

GATGATGCTGGATATAAAGAACTTACAGGTGGAAATATTCAGGAGTTTTATGATTTC

CTAAAGGAAGTTAATAATTCAAATGCAAAATTGTGGATAAGGCACGTAATGGTTCCA

GGTGTAACTGACAATTATGAATGCATGGATAAAATAGTCCATATAATAGAAAACTCT

GTTAAATCAAATAAACTGGAGAAATTTGAAATTTTACCATATCATACTATGGGAGTA

AACAAATATGAAAAATTAGGTGTGGAATACAGGCTTAAAGGTGTCAAGCCAATGGA

TAAGAAAAGAGCCCTGGAATTTCAAAAATATGTTGTAGAAAAAATCAATAAAAATAA

AAGTATCACAATTTAA
```

(pflD gene encoding pyruvate formate lyase)
>ITRI 04001_pflD
SEQ ID NO: 13

```
ATGGCAGAATCAGTATTAAAAGAAGTAAAAAGAGGTTCAACAGAACG

TATAAGGAGATTAAGAGAAATTAGTACTAAAAAAAGTAAGCCCAGTATTTCCATGGA

GAGGGCAGTTTTATTAACAGAAGCTTACAAAAAGTATGAAGGAAAATTTTCAACTCC

AGTTCTTCGTGGATTAGCTTTTAAGTACATTATGGAAAATCGTACACTTTACATTGAA

AAAGGCGCTATCATATTAGGAGAAAAAGGACACAAGCCGTGGGCTGCACCAACTT

TCCCGGAATTATGCTGTCATACTATGGAAGATTTTAATAATATGAACAACAGGGAAA

AGGTCTTTTTTAAAGTTTCTGAAGAGGACATGAGAATTCAGAAAGAAGTAATTATTC

CTTACTGGAAGGATCGTGCGCTGATGACACGGATGAACAGATTATTGCCGGATGA

ATGGCACAAGCTGTTTGATGCAGGGCTGTATACTGAATTTTTGATGCAGCGTGGTC

CAGGGCATACTGTAGCTGACGGCAAGATATACCGTAAAGGGTATGCTGATTTTATT

GATGATATTCAATATGAAATTGACCATTTGGATTACAATAATGATGTACTTGCACTTA

ATAAAAAGGAAGAATTGGAAGGCATGAAGCTGGTTTGCGAAGGCATGATTATCTTT

GGACAGCGTTATGCAGCCAAGGCACGTGCACTGGCATCCATTGAAGAGGATTCAC

AATGGAAACAGGAATTATTGGATCTGGCTGAAGTTTGCGATGCAGTGCCAAAACAT

GCACCAGAAACCTTCCGTCAGGCAGTGCAGATGTACTGGTTTACCCATATAGGAGT

TACTACTGAAATGAATAACTGGGATGCTTATTCTCCAGGTAAATTTGATCAGCATCT

TGAACCTTTCTATGAGAAAGATATCGAAGAAGGTCGTCTGACTCGTGAAGGAGCCC

GTGAAATTTTAGAAAATCTATGGATACAGTTTAACAATCAACCTGCACCTCCAAAGG

TTGGGATAACTTTAAAGGAAAGTGCTACTTATACGGATTTCTGCAACATTAATACAG

GGGCTCTGCGTGCTGATGGAACAACAGGTGTAAATGAAGTCAGCTACTTGATTCTG

GAAGTAATGGATGAGATGAAATTGCTGCAGCCTAGTTCAAATGTACAGATATCCCG

CAAAACTCCAGAAAAATTCCTGCGTGAGGCAGTGAAAATTTCACGTAAAGGATGGG

GOCAGCCAGCCTTTTACAATTCCGAGGCTATTATACAGGAATTGTTGTTCCTTGGT

AAGTCCATTGATGACGCCAGAGAGTGCGGAATTGCCAGCGGATGTGTGGAAACTG

GTACAGCTGGGAAGGAAGCTTATGTACTGACTGGATATTTGAATATACCAAAAATC

TTFGAACTGGTGTTGAATCGTGGATTTGACAGTTATACAAAAAAACAGGCAGCATT

GGATTTTGGAGATCCACGTGAATTCAAGTCCTATGAAGAAGTTTATAATGCCTTCTA
```

```
CAGACAACTGGAATATGTAGTAAACGTGAAAATTGCAGGAAACAATTTGATTGAAC

GTATGTATATGGAGTATATGCCAGTCCCATTGTTATCTGTTATAACTGATGATTGCA

TCAAATCCGGTATTGACTACAATGCTGGTGGGGCCCGCTATAATACAAGCTATATT

CAATGTGTAGGCATAGCAACTATTACTGACTCACTTGTCTCTATAAAGAAAAATGTA

TTTGAAGATAAGAAATTTTCTATGGATGAGTTATTAAAAGCTTGTAAAGCTGATTTTG

AAGGTTATGATGAAATCTTTGAAACAGTCTATAACAATACTCCAAAGTATGGAAATG

ACGATGATTATGCAGATGATATATTGAGAGATGTTTCAAATTCTCTACAGGATGCTA

TTGCAGGAAGAACTACACCAAAGGGATCAAGGACTGTAGTTGAATTCCTTCCAACA

ACTTGTCATGTATATTTTGGTCAGGTAATGGAAGCCAGCCCTAACGGCCGCCATGC

CGGTGTTCCACTTCCAGATGGTATTTCCCCTGAAAAGGGTGCGGATAGAAATGGC

CCTACTGCCGTAATTAAGTCTGCTTCTAAAATTGACCAGCTGAAGACTGGAGGGGC

ATTGTTGAATCAAAAGTTTACACCGGCAGTTGTTCAAGGTGAAGACGGAGTATCCA

ATTTGGCAGTTTTAATCCGTTCATACTTTGCCATGGATGGTCATCATATACAATTCA

ATGTTGTTGATCGAAAAACTTTGCTTGATGCTCAAAAGCATCCCGAGGAATATGAG

AATTTGATAGTAAGGGTTGCCGGATACAGTGATTATTTTAATAATCTGGATAGAGCC

CTGCAG GATGAAATTATCAACCGTACGGAGCAGGGATTTGCTTGA (pta gene encoding phosphotransacetylase)
>ITRI 04001_pta
                                                SEQ ID NO: 14
ATGAAACAAATATGGGAAAAGGCAAAAACAGATAAAAAGACAATTGT

TTTAGCTGAAGGCGAAGAAGAAAGAAATCTTAAAGCAGGTGAAAAAATAACTAAAA

ATGGTCTTGCCAATGTAATAATGGTTGGAAACATTGATGTAATAAAGGAAAAGGTTA

GCAAGTTGAATGTAGATTTAACTGGTGTTACATTGGTAGATCCACAAACTTCTGATA

AATTAGAAAAATATGCTCATGAGTTTTATGAATTGAGGAAGAAAAAAGGTATTACTC

CTGATAAGGCGAATAAGATAGTTAGAGACCCATTGTACTTTGCAACAATGATGGTC

AAACTAGGAGATGCTGATGGATTGGTATCTGGTTCTATACATACTACAGGCGATCT

TTTGAGACCAGGTCTTCAAATTGTAAAAACTGCTCCAGGAACTTCAGTAGTTTCAAG

CATATTTATGATGGAAGTTCCAAATTGTGATTTAGGTGATAATGGTTFCTTGTTGTTT

TCAGATTGTGCTGTAAATCCTGTACCTAATACTGAACAATTAGCTGCAATAGCTATT

AGTACTGCAGAAACTGCAAAAAGTTTATGTGGTATGGATCCAAAAGTAGCTATGCT

TTCATTTTCAACTAAGGGAAGTGCACAACATGAAAATGTAGATAAGGTAAGAGAAG

CAACCAAACTTGCTAAACAAATGCAACCAGATCTTAAAATAGACGGAGAACTTCAAT

TGGATGCTTCTTTAATACAGGAAGTTGCAAATTTAAAAGCACCTGGTAGTCCTGTAG

CAGGAAAAGCAAATGTACTTATATTCCCTGAACTTCAAGCAGGAAATATTGGATATA

AATTAGTTCAAAGATTTGCAAAAGCGGAAGCAATAGGACCTATATGTCAAGGCTTT

GCAAAACCAATAAATGATTTGTCAAGAGGATGCAGTTCTGACGATATAGTAAATGTA

GTAGCTGTAACAGCAGTACAAGCACAAGCTGCAAAATAA (ack gene encoding acetate kinase)
>ITRI 04001_ack
                                                SEQ ID NO: 15
ATGAAAATATTAGTAATAAATTGTGGAAGTTCATCTTTAAAATATCAA

TTGATAAATATGGAAGATGAAAATGTACTTGCTAAAGGTCTTGTGGAAAGAATAGGT

ATAGAAGGATCCATCCTTACTCATAAAGTAAATGGAGAGAAATATATTACTGAACAG

CCTATGGAAGACCATAAAATAGCTATAAAATTAGTTCTGAATGCACTAGTAGACAAA
```

```
GATTATGGAGTTATTAAAGATATGTCTGAAATATCTGCAGTTGGACATAGAGTTGTA

CATGGTGGAGAAAAATATGCAAATTCAGTTCTAGTAGATGAAGATGTTGTAAAAGCT

ATAAAAGATTGTGCTAAATTGGCACCACTTCATAATGTACCAAATATGATAGGTATA

AATGCATGTAAAGAGTTAATGCCAGATACTCCTATGGTGGCAACATTTGATACTGC

ATTCCATCAAACACTTCCCAATTATGCATATACTTATGCAGTACCATATGATCTATAT

GAAAAATATGGTGTTAGAAAATATGGATTCCACGGTACATCACATAAATTTGTATCA

ATAGAAGCAGCTAAGATGATGGGAAAGGACATAAGATCTCTTAAGATTATAACCTG

CCATTTGGGAAATGGAGCTAGTGTATGTGCAATTGACGGTGGTAAGTCAATAGATA

CTAGTATGGGATTTACTCCACTTGCAGGTCTTTGCATGGGAACTAGATGTGGAGAT

ATAGATCCAGCAGTGATTCCTTTTCTAGTAAAATCAGTGGGAATGTCTATAGATGAA

GTAGATACCTTAATGAATAAAAAATCTGGTGTACTTGGTGTATCAGGAGTAAGCAGT

GATTTTAGAGATGTATTAGCTGAAGAAGCTAAAGGAAATAAGAGAGCGGAACTTGC

TTTGAATGTTTATACTTACAGGGTTAAATCAGTAATAGGCTCTTATATAGCAGCTTTA

AATGGAGTTGATTGCATAGTATTTACAGCTGGATCTGGAGAAAATTCAGAACCTTTG

AGAAGAAGAATATGTGCTGGACTTTCAAATTTAGGTATAGTTTTAGACAAGGAAAGA

AACAATGTTATGGGAAAACCAGCTCAAATAAGTTCAGATGATTCTAAAGTAAAAGTA

TTTGCTATTCCTACTAATGAGGAACTTATGATAGCTAGAGATACAAAAGAAATAGTT

GAAGGTAGATAA (cft gene encoding coenzyme A transferase)
>ITRI 04001_ctf
                                                                SEQ ID NO: 16
ATGAAGTCAAAATTAATGTCTAAGGACAAGGCAGTTAAATTAATAAA

AGATGGAGATACTGTTGCAGTAGGTGGCTTTGTTGGATGTGCACATCCAGAGGATA

TTACATCTGAAATTGAAGAAAATTATATTGAAAATCGTACTCCTAAAAATCTAACATT

GATTTATGCTGCGGGACAAGGTGACAGCGCTGATAGAGGACTGAATCATTTTGGA

CATGAAGGATTAGTCAGTAAAGTAATAGGTGGACATTGGGCATTAAGTCCTAAACT

TCAGAAATTAGCTCTTGACAATAAAATAGAAGCGTATAATCTGCCCCAGGGAATAAT

ATCACAATTGTATAGAGATATTGCTGCTAAAAGGCCGGGAACCATAACCCATGTTG

GATTAAAGACTTTTATAGATCCTAGACTTGAAGGTGGAAAGTTAAATACAATTACTA

AAGAAAACATAGTAGAACTTATAAATATAGGAGGAAAAGAATATTTATTTTATAAAAC

TATACCATTGGATGTTGTAATTTTAAGAGCTACTTATGCTGATGAATTTGGAAATGC

TACTATGGAAAAAGAAGCGGCAATATTAGATGCAACAGCTATGGCTCAAGCTGCAA

AGAACTCAGGAGGTATAGTTATCGTACAAGTTGAACAAGTAGTATCAAAAGGATCT

TTAGATCCTAAAAAAGTAAAGATACCTGGAATATATGTAGATGCTATAGTTGTATCA

CAACCTAAAAATCATATGCAGACTTTTAGTGAAAACTATAATCCATCATATTCTGGA

GAAGCAAGATTTTTAGTGAATTCCATAGTTCCTATGCAACTTAATGAAAGAAAGGTT

ATAGCCAGAAGAGCGGCTATGGAGCTTGTTCCAAATTCTGTAACTAATCTTGGCAT

TGGAATACCAGAAGGAATAGCGACAGTTGCCAATGAAGAAGGCATTGCAGATGAA

ATGACATTGACTATAGAATCAGGTGGTATAGGAGGAGTACCTTCAGGTGGACTGAG

CTTTGGTGCTTCAACTAATCCTCAAAGCATACTTGATCAGGCAAGTCAATTTGACTA

TTACGATGGAGGAGGTGTTGATGTAGCATTYTTAGGGCTTGCTCAGTGTGACAGAG

ATGGTAATATAAATGTAAGCAAATTTGGGCCTAAAATTGCAGGTTGTGGAGGATTTA
```

-continued

TTAATATAAGTCAAAATTCCAAAAAAGTTGTGTACTGTGGAACATTTACAGCAGGTG

GTTTAAAGGTCAAAGTGGAAAACGGAAAACTTAATATAGAAAAGGATGGAAAGTTC

AATAAATTTATAGATACTGTTGAACAGATATCTTTCAGTGGTCAATATGCTCAGAGT

ATTGGACAAACAGTACTTTATATAACTGAAAGAGCAGTATTTAGATTGACAAAAGAA

GGTCTCTTTTTAGAGGAAATAGCTCCAGGTATAGATATGAAAAAGGACATATTGGAT

CATATGGATTTTAGGCCTAAAATATCTGAAAATTTAAAGATAATGGATGAAAGAATA

TTTAAAGAAGAACCAATAGGAATAAATATTGGACAATCATCAAAAGAATTCCCAGGA

GAATTAAGCAATGTATAA (ldh-1 gene encoding lactate dehydrogenase)
>ITRI 04001_ldh-1
                        SEQ ID NO 17
ATGGATGAAGCTAAGTATTTGGATAAGTTTAGTAAAAAATATAATGTT

GAAATTGAATTGTGTAAAGAAGGACCAACTTTGGAAAATGCGAATCTAGCAAGTGG

ATTTAATTGTATAAGTATTATTACAACGCCAGTTGATAGAAATTTAATTAAAAAATTTT

ATGAAGTTGGTGTAAGGTTTATATCTACAAGAACAATTGGATATGATCATATAGATA

TTAAAAGTGCTAGGGAGTTTGGTATTCATGTTGGAAATGTAACATATTCACCAAATA

GCGTAGCTGATTATACCATAATGATGATACTTATGATATCAAGGAAAATCAAAACTA

TTATGGAACGAAGCAATGTACAAGATTATTCTTTAAAGGGAGTTCAAGGAAAAGAAT

TACAAAACTFAACTGTGGGGATTATTGGAACGGGGAGAATTGGAAAAACTGTAATA

AAGCATTTAAGTGGATTTGATTGTAAAATGTTGGCCTATGATATATATAAAGATAAAA

AATTAAATCAATATGTTGAGTATGTTAATCTAAAAGAACTATTTCAAAAAAGCAATAT

TATAACAATGCATGTGCCAGCTACAAAGGATAATTATCATATAATAGATAAGAATTC

TATAACATTGATGAAAGAAGGAGTATTTATTATTAATACAGCCAGAGGATCTTTAAT

AAATACCGATGATTTAATTGATGGTATAGAAAAGAAAAAAATTGGTGGGGTAGCTTT

GGATGTTATAGAAAATGAATCAAATATATATTATAATGATCTAAAATGTCAGGTACTT

GATAATAGGGATTTGGCAATACTTAAGTCATATCCTAATGTTATTGTTACACCTCAT

ACGGCTTTTTATACTGATCAGGCTGTAAGTGATATGGTTGAAAATTCTATTTTAAGTT

GTATTTTATTTGTTGAGAAAAAAGAAAATCCATGGGAAGTTTGTTAA (ldh-2 gene encoding lactate dehydrogenase)
>ITRI 04001_ldh-2
                        SEQ ID NO: 18
ATGAAAATTAGAGGTATAAAAATATCCATAATTGGTGCTGGTTTTGTA

GGTTCGACTACTGCTTTCTCAATTATGAGTTCTGGCTTGGCTTCAGAAATAGTAATC

GTAGATGTAAATAAAGATAAGGCTGAAGGAGAAGCAATGGATCTAGCTCACGGAGT

GTCATTTGTAAAACCTGTTGATATAAAATCTGGCGATTACAAGGATACAGAAGAATC

GAATATTGTTATAATAACAGCAGGTTCCGGTCAAAAACCTGGTGAAAGCAGATTGG

ATTTAATTAATAGAAATTATTCTATCTTTAAATCCATAGTACCTGAAGTTGTAAAATA

CAGCCCTAAATCTATACTTTTGGTAGTTTCAAATCCCGTGGATATACTGACTTACAT

AACCTATAAATTATCTGGATTTCCACCTGAAAGAATAATAGGTTCTGGTACCGTTCT

AGACACCTCAAGACTCAGATATATGATAAGTGAAAATTTCAATATAGATGCAAGAAA

TATTCACAGCTATATAATAGGAGAACATGGAGATTCTGAAATAGCTACATGGAGTTC

TACTTCTATTGCCGGAATACCTCTAGAACAATATTGCAATTTGATGGATGCCAGTTG

CGATTCGGATTATCAGGATAGGATAATAAATAATGTAAGAAATGCAGCTTATGAGGT

-continued

AATAGAACGAAAGGGATCAACTTATTTTGCTGTTGCTCTAGCCGTTAGACGAATTGT

AGAAGCACTGTCAAGAGATGAAAATTCAATAATGACAGTTTCTGCACTATTTAGTGG

TGAATACGATGTAGATAATGTTTACATGGGCCTTCCTGCAGTAATAGGATCTGAAG

GAATTCAAAAAACCCTCCGTGTTCCACTAAACAGTGTAGAAAAAACAGCTTTGCAAA

CTTCAGCTGATACACTAAAAGATATAATTGAAAAGTTAAATATTTAA (ldh-3 gene encoding lactate dehydrogenase)
>ITRI 04001_ldh-3
SEQ ID NO: 19

ATGATACAATTAAATATATGTATAGCTATACATAAAAAAGGAGGCAG

CATTATTATGAATTCTATAAATAATAAACTTGTAATAGTTGGAGTGGGAAATGTAGG

TACTGCTGTATTGAATACTGCATTATCTT1TGGATTTGCTTCAGAAATTGCACTAATT

GATATAGATAATGACAAGGCAAGAGGTGAAGCATTGGACTCAAGTCATACTACACC

TTGTACATATAGTGTCAATGTGGACATACATGAGGGAAACTATGAAGATTGCAAAG

ATGCCAATGTTATTATTATAGCTGCAGGTCCAAGTATATTGAAAGATGATAAAAATG

ATGATAGAACAGTTCTTGCAGAAAGAAATGTAAAAGTAATGAAAGATGTAATGGGTT

CTATAAGCAAGTATACAAAGGATGCAATAATAATrATAATAACAAATCCATTGGACA

CAATGGTATATTATGCTGAAAATTTCTTTGGATATCCCAAAGAAAAGTATTTGGAA

CAGGTACAAGTCTTGATTCAGCCCGTTTTAGAAAGATCATAGCAAATAGATACAATC

TTGACCCTAAGGATGTTCATGGTTATATGTTTGGTGAACATGGTAATACTGCATTTC

CAGTATGGAGCCATTTGAATGTTGAGGGAGTTTCAGCAGATGAGCTTGATAAATTT

TTTCCTCATGACAAACCATTGGATAAGGAAGAAATAGCTTCAGATGTAGTAAAGGTT

GCCTATGATGTACTTCATTTGAAAGGGTGTACAAATTCGGGCGTTGCTATGGCGGC

CTGCAGAATTGCCAGGGCAGTATTTATGGATGAACATAGTATATTGCCTGTTTCCA

CTACTCTTGAAGGAGAATATGGATTAAAAAATGTAGCACTCAGTTTGCCATGTATTA

TAGGAAAAAATGGAGTTGAAAGAAGGCTTGAAGTTTCTCTTACTGATGAAGAAAAT

GACAAACTTTATAACAGTGCAAAAAATATTTTGGCTACAATGAAAGCTGCAGGATTA

ATAGAAGATAAATAA (dldh gene encoding D-lactate dehydrogenase)
>ITRI 04001_dldh
SEQ ID NO: 20

ATGGATTTTGAAAAATTATCTGATATTATAAAGACGAAAATAGGATA

AAGATAGGGACAGATATAGAGGACAAATATTTAAGTGATGCACTAAATAGGAATAA

AGGTAAAGCTGATGTATTGATATTTCCTATAAATACAGAAGAAGTAAGCAGCATAAT

GAAAATAGCATATGAAAATGGCATACCTGTTACACCAAGAGGAGCCGGTACAGGAT

TGGTAGGTGCAACTATTCCTACCAGGGGAGGTATTATATTAGATCTATCCTTAATGA

AAAATATAGTTGAGTTAGATGAAAATACTCTTACAGTAACTGTGCAGCCGGGAATTT

TACTTGTAGATCTTCAAAAATTTGTTGAAAGCAAGGGATTTTTCTATCCTCCAGATC

CAGGAGAAAAAATGCTTCAATAGGTGGAAACATAAGTACTAATGCCGGCGGAATG

AGAGCTGTAAAGTATGGAGTTACAAGAGACTATGTTATGGGTTGGAAGTAGTTTT

AGCCGATGGAACCATACTAAATACAGGTGGAAAAGTAATAAAGAATAGTTCTGGAC

TTGATATAAAGGACTTAATAATAGGATCAGAAGGTACTCTTGCAATTATAACCAGGG

CAATATTAAAACTTATACCAAAACCTAAAAAGAGTATAAGCGCTATTATTCCATTTAA

CTCTTAAAAGAAGGAATAGATACAGTCATAAAAATAATAAAAAAGAATGCCAATCC

TACAGCTATTGAATTTATGGAAAGTGATGTCATTGAAAATGCAGAAAGATTTTTAAA

```
GTTAAAATTTCCTTCTGATAGGGGAAAGGCATATTTATTATTGACATTTGATGGAGA

TGAAGAATTTGAAATAGAGAGTAATTACAAAAAAGTAAAAGAAGTTGCTTGGGAAA

TAATGCCCTGGATTTTATTTTGCTTGATAAAAAGGATGACATAGAGAGAACCTGGAA

AATAAGGGGAGCTTTGGTTACGGCAGTAGAAGCTGTATCTGAACAGGAGCCTATA

GATATAGTAGTTCCAATAGACAGATCAGCAGATTTTATTAATTATACAAAAGTAGCA

GAAAAGGAATTTGGAATTAAGATAAGTAGCTTTGGTCATGCTGGCGATGGAAATGT

ACACTTATGTGTAATTAGAAATGGCATGGAAGAAAATCTATGGAATGAAAAATCGAG

AAAACTACTTAAAGCTCTTTATAGAAAAGGGAAAGAACTTAATGGACTGCCATCTGG

AGAGCATGGCATAGGAATTAACAAGAAACCATATTTTATTGATGTAACAGATAAGAT

AAATGTAGAGTATATGAGAAGAATAAAAAAAGCCTTTGATGAAAAGGGAATTTTAAA

TTCCGGTAAATCATATTCAATATGA (pct-1 gene encoding propionate CoA transferase)
>ITRI 04001_pct-1
                                                SEQ ID NO: 21
ATGAAGTCAAAATTAATGTCTAAGGACAAGGCAGTTAAATTAATAAA

AGATGGAGATACTGTTGCAGTAGGTGGCTTTGTTGGATGTGCACATCCAGAGGATA

TTACATCTGAAATTGAAGAAAATTATATTGAAAATCGTACTCCTAAAAATCTAACATT

GATTTATGCTGCGGGACAAGGTGACAGCGCTGATAGAGGACTGAATCATTTTGGA

CATGAAGGATTAGTCAGTAAAGTAATAGGTGGACATTGGGCATTAAGTCCTAAACT

TCAGAAATTAGCTCTTGACAATAAAATAGAAGCGTATAATCTGCCCCAGGGAATAAT

ATCACAATTGTATAGAGATATTGCTGCTAAAAGGCCGGGAACCATAACCCATGTTG

GATTAAAGACTTTTATAGATCCTAGACTTGAAGGTGGAAAGTTAAATACAATTACTA

AGAAAACATAGTAGAACTTATAAATATAGGAGGAAAAGAATATTTATTTTATAAAAC

TATACCATTGGATGTTGTAATTTTAAGAGCTACTTATGCTGATGAATTTGGAAATGC

TACTATGGAAAAAGAAGCGGCAATATTAGATGCAACAGCTATGGCTCAAGCTGCAA

AGAACTCAGGAGGTATAGTTATCGTACAAGTTGAACAAGTAGTATCAAAAGGATCT

TTAGATCCTAAAAAAGTAAAGATACCTGGAATATATGTAGATGCTATAGTTGTATCA

CAACCTAAAAATCATATGCAGACTTTTAGTGAAAACTATAATCCATCATATTCTGGA

GAAGCAAGATTTTTAGTGAATTCCATAGTTCCTATGCAACTTAATGAAAGAAAGGTT

ATAGCCAGAAGAGCGGCTATGGAGCTTGTTCCAAATTCTGTAACTAATCTTGGCAT

TGGAATACCAGAAGGAATAGCGACAGTTGCCAATGAAGAAGGCATTGCAGATGAA

ATGACATTGACTATAGAATCAGGTGGTATAGGAGGAGTACCTTCAGGTGGACTGAG

CTTTGGTGCTTCAACTAATCCTCAAAGCATACTTGATCAGGCAAGTCAATTTGACTA

TTACGATGGAGGAGGTCTTGATGTAGCATTTTTAGGGCTTGCTCAGTGTGACAGAG

ATGGTAATATAAATGTAAGCAAATTTGGGCCTAAAATTGCAGGTTGTGGAGGATTTA

TTAATATAAGTCAAAATTCCAAAAAAGTTGTGTACTGTGGAACATTTACAGCAGGTG

GTTTAAAGGTCAAAGTGGAAAACGGAAAACTTAATATAGAAAAGGATGGAAAGTTC

AATAAATTTATAGATACTGTTGAACAGATATCTTTCAGTGGTCAATATGCTCAGAGT
```

-continued

ATTGGACAAACAGTACTTTATATAACTGAAAGAGCAGTATTTAGATTGACAAAAGAA

GGTCTCTTTTTAGAGGAAATAGCTCCAGGTATAGATATGAAAAAGGACATATTGGAT

CATATGGATTTTAGGCCTAAAATATCTGAAAATTTAAAGATAATGGATGAAAGAATA

TTTAAAGAAGAACCAATAGGAATAAATATTGGACAATCATCAAAAGAATTCCCAGGA

GAATTAAGCAATGTATAA (pct-2 gene encoding propionate CoA transferase)
>ITRI 04001_pot-2
SEQ ID NO: 22
ATGGGAGTAAAGTTTTTAAAGGCTTGTGATGCTGTAGAAATGGTTAA

AGATGGAGACTTGATCGCAACAAGCGGTTTTGTAGGTAGTCTTTGTTCAGAAGAAC

TTAGTATAGCTTTAGAAAAACGTTTTGAAGAGACAGGACATCCAAAAAATTTAACAT

TAGTATATTCTGCAGCTCAAGGAGATGGAAAGGGAAAAGGAGCAGATCATTTTGCA

CATGAAGGAATGTTAAAAAGAGTTGCAGGTGGACATTGGAATTTATCACCTAAATT

GGGCAAAATGGCAGTAGAAATAAAATTGAAGCATATAATCTTCCACAAGGAACAA

TTGCACAATTATTTAGAGATATTGCAGGAAAAAGAATTGGAACCATAACTCATGTTG

GATTAAATACCTTTGTAGATCCAAGAATTCAAGGTGGAAAGTTAAATGATATAACAA

AGAAGATGTAGTAAAACTTATAAATATTGAGGGTCAGGAAAAATTACTTTATAAAG

CTTTCCCTATTGATGTATGTTTTTGAGAGGATCTTTTGCAGATGAAAATGGTAATAT

ATCACTTGAAAGAGAAGTAGGTACTATAGATGTACTTTCTATAGCTCAAGCTTGTAG

AAATAGCGGTGGGACTGTAATTGTACAAGTCGAAAAGGTAGTTTCTTCAGGTACTT

TGGATCCAAGACTTGTGAAGATACCAGGTATATATGTTGATGTAGTGGTTGTTGCC

AAACCTGAACATCATGAGCAGTTTTTTGGTTGTAATGGTTATGATCCTTCATTAACT

GGTGAAGTGAGAGTTCCTTTAAAAGCTATACAATATCCTGAATTAAATGCAAGAAAA

ATAATAGCTAGAAGAGCTGCTATGGAACTCAAACCGGATGCAGTAGTAAATTTAGG

TATAGGAATACCTGAAGTTATATCAATGGTTGCAAATGAAGAAGGAATTGGAGAATA

TATGACTATGACAGTAGAAGCTGGAGCTGTAGGAGGAGTGCCTCTTGGCGGAACT

GGTTTTGGTGCATGCATAAATCCTGAATCAATCTTGGACGAGGCTTATCAATTTGAT

TTTTATGATGGCGGTGGAACTGATATAGCATTTTTAGGATTGGCCCAAGTTGACAA

AAACGGGAACATAAATGTAAGTAAATTTGGACCTCGTATAGCTGGATGCGGTGGCT

TTATAAATATAACTCAAATGCTAAAAGGGTATTGTTCTGTGGTACATTTACAGCTG

GAGGACTAAAAATAGACACAGGCGATGGAAAATTAAACATAATTCAAGAAGGAAGA

GCAATAAAATTTTTAAAACAAGTTGAACAGATAACCTTCAGTGGAGAATATGCTATT

AAAACAAAGCAGCCAGTTACTTATATAACTGAAAGGGCAGTATTTGAACTTAAAGAA

GATGGACTATATATTACAGAGATAGCTCCAGGTGTTGATATTGAAA (thl gene encoding thiolase)
>ITRI 04001_thl
SEQ ID NO: 23
ATGAGTGAAGTTGTAATTGCAAGTGCCGTTAGAACAGCAATAGGTAA

ATTTGGAGGTAGCTTGAAGTCAGTTCCAGCAACTGATTTAGGAGCTTTGGTTATAA

AAGAAGCATTAAAAAGAGCTAATGTTAAACCAGAACTTGTAGATGAAGTTGTAATGG

GTAATGTATTACAGGCAGGTTTAGGTCAGAATCCAGCAAGACAAGCATTGATAAAA

TCAGGTATACCTAATACAGTCCCTGGATTTACTATAAATAAAGTTTGTGGTTCAGGA

CTTAGAGCAGTAAGTTTAGCAGCTCAAATGATAAAAGCTGGCGATGATGATATCGT

-continued

```
TGTAGCTGGTGGAATGGAAAATATGTCTGCTGCTCCATATGTAATGCCTAGTGCAA

GATGGGGACAAAGAATGTTTGATGGTAAGATTATAGATGAAATGGTAAAAGACGGA

CTTTGGGATGCTTTTAATAACTATCACATGGGTATTACGGCTGAAAATATAGCAGAA

AAGTGGAACATAACAAGACAAATGCAGGATGAATTTGCAGCTGCATCACAACAAA

AGCAGTAGCAGCTATAAAATCTGGCAAGTTTAAAGATGAAATAGTTCCAGTAGTAAT

CAAGGATAGAAAAAGGGAGAAATAGTATTTGATACTGATGAATTCCCTAGAGATG

GTGTAACTGTCGAAGGAATATCAAAATTAAAACCAGCATTTAAGAAGGATGGTGGA

ACTGTTACAGCTGCCAATGCTTCAGGTATAAATGATGCAGCTGCAGCATTAGTTAT

AATGAGTGCAGACAAAGCAAAAGAATTGGGAATTAAACCACTTGCTAAAATTACTTC

TTATGGATCAAAAGGCTTGGATCCTAGCATAATGGGATATGGACCATTCCATGCTA

CAAAACTAGCACTTAAAAAAGCTAATTTAACTGTAGATGATTTAGATTTAATAGAAG

CAAACGAAGCATTTGCTGCTCAGAGTTTAGCTGTTGCAAAAGACTTGAAATTTGATA

TGAGCAAAGTAAATGTAAATGGAGGAGCAATAGCACTTGGACATCCTATTGGAGCT

TCAGGCGCAAGAATACTTACTACTTTGCTTTATGAAATGCAGAAAAGAGATTCAAAA

CGTGGTTTAGCTACATTATGTATAGGCGGTGGAATGGGAACTGCTATAATCGTTGA

AAGATAA
```

(hbd-1 gene encoding 3-hydroxybutyryl-CoA dehydrogenase)
>ITRI 04001_hbd-1
SEQ ID NO: 24
```
ATGAATATAAAAAGTATATCAGTTTTAGGTACTGGAACTATGGGACA

TGGCATAGCATTATTTTCGTCAATGGCTGGTTTAAATGTAACTATGTACGGTAGGTC

AGATGCAAGTCTTAAAAGAGGATTTAGTGCTATAAAAGAGGACTTAGGACGATTAG

AATCACAAGGAGAATTAGATGATGGTACTTGTAAAAGTATATTAGATAGAATAAAAG

GGGTCAAAACTATTGAAGAAGCCTCTAAAGGAACAGATTTTGTAATAGAGTCTTTAG

CCGAAGACTTGCAGATCAAAAGAAAATTTTTTGAAAAGTTGGATGCTCTTTGTAAAT

ACGATGTTATTCTTGCTACAAACACTTCAGGACTTAGTCCTACAAAAATAGGGGAA

GTTACAAAACATCCAGAGAGAGTAGTGGTAGCTCACTTTTGGAACCCACCTCAATT

AATTCCATTAGTAGAAATAGTACCTGGGGAAAAAACTTCTAAGGATACTGTATTAAA

GACAAAGGAATTAATTGAATTTATAGGGAAGAAAGCTGTTTGTATGGAAAAAGAGT

GTGCTGGTTTTATAGGAAATAGATTACAGCTTGCACTTCTAAGAGAGGCTATGTATA

TAGTAGAGCAAGGATGGGCAAAACCAGAAGAAGTAGACAAGGCTATGGAATATGG

ACATGGTCGAAGACTTCCAGTTACAGGACCATTAAGCAGTGCAGATCTAGGGGGA

CTGGATATATTTTACAATATATCATCTTATTTATTTAAAGATCTGTGTGATTATAAAAA

GCCATTTGAATTAATGAAAGAAAAGATTGAAAAAGGTGATTTAGGAAGTAAAAGTG

GAAAAGGATTTTATAATTGGTCTAAAGGGGATTTAGAAAAAAAACAAAAAGAACGAA

CAGACCTACTTTTATATTTCTTAAAAAAGGATGCCAATTAA
```

(hbd-2 gene encoding 3-hydroxybutyryl-CoA dehydrogenase)
>ITRI 04001_hbd-2
SEQ ID NO: 25
```
ATGAAAAAAATATGTGTTCTTGGTGCAGGTACAATGGGTTCTGGAAT

AGCTCAGGCTTTTGCAGCTAAAGGTTGTGAAGTATTAATAAGAGATATTAAAGATGA

ATTCGTTGATAGAGGACTTGCAGGAATTAAAAAAGGATTTGACAAGAGAATAGCAA

AGGGTAAAATGGTACAGGCAGATGCTGATGCAATACTTGCTAGAATAAGTGGAACA

GTTGACCTAGAAAAGGCAGCTGATTGCGATCTAGTAATAGAAGCAGCAGTTGAAAA
```

```
TATGGAGATAAAGAAGCAAATATTTGGTGACTTGGATAAAATATGTAAGCCTGAAAC

AATTTTAGCTTCTAATACTTCTTCATTGTCAATAACTGAAATAGCATCTGCTACAAAA

AGACAGGATAAAGTTATAGGAATGCATTTCTTTAATCCAGCACCTGTAATGAAATTA

GTTGAGATAATAAGAGGAATGGCTACTTCACAAGAAACTTTTGATGCAGTAAAAGA

AGTTTCAATTGCCATAGGCAAGGATCCAGTAGAGGTGGCAGAAGCTCCAGGATTT

GTTGTAAATAGAATATTAATACCAATGATAAATGAAGCCGTAGGAATTTTTGCGGAA

GGAATAGCTTCAGCAGAGGATATTGATAAAGCTATGAAACTTGGTGCTAATCATCC

AATGGGACCACTAGCATTAGGAGATCTTATTGGACTGGATGTATGTCTTGCAATFAT

GGATGTACTTTATAAAGAAACAGGGGATTCCAAATACAGAGCTCACTCGCTACTTA

GAAAATATGTAAGAGCAGGATGGCTTGGAAGAAAGAGCAAAAAAGGATTCTTTGAT

TATTCAAAATAA (crt-1 gene encoding 3-hydroxybutyryl-CoA dehydratase)
>ITRI 04001_crt-1
                                               SEQ ID NO: 26
ATGGAAAATGTTATTTTAAAAGAAGAGAATGGTATTGCAGAAGTTATT

ATTAATAGACCTAAAGCACTTAATGCGTTGAATAGTGAAACACTAAAAGAACTTGGA

AACGTAATCGATGGCATAAATGTAAACGATAATATTAAGGCGGTAATATTAACAGGT

TCAGGTGAAAAATCATTTGTAGCAGGAGCTGACATAGCACAAATGAGTAAACTGAA

TTCAATAGAAGCAACAAANTTCTCAAGACTTGCACAAAATGTGTTTTCACAAATAGA

AGATCTTCCTAAATTAGTAATAGCTGCAGTCAATGGATTTGCTCTTGGAGGAGGTT

GTGAACTTGCCATGGCATGTGATATAAGATTTGCTTCGAAGAAAGCTAAATTTGGA

CAACCAGAAGTTAATTTAGGTATACTGCCAAGTTTTGGAGGCACACAAAGACTTCC

AAGATTAGTTGGAAAAGGAATAGCAAAAGAATTAATTTTTTCTGCAGATATGATTAG

TGCTGATGAAGCTTATCGTATAGGACTTGTCAATAAAGTTTATGAACCTGATGAGCT

ACTTTCAAAGTCAAAAGAATTTGCACAAAAGGTAATGACTAAATCTCCATGGGGTGT

TAAATTGGCAAAAGCATCAATAAATAATGGATTGGATGTTGACTTGGAAGCTGGAC

TTAAATATGAAGCAAATTCTTTTGGATTATGTTTCTCAACTGAAGATCAAAAAGAGG

GTATGAAAGCCTTTTTGGAAAAGAGAAAAGCTAATTTTAAAGATTGTTAA (crt-2 gene encoding 3-hydroxybutyryl-CoA dehydratase)
>ITRI 04001_crt-2
                                               SEQ ID NO: 27
ATGAGTTTTAAAAATGTTAATTTTGAGAAAGATGGAAAGATGGTTGTA

ATTACAATTAATAGACCTAAGGCACTTAATGCACTTAACTCGGAAACATTAGTTGAA

ATTGATTCGGCAATCGATATGGTAGCTGAAGATGAAGATGTTTTAGCTGTAATACTT

ACAGGTGCTGGAAAGTCTTTTGTAGCTGGTGCAGATATATCAGAAATGAAAGGTCT

CAATGCTATTGAAGGAAGAAAATTTGGAATATTGGGCAACAAGGTTTTTAGAAAGTT

GGAAAAATTGGAAAAGCCTGTTATTGCAGCAGTTAATGGTTTTGCATTAGGCGGTG

GTTGTGAAATTTCCATGGCATGTGATATAAGAATAGCTTCATCAAAAGCTAAATTCG

GACAACCAGAGTCAGGACTTGGTATTACCCCAGGTTTTGGGGGAACTCAAAGACTT

CCAAGATTAGTAGGACTTGGAATGGCAAAAGAACTTATATACACTGCCAAAATTATA

AAAGCGGATGAAGCATTTAGAATAGGACTTGTAAATAAAGTAGTAGAACCTGAAGC

ACTTATGGATGAAGCTAAAGCATTAGCTAATACAATAATTAACAATGCACCAATAGC

TGTAAAGTTATGTAAAGAGGCAATAAATAGAGGAATACAGACAGATATAGATACTG
```

-continued

GAGCAGCATACGAATCTGAAGTATTTGGGGAATGCTTTGCTACAGAGGATCAAAAA

GAAGGTATGGGTGCGTTTCTCGAAAAAAGAGATAAAACTTTTAAAAATAAATAA (bcd gene encoding butyryl-CoA dehydrogenase)
>ITRI 04001_bcd
SEQ ID NO: 28
ATGGTAAGGGAATTTACAGAAAATGAAGTTAAACCTCTAGCGGCAG

AGATAGATGAGACTGAGAGATTCCCTAAAGAAACTGTAGAAAAAATGGCTAAATAT

GGAATGATGGGTATACCTTTCCCAGTAAAATATGGTGGAGCAGGTGGAGACACTCT

ATCCTATATATTAGCAGTAGAAGAACTTTCCAAGGCTTGTGGAACAACGGGTGTTA

TACTTTCAGCTCATACATCACTTTGTGCATCACTTCTTGAACAGTTTGGAACGGAAG

AGCAAAAACAAAAATATCTGGTACCACTTGCAAAGGGAGAAAAACTTGGAGCATTT

GGATTAACTGAACCTAATGCTGGTACTGATGCTTCAGGACAACAAAGCTTGGCTGT

ACTAGAAGGAGATCATTATATATTAAATGGTCAAAAAATATTTATAACAAATGGTGG

AGCAGCAGATATATTTGTAGTATTTGCAATGACTGATAGAAGCAAGGGTACAAGAG

GAATATCAGCATTTATACTTGAAAAGGGTATGAAAGGTTTTTCGATTGGAAAGCTTG

AAAATAAAATGGGTATAAGAGCGTCATCAACTACTGAACTTATATTTGAAGATTGTA

TAGTTCCAAAAGAGAATTTGGTAGGAAGAGAAGGAAAAGGCTTTGGTATAGCAATG

AAAACTCTTGATGGAGGAAGAATTGGTATAGCAGCCCAGGCTCTAGGTATAGCAGA

AGGAGCTTTGGAGGAAGCCGTTGAATATATGAAAGAAAGAAAACAATTTGGAAGAT

CACTTTCCAAATTCCAGGGATTAGGCTGGGTCGTTGCTGATCTTGCAACCAAAATA

GATGCGGCAAGATATCTTGTTTACAAAGCGGCATTAAATAAAGATGCACATGTCCC

TTATACAGTAGATGCGGCAAAGGCTAAATTAATGGCAGCAGATGTTGCTATGGAAA

CTACAACTAAGGTTGTTCAATTGTTTGGTGGATATGGATATACCAAGGATTATCCAG

TAGAGAGAATGATGAGAGATGCAAAGATAACTGAGATATATGAGGGAACTTCTGAG

GTACAAAGAATGGTTATTTCCGGAAGCATATTTAGATAG (ptb gene encoding phosphate butyryltransferase)
>ITRI 04001_ptb
SEQ ID NO: 29
ATGAATAAAAAAATCAAATGGTTGCTTGTATTTTTATGGATGATTTTA

ATATTTTCCTTTTCAAGTCAATCAGGAGTTGCATCTGATGAAAAAAGTAGATTTATTG

TATATCTATTTAATGAGTCAGGAATAAATCTTAATAGTGTATTTGGAAATCTAGCAAA

TTTTGCAGTAAGGAAATTTTCTCATTTCACAGAGTATTTTATATTATATATATTGTTGT

TTAACGCACTATATGAGAAATCTAAAATGAAGAAGACTTTTTTATTGTCAATAGTAAT

AGTATTTTTATATGCATGTTCTGATGAAATACATCAGTTTTTTGTTCCAGGCAGATCT

TCAAGAATAAGGGATGTTATAATAGATACTTCCGGAGGTTTTGCATCACTTTTATGT

TGTTTGTTTCACAGTCGTAGAAAGAATAAATATAGGAGAGATTTATAG (bdhA gene encoding NADH-dependent butanol dehydrogenase)
>ITRI 04001_bdhA
SEQ ID NO: 30
TTGATTAACTTTAATTATTCAATTCCAACAGAGATTTTCTTTGGAAAGGGCAGCATAA

GTATTCTAGGAAAACAATTAAAAAGATATGGCGCTAAAGTACTTGTTGTATATGGTG

GAGGAAGTATAAAGAAAATGGAATATATGATTTGGCAATTAAACTTATAAAGGAAA

GTAAAATAAAATTTTGGGAATTGTCAGGTGTAGAGCCCAATCCTAAAATATCCAGTG

TAAGACAAGGTGTAAAAATATGCAGGGACAACAGGATAGATTGTATACTGGCAATA

GGAGGAGGCAGTGTAATTGACTGTTCTAAAGCTATAGCGGCAGGCTATTATTATGG

-continued

```
AGGAGATCCATGGGATATTGTAACAGACCCTTCAAAAATAAAGAAAGCACTTCCTG

TTGCGAGTATTTTAACATTAGCAGCTACAGGATCGGAAATGGACATATTTGCTGTTA

TTACAAATGAAGAAACCAAGGAAAAGTTAGGTACAAAAAGCTCATATATGGCTCCA

AGGTTTTCCATACTTGATCCCACTTATACTTTTACAGTATCAAAAAATCAGACAGCA

GCAGGAACAGCAGATATAATGAGTCATATTATGGAAAACTATTTTAATAATACAGAA

GGTGCCTATGTTCAGGACAGATTAGCAGAGGCACTCTTAAAGACATGTATAAAATA

TGGCCCTATAGCTCTTGAAAAACCTGATGATTATGATGCAAGAGCCAATTTAATGTG

GACTTCAAGTCTTGCGATAAATGGACTTCTGGATTATGGCAAGGTAAAAGGTTGGA

GTGTCCATGGCATGGAACATGAATTAAGTGCATTTTATGATATTACCCATGGTGTG

GGATTGGCTATATTAACACCCTATTGGATGGAATATGTATTAGATAATAATACAGTA

GACAAATTTGTGGAATATGGAATAAATATATGGTCTATAGATAAAAATAAAGATAAAT

TTACGATAGCACATGAGTCAATAGAGAAAACACGCGAATTCTTTAATTCATTGGGAC

TTCCTGCCAGACTTAAAGAAGTAGGCATTGATGAAGAGAATTTTGAAAAAATGGCT

GAAGGAGCTACAAGACATGGAAAACTGGGAGAATTCAAGCCGCTTTCAAAACAAG

ATGTCATAAATATATATAAGTCAGCATTATAA
```

---

What is claimed is:

1. An isolated biologically pure culture of *Clostridium tyrobutyricum* ITRI04001 (DSM 27751).

2. An isolated biologically pure culture of *Clostridium tyrobutyricum* having the genotypic characteristics of *Clostridium tyrobutyricum* ITRI04001 (DSM 27751).

3. A process for producing volatile free acid comprising:
culturing a microorganism having the genotypic characteristics of *Clostridium tyrobutyricum* ITRI04001 (DSM 27751) in a medium;
providing at least one substrate comprising at least one carbon source chosen from CO and $CO_2$ to the microorganism; and
recovering at least one free volatile free acid.

4. The process for producing volatile free acid according to claim 3, wherein the microorganism is ITRI04001 (DSM 27751).

5. The process for producing volatile free acid according to claim 3, wherein the medium comprises at least one carbohydrate chosen from glucose, xylose, fructose, lactate, and acetate.

6. The process for producing volatile free acid according to claim 3, wherein the medium does not comprise glucose, xylose, fructose, lactate, or acetate.

7. The process for producing volatile free acid according to claim 3, wherein the at least one substrate further comprises at least one gas chosen from $N_2$ and $H_2$.

8. The process for producing volatile free acid according to claim 3, wherein the at least one substrate is a syngas.

9. The process for producing volatile free acid according to claim 3, wherein the at least one substrate comprises CO.

10. The process for producing volatile free acid according to claim 3, wherein the at least one substrate comprises $CO_2$ and further comprises $H_2$.

11. The process for producing volatile free acid according to claim 3, wherein the at least one substrate comprises $CO_2$ and CO and further comprises $H_2$.

12. The process for producing volatile free acid according to claim 3, wherein the at least one volatile free acid is chosen from formic acid, acetic acid, lactic acid, propanoic acid, and butyric acid.

13. A composition comprising *Clostridium tyrobutyricum* ITRI04001 (DSM 27751), a medium, and at least one substrate comprising at least one carbon source chosen from CO and $CO_2$.

14. A composition according to claim 13, wherein the at least one substrate comprises CO.

15. A composition according to claim 13, wherein the at least one substrate comprises $CO_2$ and further comprises $H_2$.

16. A composition according to claim 13, wherein the at least one substrate comprises $CO_2$, and CO and further comprises $H_2$.

17. An isolated biologically pure culture of *Clostridium tyrobutyricum* ITRI04001 (DSM 27751) comprising SEQ ID NOs 1 through 30.

* * * * *

SEQUENCE LISTING

<160> NUMBER OF SEQ ID NOS: 36

<210> SEQ ID NO 1
<211> LENGTH: 1514
<212> TYPE: DNA
<213> ORGANISM: Clostridium tyrobutyricum

<400> SEQUENCE: 1

```
ttttaaattg agagtttgat cctggctcag gacgaacgct ggcggcgtgc ctaacacatg      60
caagtcgagc gatgaaaccc cttcgggggt ggattagcgg cggacgggtg agtaacacgt     120
gggtaacctg cctcaaagtg ggggatagcc ttccgaaagg aagattaata ccgcataaag     180
ccaagtttca catggaattt ggatgaaagg agtaattcgc tttgagatgg acccgcggcg     240
cattagttag ttggtggggt aatggcctac caagacagcg atgcgtagcc gacctgagag     300
ggtgatcggc cacattggaa ctgagatacg gtccagactc ctacgggagg cagcagtggg     360
gaatattgca caatgggcga aagcctgatg cagcaacgcc gcgtgagtga tgaaggtctt     420
cggattgtaa agctctgtct tttgggacga taatgacggt accaaaggag gaagccacgg     480
ctaactacgt gccagcagcc gcggtaatac gtaggtggcg agcgttgtcc ggatttactg     540
ggcgtaaagg gtgcgtaggc ggatgtttaa gtgagatgtg aaatacccgg cttaacttg      600 ggtgctgcat ttcaaactgg atatctgag tgcaggagag gagaatggaa ttcctagtgt     660
agcggtgaaa tgcgtagaga ttaggaagaa caccagtggc gaaggcgatt ctctggactg     720
taactgacgc tgaggcacga aagcgtgggt agcaaacagg attagatacc ctggtagtcc     780
acgccgtaaa cgatgagtac taggtgtagg aggtatcgac cccttctgtg ccgcagtaaa     840
cacattaagt actccgcctg ggaagtacga tcgcaagatt aaaactcaaa ggaattgacg     900
ggggcccgca caagcagcgg agcatgtggt ttaattcgaa gcaacgcgaa gaaccttacc     960
tggacttgac atcccctgaa taacctagag ataggcgaag cccttcgggg cagggagaca    1020
ggtggtgcat ggttgtcgtc agctcgtgtc gtgagatgtt aggttaagtc ctgcaacgag    1080
```

```
cgcaacccctt attgttagtt gctaacattc agttgagcac tctaacgaga ctgccgcggt    1140
taacgcggag gaaggtgggg atgacgtcaa atcatcatgc cccttatgtc cagggcaaca    1200
cacgtgctac aatgggcaga acaaagagaa gcaataccgc gaggtggagc caaactcaaa    1260
aactgctctc agttcggatt gcaggctgaa actcgcctgc atgaagctgg agttgctagt    1320
aatcgcgaat cagcatgtcg cggtgaatac gttcccgggc cttgtacaca ccgcccgtca    1380
caccatgaga gctggcaaca cccgaagtcc gtagtctaac gtaagaggac gcggccgaag    1440
gtggggttag tgattggggt gaagtcgtaa caaggtagcc gtaggagaac ctgcggctgg    1500
atcacctcct ttct                                                     1514
```

<210> SEQ ID NO 2
<211> LENGTH: 1887
<212> TYPE: DNA
<213> ORGANISM: Clostridium tyrobutyricum

<400> SEQUENCE: 2

```
atggaaaatt gtaaaagttg tagtatttgt aattcggcag acaaggtatt ggaagatttc      60
attgaaacat tggatataga gacttctctt catcgtgtag agagtcagaa gtataaatgc     120
aactttggga aaaatggtgt atgctgtaaa ctctgtgcaa atggtccctg tagaataagt     180
gagaaatctc ctagaggaat atgcggagca actgccgata caatagttgc aagaaatttt     240
ttaagggctg tagcagcagg tactgcatgt tatcttcatg tagttgaaaa tactgccagg     300
aatttaaaat ctactggtga atcaaatgga aaaatcaaag gagaagctgc acttaacaga     360
cttgcggata catttggaat atcagaggca gatattcata gaaagctgt attggtagca     420 gataaagtat tgagcgattt gtacaaacct agatttgaaa aatggatttt ggtgaataaa     480
ttaggctatg ctcctagaat tgaaaactgg caaaaattgg gcataatgcc tggaggagca     540
aaatccgaag tatttgatgc tatagtaaaa acctctacaa atttgaacag tgatgccaag     600
gacatgatgg taaactgttt aaatcttgga ataagtacag gaatttatgg acttacccctt     660 acaaacctac tgaacgacat tctacttgga gaaccttcaa taaggccagc taaagtagga     720
ttcaaagtag ttgacccttc ctatataaat ataatggtaa caggtcacca acaatcaatc     780
atatcatatc ttgaagatat tcttacaact cctgaagtaa taaaaaagc acagaaagcc     840 ggagccaaag gtttcaaact gtaggatgc acatgtgtag gtcaggatct tcaattaaga     900
ggagagcatt acaaggatgt attttcagga catgcaggca acaactttac cagtgaagca     960
ctaattgcaa ctggcggcat agattccata gtatcagaat tcaattgtac acttccagga    1020
atagagcctg tctcagataa attcatggta aaaatgatat gtgttgatga tgtagccaaa    1080
aaatcgaatg cagaatatgt agagtactcc ttcgataaaa gaaggaaat aagcaatcat    1140 ataatagacg aatcaataaa gagttatttta gacagacgtc ctaaaataaa gataaacata    1200
cctgaaaatc acggttttga taatgttata acgggcgtaa gcgaaggatc acttaaagaa    1260
tttcttggag gaacctggaa accattagtt gatttaattg ctgcaggcaa aatcaaagga    1320
gttgcaggaa tagttggctg ctcaaatctt actgcaaaag gtcatgatgt atttactgtt    1380
ggacttgcaa aggaacttat aaaaagagac attatagtac tgtccgcagg atgctcaagt    1440
ggggggcttg aaaatgtggg attgatgtct cccgaagctt caaaacttgc aggttcaaat    1500
ttaagggcag tttgtgaaag tcttggaata cctcctgtac taaattttgg tccatgcctt    1560
gctataggaa ggcttgaaat tgtagcaaag gaactagctg aatatttgaa tatagacatt    1620
ccagctcttc cattagtgct ttcagctcct cagtggttgg aagaacaggc tcttgcagat    1680
```

-continued

```
ggatgctttg gattgtccct tggacttcca cttcatcttg caatttcacc ttttatagat   1740
ggaagtgaaa ctgtttcaag attacttaca gaagacatgg aaagtctaac tggaggaaaa   1800
ttaattattg aaggtgacat taaaaaggct gctgacaaac ttgaagaaat agttctagct   1860
aaaagaaaag gcctgggact tagatag                                       1887
```

<210> SEQ ID NO 3
<211> LENGTH: 633
<212> TYPE: DNA
<213> ORGANISM: Clostridium tyrobutyricum

<400> SEQUENCE: 3

```
atgaaaatta tagatattcc atgtagaaat tttatagaag aactttcatc taaaagcgct     60
ataccgggtg gtggtggagc agcagcttta gatggagcca tgggagcggc tttattaagt    120
atggtctgta atttaactat tggaaagaaa agatatgtac aatatacaga taaactgaca    180
tcagtgttaa ataaatcagc agaattaaaa agtaattttt tgaatatggt agatgaggat    240
gcagaaaatt ttatcccact ttcaaaagct tatggtttac ctaataatac ggcagaagca    300
aagcatgaaa gagaagaaat tttagaaaag tgtttaaaat ctgcttgtgg tgttccaatt    360
aaggttgtga aaaagtcata cgaaactatt cttcttcacc aatccatatt agaaagttgt    420
tctactctcg tactaagtga tgttggagta ggtgttcaat gtttaaaatc tgcacttact    480
ggtgcttatc tcaatataat tataaatgta aagtctatga aagatagatg ttatgtagat    540
aatattaaag aggaaataga accattatta aaagatggag taaaaattgc agagaaagtt    600
tatgatagag ttgtagaaag actttcagat tga                                 633
```

<210> SEQ ID NO 4
<211> LENGTH: 1677
<212> TYPE: DNA
<213> ORGANISM: Clostridium tyrobutyricum

<400> SEQUENCE: 4

```
atgaaattta aatctgacat agaaatagct cagcagtgtg atatccagaa catagttagt     60
atagcaaaaa aattaaatat accagaagat gatttggaac tgtatggtag atataaagct    120
aaagtagact acaatattct aaaacggact acaagtaaaa atggaaagtt gatattgtgt    180
acagcaataa atccaacacc agcaggggaa ggtaagacta ctacatccat aggtcttgca    240
gatgcatttt caaaattggg aaagtctaca gtagttgcac ttagggaacc atctatggga    300
ccggtatttg gaatcaaagg cggagcggca ggtggaggat atgcacaagt cgttcctatg    360
gaggatataa atttacattt tacaggagat atacatgcat tgactgcagc aaacaattta    420
ttggctgcaa tgatagataa tcatattcag cagggaaatt ctcttgacat agatccaaga    480
agaattacat ggagaagatg tatggatatg aatgacagac aattgagatt tgttgtagat    540
ggattaggtg gaaaagtcaa tggaatgcct cgagaagatg gatttgacat aacagttgct    600
tctgaagtaa tggctatatt ctgtctggca aatgacataa aggatttgaa agatagaatt    660
tcaaaaataa tcataggata caacaggagt ggagaaccgg taacagcaca tgatttaaaa    720
gctgaaggtg ccatggctgc acttttaaaa gatgcattaa agccaaattt ggttcaaaca    780
cttgaaggta ctcctgcatt tatacatggt ggaccttttg caaacattgc tcatggatgt    840
aactctataa tggcaactaa aatggcaaga cactttggag attatgctat tacagaagca    900
ggatttggtg ctgatcttgg agcagagaag tttatagaca taaaatgcag aatgtcagga    960
```

```
ttaaaaccag atgcagtagt aatagtggct actataagag cacttaagta taatggagga    1020
gtggaaaagt caaagcttgg agaagaaaat ttagaagcac ttaatgcagg tatcccaaat    1080
ttattaaaac atgtagaaaa tataaccaag gtatttaaac tccctgcagt ggtagctata    1140
aataagttcc ctacagatac agaatctgaa attaagctag tagaatctga atgtaagaaa    1200
cttggggtaa atgtaaaatt atctgaagtt tgggaaaagg gcagtgaagg tggaatagaa    1260
cttgccaaag aagtactgag aataatagat gaagaggaaa acaattttga atttgcatat    1320
gacatggatt tatctataaa agaaaagata aaaactattg caagaagaat atatggtgca    1380
aaagatgttg attttacaaa agatgcagag aaggaaatta agaatttgga aaggttgggt    1440
ttcaataata ttcctgtatg tatagcaaaa actcaatatt ccttaactga tgacaaggca    1500
aaacttggaa gaccaacaga ttttacaatt acagtaagac aaatttctat ttcagctgga    1560
gctggcttta tagttgctgt tacaggttcc ataatgaaaa tgccaggact tcctaaagtt    1620
ccagcagcgg aaaaaataga tgtagatgat aatggaacaa taatcggact attttag      1677

<210> SEQ ID NO 5
<211> LENGTH: 855
<212> TYPE: DNA
<213> ORGANISM: Clostridium tyrobutyricum

<400> SEQUENCE: 5
atgggacagt taattaaagg gaaaccagca gctgatgctg taaccgtaca tttgattgaa      60
gaagtaaaga acttaaaacg aaaaaatatt attccaaagc ttactatagt tagggtgggg     120
aaaaatggaa gtgatatggc atatgaaaga ggggcaacca aaaggtgtaa tagtattggc     180
atagaaatag ctataaagga acttccggag gacatatctc aacagagttt tatagatgaa     240
ttgaaaaaaa taaatgagga tagtaccaca gatggaataa tggtattcag accattgcca     300
aaacaattag atgaggatat tataaaacat ttgatagatc ccaataagga tgttgattgt     360
ttcaatccat taaatatgtc taaattgctg gaagatgata attctggatt ttcgccttgt     420
actgctgctg ctgtaattga tcctggat tattataaga taaaaattga aggaaaaaga     480
gtggttgtaa ttggaaggtc aatggtagta ggaaaaccgc tttctctact tttattaaat     540
aggaatgcta cagttaccat ttgtcactct agaacacaaa gatggagaa tatatgttcc     600 caggctgata ttgttgtagt gtgtattgga aaaagtaaaa ttataaacaa agctatatt     660 aaatcaggag cagctgtaat tgacgttgga ataaatgtag acaccaatgg agcttttatgc     720 ggagatgttg atactgaaaa ttgtatagaa aaggttggta tgataactcc tgtacctgga     780
ggagttggtt ctgttacaac ttctatactt gctaaacaag tagttatggc atgtaagaga     840
caaaataata tataa                                                      855

<210> SEQ ID NO 6
<211> LENGTH: 927
<212> TYPE: DNA
<213> ORGANISM: Clostridium tyrobutyricum

<400> SEQUENCE: 6
atgcttaaag ataaaatatt gaatagagaa actggaataa taacatatgc aataacaccg      60
ccaaaattaa acaatttaca tcaaaaaatt gtagaaattt ctcaaaaaca ggtagagcgg     120
ataaagaaca ttgatgtaga tggcctaatt atttatgata ttcaagatga aattgacaga     180
cagaaagaaa agaggccatt tccttttatt gaaacattgg atccagcttt gtataacgag     240
gagtatttaa agaatttaac tgttcctaaa attatataca gatgtgtagg aaaatatgat     300
```

```
gaaaatcagt tttcaaaatg gataaaatct gataaagata gcgatagatt ttctgtattt    360
gttggagcat cttctagtaa acaggaagtt aagttgaaat tatctgaagc atatagaata    420
agtgaacaat taaatccaaa tttaatttta ggtggagttg taatacctga aagacatgtg    480
actcataaag atgaacatat gagaataatc aataaagtag gtaaaggatg caaatttttc    540
gtctcacagg taatatataa tctggaaaat tccaagaatt ttttatcgga ttattattat    600
tactgtaaaa ataataatat tgagatgaaa cctataatat ttactattac gccttgtgga    660
tctaaaaaaa cattgcaatt catgaaatgg cttggaataa atgtcccaaa gtggatggaa    720
aatgatctta tgaattcaca ggatatattg cataaatcag tatctttatc agagaatatt    780
gttgaagaat tattggattt tgcattggag aaggatatac cagttggatt taatattgaa    840
agtttgtcaa ttagaaaagt tgaaattgaa gcttcaataa aattggttaa agatataaaa    900
tcaataattg aaaagagatt aaaatag                                        927
```

<210> SEQ ID NO 7
<211> LENGTH: 2454
<212> TYPE: DNA
<213> ORGANISM: Clostridium tyrobutyricum

<400> SEQUENCE: 7

```
gtgacttgta ataatttatt ggaaaaaatt aagaataatt ttatattttt tgatggagcc     60
atgggcacta tgcttcaaag agcaggactt aaaacaggtg agcttccaga aattctaaat    120
ataacaaatc cagatactat aaaaaaaata catgaagctt atcttaatgc aggagctgac    180
attataacta ccaatacttt tggagcaaat gatttaaaat atagctcttc tgattattca    240
tcggaggagg taattgaagc tgcagttgga attgcaaggg aagctgttaa aagcagagaa    300
aataaatttg tagctcttga tataggacca ataggacaag tgatggagcc tactggaaat    360
ttaagtttcg attcagctta taaattattc aaaaagcagg tagttgcagg agacaggtca    420
ggagccgatc ttatagtaat tgaaactatg atggatctgt atgagactaa ggctgcagtg    480
cttgctgcca aagaaaacag ttcacttcca gtgttctgta ctatgacttt tgaaaaaaat    540
ggaagaagcc tcatgggcac tgaccctaaa acaatggtat ttgttttaga aggacttgga    600
gtggatgcaa ttggagttaa ttgttcccta ggacctaatg aacttcaggg catagtagat    660
gaaattttga agtatgcgtc tattccagtt atggttcagc ccaatgcagg gcttcctaaa    720
tacaatggag tggaaactta ctatgatata agcatagaag agttttcaaa aaatataaaa    780
ataatggctc agaagggagt aagaataatt ggaggatgct gcggtacaaa tcctgatttt    840
ataaaagatt ttataaaaga attgaaggat attaaaccta tagatatagg agaaaaaaac    900
tacacagcag taacttcagc aactgaaacc gtaatagtag aaaataaaac taggattata    960
ggtgagagaa taaatcctac agggaagtcc gcatataaaa aagaacttag ggaaaagagt   1020
attgattata tacaaaagca ggctttgata caaagagatg aagaagcgga tatactcgaa   1080
ttgaatgtag ggcttccaga gataaacgag gttgagatga tgaagaaggc agtgagagca   1140
gtacaaaaag tagtgtatac acctataagc atagatagtc caaatgcaag tgcactagag   1200
gcaggcgcaa ggttatacaa tggaaaacct ctcataaatt ctgttaatgg aaaagaaaag   1260
actatggagg atgtatttcc aatagttaaa aagtatggag gatgtgttat agcacttact   1320
atagatgaag atggtatccc caaaaccgct cagaagagat ttgaaattgc ggaaaaaata   1380
gtaaggaggg cagcagaata tggaatacca aaaaaagata tagtagttga ttgtttgtca   1440
```

```
cttacagctt cagcccaaca gaaggaagta atggagacgg taaaggcaat aaggcttgta   1500
aaagaaggat tgggtgtaaa gactactctt ggtgtaagta atgtatcttt tggacttcca   1560
catagaaaac tcttgaacag gacatttttg ttgcttgctc ttcaggctgg attagatctt   1620
cctataatga atccttcgga taagggtatg aaggatacta tagctgcatt tcaagtactt   1680
gccaatagag atgtagacag cagggaattt atagatagat acaaggatga atcagaggaa   1740
tcaaataata gccgattatc tgcaaaaaaa gtcaaggata agaattttga caatataaag   1800
ttggataaaa atagcagtga cttaaaacag ataattataa atggtgatga aggtgcagca   1860
tctttagcta ctgaagaact tttaaaatcc aaacaacccc ttgatgtggt aaattcatat   1920
ataataccag cgctggatca agtcggagta aagtatgaaa caaaggagat atttctaccg   1980
cagctcatac aggcggctga aaccgtaaaa aaatcatttg aagttataaa aaaaatcata   2040
gttgaaaatg gtggtcagaa tgtagaaaag ggaaaagtga ttttggctac agtcaaggga   2100
gatgtacatg acataggaaa gaatatagta aaagtcctcc ttgaaaatta tgggtttaat   2160
gtaattgatc ttgggaaaga tgtagatata cagaaagtag ttgatgctgc aaaagaaaat   2220
aatataagac ttgtagggtt aagtgcactc atgactacta ccgttatgaa tatgaaaaaa   2280
actatagatg cattgaaaaa aaataattta tcatgtaaag ttgtagtagg cggcgcagtg   2340
ctgaatcagg aatatgcaga tatgataggc gctgattttt atgcaaaaga tgccagagat   2400
acagttaaga tagctgagga attattttca aaagataaag taggaacaaa ttag         2454
```

<210> SEQ ID NO 8
<211> LENGTH: 2073
<212> TYPE: DNA
<213> ORGANISM: Clostridium tyrobutyricum

<400> SEQUENCE: 8

```
atggagataa aacagtccac ttgtaattat tgttctctag cctgtaatct ggaattttat     60
gtagaagata atatgattaa aaaaatattg cctaaaaaag attaccctgt gaatggaaaa    120
ttcacctgtt taaaaggtat aaatcttgat aaacagtgca gtagatatgg aaaagataaa    180
ctacctgtgc tgaaagacga atatggaaat aaaagggcta tttcatggaa tgaggccttt    240
gaattatttg cagataaaat gcggtacata caaaataaat acggagttga aagtgctgca    300
tatataagca caggccagat aactacagaa gaacttgcac ttttgggact tgtaggcaga    360
atacacatgg gcataaatgg agatggcaat acaaggcttt gcatggcttc tacagttatg    420
gcgtataaac agagttttgg atttgacgct cctccctata cattaaagga tcttgaaatt    480
tcagatacac ttgtatttat aggagcaaac cccgctattg cccatcctgt agcctggtct    540
agagtcaaaa aaaataaatc tgccagtata gtggtcatag atccaagaga atcagagaca    600
gcacaaaatg cggatatttg gctggatata attccaaagt cagatattta tcttttgtat    660
acacttgcca atgtgcttat agaaaataac tggattgaca gagaatatat agataattat    720
actatggatt ttgatggatt tagagaccac ataaaaaagt ataatattgc aagtgtggag    780
aaaaataccg gtatatcgag tgaaagagtg cttgaacttg cgcagttgat tcacaatgga    840
aagagagtgt cattttggtg gaccatgggt gtaaaccagg ggtatcaggc tgtaagaact    900
gcacaggcaa ttataaacat tgcagttatg actgggaata ttggaagaga gggaacagga    960
ccaaattcat taactggaca gtgtaatgca atgggatcta gaatgttcag caataccacg   1020
gccctttatg gaggaaggaa ctttgacaat cctaaacacc gaagggatac agctgaaatt   1080
cttggagtgg atgaagaaaa gattcctaaa aagcctacta taccctacag tgaaataata   1140
```

```
aacaggatag ataggggtga gataaaatca ctttgggtta ttgccaccaa tcccaggcat   1200
tcatgggcca acaacaagga atttgaaaat gcagtaaaaa aactggactt ttttgtagta   1260
caggatctct atggagatac agacagttca aaaatatgtg acctgttttct tccttccgtt   1320 ccacttacaa aaaagcaagg atccattata aatactgaga aagattgtc ggcagtagta    1380 cctgtaattg atatgggaaa agatgagatg agtgactatg atatattcct gggaataggg   1440
agagctcttg gaatgaaaca agaacttgaa agtggaaaa ccccacttga cgcatttaat    1500
accataaaag aactcagcag gggaatgccc tgtgatataa caggcataga ttatgaaatg   1560
cttgtaaact ccaaagggat acaatggcct tttaaaagtg gggacaaatt acttcaagat   1620
gaaagaagac ttttgagga caatatatac tttacccaaa acggaaggat gaagttcata   1680
tatgagaatg taatgaaaaa tccgtgtccg gtcgattcaa aatttccata tatattgaat   1740
acgggcagaa tatccgtagg ccagtggcat actcagagca gaacaagaga aataaattca   1800
ggaaattctt caattgttaa agcagcatat gtaaatactca atgtgaaatt ggctgaaaca   1860
cttggcatag aagaaggtga caatgtaata atttcatcta taaatggaaa caacagtaaa   1920
ttcaaggcga gattaagtag tatgattaaa gaaaaccaac tgtatgcgcc tctgcactat   1980
atagagacaa atgtactttc tgtttcagta tttgataccrt attcaaaaga accttcttat   2040
aaatatatac ctgtaaattt agagaaaatc taa                               2073

<210> SEQ ID NO 9
<211> LENGTH: 1404
<212> TYPE: DNA
<213> ORGANISM: Clostridium tyrobutyricum

<400> SEQUENCE: 9
atgattttta ccgttggtcc tgctagtgac acagatgaaa ttttatcaaa acttattgag    60
gctggtatga gtgcttcaag acataacttt tcacatggtg accatgaaga gcataaggga   120
agaatggatg caataaagag acttaggaaa aaatacaata acaaatagc tataattctt    180 gatacaaaag gaccagaaat aagaaccggg gatttttaaaa gcaagcttga attaaaagaa   240
ggtcaaaaat tcactgtata ttgtggagaa gaaattcttg gagatgaaac taagtgttcc   300
ataacttatg cagatctta taaagatgta aagcctggag acagcatact tattgatgat   360
ggattagtag gtatggaagt tgaaagcata gatggaaaca aaataaattg tgtagttaag   420
aatagtggtt tagttagcag tcataaaggt gttaatgtac caggagtatc cataaagctt   480
ccggctacta cagaaaaaga cgaatcagat ttgaaatttg gatgcgaaca aggcgtggat   540
ataataacag catcctttat aagaaaagcc caagacgtaa taactataag aaatatactt   600
aagaaaaatg gcggagaaca catccagata ttctcaaagg tagaaaatca ggaaggtgta   660
gacaatatag atgaaataat agaagcttca gatggaataa tggttgcaag aggagatatg   720
ggagttgaaa ttccaataga aaagtacct cttatacaaa agtccataat agctaaatgc   780
aatagtgtag gtaaacctgt tataacagct actcaaatgc ttgattcaat gataagaaat   840
ccaagaccaa caagagcaga agcatcagat atagcaaatg caattttttga tggaacagat   900 gctataatgt taagtggaga atctgcaaat ggtaaatatc ctgtagaagc agcacagact   960
atggcaagaa tagctcaatc tgcagaatcc aagattaatt ttgatgaatt acttaaaaag  1020
aaaagagaag ctagtgtaac tgatgtatcc aatgctataa gttttgcagc ttgttctaca  1080
gcagctgaat taaatgcaga tgcaataata acagctactc agagcggaag tacagctgta  1140
```

| | |
|---|---|
| agagtttcaa agtacagacc tgcttgtccg gttattgcag ctactccaaa tgaaaaagta | 1200 |
| tgtagaaaat tagctcttaa ttgggggggtt tttgcaatac ttacagataa atatgaatct | 1260 |
| acagatgaaa tggtagaaaa atctatagat gcatcattaa aagctggtta tataaagaaa | 1320 |
| gatgatttgg cagttataac tgcaggagta ccagttagca ctactggtac tacaaacatg | 1380 |
| atcaaggtta atgtagttaa ataa | 1404 |

<210> SEQ ID NO 10
<211> LENGTH: 3525
<212> TYPE: DNA
<213> ORGANISM: Clostridium tyrobutyricum
<400> SEQUENCE: 10

| | |
|---|---|
| atggatggta atacagccgc tgcacatgtg gcttatgcat ttactgaagt agcaggtatc | 60 |
| tatcctatca caccatcaag tccaatggct gatgttattg accaatggtc tgctgcagga | 120 |
| cgtgaaaata ttttttggta atcaagttaat gttgtagaaa tggagtctga agcaggtgct | 180 |
| gcaggaactg ttcatggttc tcttgctgct ggagctatca caacaacatt tacagcatca | 240 |
| cagggtcttc ttttgatgat tcctaatatg tataaaattg ctgctgaaca gcttccttgc | 300 |
| gtatttgatg tatcagcacg taccgttgct actcagtcac ttaatatatt cggtgaccac | 360 |
| agtgatgtat atgcttgtcg tcagacaggt ttcgcaatgc ttgctgaaac aaatccacag | 420 |
| gaagtaatgg atttaagccc agttgcacat ctttctgcaa ttgaaggtaa agttccatt t | 480 |
| ataaacttct ttgatggatt ccgtacatct catgaaattc agaaaataga aaaatgggat | 540 |
| tatgaagatc ttaaagaaat gtgcaacatg gatgcggtta agctttccg tgaacatgca | 600 |
| ttaaacccag aacacccagc tatgcgtggt tcccacgaaa atggagatgt attcttccag | 660 |
| catcgtgaag caagcaacac aacttacgat aaattaccag ctgttgttga aaatacatg | 720 |
| gctaaggtaa atgaaaaact tggtacaaac tatgacctgt tcaattacta tggagctcct | 780 |
| gatgctgacc gtgtcatcat cgctatggga tctatatgtg atgtagctga agaagttat t | 840 |
| gattacttaa cagctagggg agaaaaaatt ggaatagtta agttcgtttt atatcgtcca | 900 |
| tgggtatcca attcacttct taagttttta cctaaaacag ctaaaaaggt tgcagttctt | 960 |
| gaccgtacaa aagagccagg agcacttgga gatccactat atcttgatgt agctacaact | 1020 |
| cttcgtgaag caggacttaa tgacgtagta ttaacagctg acgttatgg acttggttct | 1080 |
| aaagatactc caccttcaag tgtatttgct gtatatactg aattgaagaa agatgctcct | 1140 |
| aaagctcgtt tcacaatcgg tatagttgat gatgttacaa acttgagttt gccagaagtt | 1200 |
| aaaccagctc ctattacatc tgcacctgga actgtagaat gtaaattctg gggtcttggc | 1260 |
| ggtgatggta cagtaggtgc caacaagaac tcaacaaaga tcctaggaga ccatacagat | 1320 |
| aaatatattc aagcatattt ccagtatgac tccaagaaaa ctggtggtgt aacaatatca | 1380 |
| catcttagat ttggtgacaa gccaatcaga agcccatatt atataaatca ggccgatttt | 1440 |
| gttgcatgtc ataatccatc atatgttgtt aaaggatata gatggttca ggacgttaaa | 1500 |
| ccaggtggaa cattcatgat caactgtcag tggtcagacg acgaactgga ttctaagata | 1560 |
| actgctgatt ctaagaaata catagcagat aacaacatcc agttgtatac aatcaatgct | 1620 |
| attgacaaag caattgaaat tggtatgggt aaacgtacta atacaattct tcaatctgca | 1680 |
| ttctttaaat tggcaaatgt tatgccaatt gatgatgctg ttaagtttat gaaagctgct | 1740 |
| gctaaaaaat cctatggtaa aaaaggcgat gcaattgtag aaatgaacta taaagcaatt | 1800 |
| gatgccggtg tagatgctgt tcataaaata gatgttccag cttcttggaa gaatccagca | 1860 |

```
ccagacgctc cagctccaaa acttgaggga cgtccagaaa cagttaagat ggttaaaaat   1920
cttatgaatc ctattacact tatggatgga gacagtcttc ctgtatctgc atttgaagaa   1980
aatccagatg gacagtttga aattggtgct gctgcatatg aaaaacgtgg tactgctgta   2040
aatgttccag aatgggatcc agataaatgt attcagtgta acgttgttc atttgtatgt    2100 tctcatgcaa caattcgtcc atttatgtta agtgaagctg aagtagaagc agctccttca   2160
aacataaaag ttgctgatac taagccaaag gctggaaaat tcaagtttac aatgagcgta   2220
actcctcttg attgtatggg atgcggagaa tgtattaccg tttgtcctac aaaggctatc   2280
aagatggtac ctcaggaatc acaactagac cagcagccag tatttgacta cttagttgct   2340
aacgtaggca agaagccagg agtaccagct gatactacag ttaagggttc acagttcaat   2400
cagccacttc ttgagttctc aggaagctgt gcaggatgtg ctgaaacatc ttatgctcgt   2460
ttgcttacac aattgtttgg tgaacatatg tacatctcaa atgctacagg atgttcttct   2520
atctggggtg gtcctgctgc aacaagtcca tttacagtta ataaagattc aaatatgggt   2580
ccagcttggg ctaactcatt atttgaagat aatgcagaac atggatttgg tatgtatctt   2640
ggacagaaga cacttcgtga ccaagctata gctaaaatcg agaagatggc tgcttctgac   2700
aaagcatctg atgaattaaa agctgctgct aagaagttta tagaaacaaa agatagtaca   2760
aaagaaaaca cagctgctgc taatgcatta gtagctgaac ttgaaaaagc tgctgctgca   2820
ggctgtgata cttctaaaga attacttgca agtaaacagt accttgctaa gaagtcagta   2880
tggattcttg gtggagatgg atgggcatat gatatcggat tcggtggact tgaccatgta   2940
cttgcttcag gagaaaatgt aaatgtcatg gtattcgata cagaaatgta ctcaaataca   3000
ggtggacagg cttcgaaggc ttccaacatc ggtgaagttt gtcagttcgc tgctgctggt   3060
aaagaagttg aaagaagag ccttgctgaa atagctatga gctacggata tgtatatgta    3120
gcacagattg ctcttggtgc aaaccccagct cagactgtta agactatttc agaagcagaa   3180
gcttacaatg gaccatcact tataatcgga tatgcacctt gtgaacttca cggagttaag   3240
ggcggcatga atcattgtca ggatgagatg aagaaagctg taaaggctgg atactggaat   3300
ctgttctcct ttaatcctct tcttaaggct gaaggaaaga atccattcac tcttacatct   3360
aaaccaggtg atgaacttta tcaggacttc ttgaacaatg aaacacgtta tactcgtttg   3420
aaacgtgcat tccctgatcg tgcagagaag ttgttcgata atctgaggga atctgcaaaa   3480
gatcgttatg accatttgtt aagattagta gaactttata aataa                   3525
```

<210> SEQ ID NO 11
<211> LENGTH: 2271
<212> TYPE: DNA
<213> ORGANISM: Clostridium tyrobutyricum

<400> SEQUENCE: 11

```
atgcaaaata gtaaaaatat ttttaaaagg agaaatatta tgaaaaacca atggaataat     60
tttagtgatg gtgcatggac agaaaatatt gatgtgagaa attttataca gaaaaactac    120
aagccttatg gtggtgatga aagcttttta acatctccta ctcttaaaac taaaaacata    180
tgggaaaaat cggaaaaact gattttacaa gaaattaaaa aaggcggagt tttagatgta    240
gatactaaaa cagtatctgg tgttgacaac tttaaacctg gatatataga taaagaaaat    300
gaggtagtat tcgggcttca aactgatgct ccacttaaga gaatggtcaa tcctttcggg    360
ggaataagaa tggctcaaga ggcacttgaa gactatggat ataaagtaga tgatgaaatg    420
```

```
catgatatat ttacaaaata tagaaagaca cataatgaag ctgtatttga tgcatacacg      480
gaagaaatga aagcggcaag acatgttgga ctattaactg gacttcctga tgcctatggc      540
aggggaagaa taataggtga ttttagaaga atagctctat atggtataga ttatttaata      600
gaaatgaaga aaagtgattt aaaggcctta aaaggtgata tggatgaaac tttaataaga      660
aggagagaag aagtagcaga gcaggtcaag gcacttaaaa agataaagaa catggcatca      720
cgttatggaa tagatatatc agatcctgcg gcgaatgcaa aagaagctgt acagtttact      780
tattttggat atcttgcagg aataaaggag aataatggtg cagcaatgtc acttggaaga      840
gtttcaacgt ttttggatat ctatatagac agggatttaa aagcgggaat aataagtgag      900
cagggtgcac aggagctaat agaccagttt gtaatcaaac taaggcttga aagacatctt      960
agaacacctg aatacaatga actatttgca ggagatccta attgggttac tgaatccata     1020
ggtggtatgg gaatcgacgg caggacattg gttactaaaa attcttatag attttttaaat    1080
acacttataa atctggggcc tgctccagaa ccaaatatga ctgtattatg gtctgaaaat     1140
cttccagaac catttaaaaa gtactgcagc agaatatcta tagaaacaga tgcagttcag     1200
tatgaaaatg atgatgtgat gagacctata tatggagatg actatgctat agcatgctgt    1260
gtatcagcta tggcagtagg aaaacagatg cagttttttcg gagccagatg caatcttgca    1320
aagtctcttc tctatgctat aaatggagga gttgacgaga aaaaattcca aaaaatagta    1380
ccgcatatag ataaaatgga tgatgaaata cttgactatg acaaagttaa aaagagttat    1440
tttaaagtta tggaatatgt agcaaaactt tatgttaata cccttaactt gattcactat    1500
atgcatgaca aatatgctta tgaagctgca cttatggcac tccatgacac agaagttcat    1560
agatttcttg cttgcggtat agcaggactt tctgttgcag cagattcatt aagtgcaata    1620
aaatatgcca gtgtaaaacc aataagaaat gaacagggta ttgctgtaga ctttgaagtt    1680
gaaggagatt ttcctaaata cggtaatgat gatgacaggg tagatgacat agcagttgaa    1740
attgtaaata aatttataag tgaacttaga aaaacagaag catacagaaa tgcggaacat    1800
actttgtcgg ctcttactat aacttccaat gtaatgtatg gtaaaaagac tggaactaca    1860
ccggatggaa gaaaatctgg agaaccactt gctccaggag ccaacccaat gcatggaaga    1920
gataaagaag gggcacttgc atctttgaat tctgtagcca aaataccata tagatccgta    1980
tgtcaggatg tgtttcaaa tacattctca attgttcctg atgctcttgg aaaagatgag    2040
aacaacaggg ttgacaatct tgtttcaatc ctagatggat attttttcaaa aggtgcacat    2100
catctgaatg taaatgtaat gaacagggaa acacttttag atgcagtaga caatccagag    2160
aagtacccta cactgactat aagagtttca ggatatgcgg ttcactttgt aaagctgaat    2220
agggaacaac agatggaagt aatacacaga actttccatg agagggttta g              2271
```

<210> SEQ ID NO 12  
<211> LENGTH: 741  
<212> TYPE: DNA  
<213> ORGANISM: Clostridium tyrobutyricum
<400> SEQUENCE: 12

```
atgggcagga ttcattctat agaaaccatg ggactggttg atggacctgg aataagggta       60
gttgtatttt tccagggctg cagacttagg tgtgcttttt gtcataatcc tgatacatgg      120
aaactggatg ccggagagga cattagtgca gagcagcttc ttgaaaaagt tgaaagatac      180
agagtctatt ttgaaaagtc aggagggga gttacctgtt ctggaggtga ccctctaatg      240
cagcctgaat tcttgattga attttttaaaa ctatgcaggg aaaatggaat aaataccata    300
```

```
gttgatacat ctgggtttgg aaaaggaaat tataaggaaa ttttaaaata tacggatctt    360
gtaatgcttg atataaaaca tattgatgat gctggatata aagaacttac aggtggaaat    420
attcaggagt tttatgattt cctaaaggaa gttaataatt caaatgcaaa attgtggata    480
aggcacgtaa tggttccagg tgtaactgac aattatgaat gcatggataa aatagtccat    540
ataatagaaa actctgttaa atcaaataaa ctggagaaat ttgaaatttt accatatcat    600
actatgggag taaacaaata tgaaaaatta ggtgtgaat acaggcttaa aggtgtcaag    660
ccaatggata agaaaagagc cctggaattt caaaaatatg ttgtagaaaa aatcaataaa    720
aataaaagta tcacaattta a                                              741

<210> SEQ ID NO 13
<211> LENGTH: 2403
<212> TYPE: DNA
<213> ORGANISM: Clostridium tyrobutyricum

<400> SEQUENCE: 13
atggcagaat cagtattaaa agaagtaaaa agaggttcaa cagaacgtat aaggagatta    60
agagaaatta gtactaaaaa aagtaagccc agtatttcca tggagagggc agttttatta    120
acagaagctt acaaaaagta tgaaggaaaa ttttcaactc cagttcttcg tggattagct    180
tttaagtaca ttatggaaaa tcgtacactt tacattgaaa aaggcgctat catattagga    240
gaaaaaggac acaagccgtg gctgcacca actttcccgg aattatgctg tcatactatg    300
gaagatttta ataatgtgaa caacagggaa aaggtctttt ttaaagtttc tgaagaggac    360
atgagaattc agaaagaagt aattattcct tactggaagg atcgtgcgct gatgacacgg    420
atgaacagat tattgccgga tgaatggcac aagctgtttg atgcagggct gtatactgaa    480 ttttttgatgc agcgtggtcc agggcatact gtagctgacg gcaagatata ccgtaaaggg    540
tatgctgatt ttattgatga tattcaatat gaaattgacc attttggatta caataatgat    600 gtacttgcac ttaataaaaa ggaagaattg gaaggcatga agctggtttg cgaaggcatg    660
attatctttg acagcgttta tgcagccaag gcacgtgcac tggcatccat tgaagaggat    720
tcacaatgga acaggaatt attggatctg gctgaagttt gcgatgcagt gccaaaacat    780
gcaccagaaa ccttccgtca ggcagtgcag atgtactggt ttacccatat aggagttact    840
actgaaatga ataactggga tgcttattct ccaggtaaat ttgatcagca tcttgaacct    900
ttctatgaga agatatcga agaaggtcgt ctgactcgtg aaggagcccg tgaaattta    960 gaaaatctat ggatacagtt taacaatcaa cctgcacctc caaaggttgg ataaacttta    1020
aaggaaagtg ctacttatac ggatttctgc aacattaata caggggctct gcgtgctgat    1080
ggaacaacag gtgtaaatga agtcagctac ttgattctgg aagtaatgga tgagatgaaa    1140
ttgctgcagc ctagttcaaa tgtacagata tcccgcaaaa ctccagaaaa attcctgcgt    1200
gaggcagtga aaatttcacg taaggatgg gggcagccag cctttacaa ttccgaggct    1260 attatacagg aattgttgtt ccttggtaag tccattgatg acgccagaga gtgcggaatt    1320
gccagcggat gtgtgaaaac tggtacagct gggaaggaag cttatgtact gactggatat    1380
ttgaatatac caaaaatctt tgaactggtg ttgaatcgtg atttgacag ttatacaaaa    1440 aaacaggcag cattggattt tggagatcca cgtgaattca gtcctatga agaagtttat    1500 aatgccttct acagacaact ggaatatgta gtaaacgtga aaattgcagg aaacaatttg    1560
attgaacgta tgtatatgga gtatatgcca gtcccattgt tatctgttat aactgatgat    1620
```

```
tgcatcaaat ccggtattga ctacaatgct ggtggggccc gctataatac aagctatatt    1680
caatgtgtag gcatagcaac tattactgac tcacttgtct ctataaagaa aaatgtattt    1740
gaagataaga aattttctat ggatgagtta ttaaaagctt gtaaagctga ttttgaaggt    1800
tatgatgaaa tctttgaaac agtctataac aatactccaa agtatggaaa tgacgatgat    1860
tatgcagatg atatattgag agatgtttca aattctctac aggatgctat tgcaggaaga    1920
actacaccaa agggatcaag gactgtagtt gaattccttc caacaacttg tcatgtatat    1980
tttggtcagg taatggaagc cagccctaac ggccgccatg ccggtgttcc acttccagat    2040
ggtatttccc ctgaaaaggg tgcggataga atggccccta ctgccgtaat taagtctgct    2100
tctaaaattg accagctgaa gactggaggg gcattgttga atcaaaagtt tacaccggca    2160
gttgttcaag gtgaagacgg agtatccaat ttggcagttt taatccgttc atactttgcc    2220
atggatggtc atcatataca attcaatgtt gttgatcgaa aaactttgct tgatgctcaa    2280
aagcatcccg aggaatatga aatttgata gtaagggttg ccggatacag tgattatttt    2340
aataatctgg atagagccct gcaggatgaa attatcaacc gtacggagca gggatttgct    2400
tga                                                                 2403

<210> SEQ ID NO 14
<211> LENGTH: 993
<212> TYPE: DNA
<213> ORGANISM: Clostridium tyrobutyricum

<400> SEQUENCE: 14
atgaaacaaa tatgggaaaa ggcaaaaaca gataaaaaga caattgtttt agctgaaggc     60
gaagaagaaa gaaatcttaa agcaggtgaa aaataactaa aaatggtct tgccaatgta    120 ataatggttg gaaacattga tgtaataaag gaaaaggtta gcaagttgaa tgtagattta    180
actggtgtta cattggtaga tccacaaact tctgataaat tagaaaaata tgctcatgag    240 tttttatgaat tgaggaagaa aaaaggtatt actcctgata aggcgaataa atagttaga     300 gacccattgt actttgcaac aatgatggtc aaactaggag atgctgatgg attggtatct    360
ggttctatac atactacagg cgatcttttg agaccaggtc ttcaaattgt aaaaactgct    420
ccaggaactt cagtagtttc aagcatattt atgatggaag ttccaaattg tgatttaggt    480
gataatggtt tcttgttgtt ttcagattgt gctgtaaatc ctgtacctaa tactgaacaa    540
ttagctgcaa tagctattag tactgcagaa actgcaaaaa gtttatgtgg tatggatcca    600
aaagtagcta tgctttcatt ttcaactaag ggaagtgcac aacatgaaaa tgtagataag    660
gtaagagaag caaccaaact tgctaaacaa atgcaaccag atcttaaaat agacggagaa    720
cttcaattgg atgcttcttt aatacaggaa gttgcaaatt taaaagcacc tggtagtcct    780
gtagcaggaa aagcaaatgt acttatattc cctgaacttc aagcaggaaa tattggatat    840
aaattagttc aaagatttgc aaaagcggaa gcaataggac ctatatgtca aggctttgca    900
aaaccaataa atgatttgtc aagaggatgc agttctgacg atatagtaaa tgtagtagct    960
gtaacagcag tacaagcaca agctgcaaaa taa                                 993

<210> SEQ ID NO 15
<211> LENGTH: 1197
<212> TYPE: DNA
<213> ORGANISM: Clostridium tyrobutyricum

<400> SEQUENCE: 15
atgaaaatat tagtaataaa ttgtggaagt tcatctttaa aatatcaatt gataaatatg     60
```

| | |
|---|---|
| gaagatgaaa atgtacttgc taaaggtctt gtggaaagaa taggtataga aggatccatc | 120 |
| cttactcata aagtaaatgg agagaaatat attactgaac agcctatgga agaccataaa | 180 |
| atagctataa aattagttct gaatgcacta gtagacaaag attatggagt tattaaagat | 240 |
| atgtctgaaa tatctgcagt tggacataga gttgtacatg gtggagaaaa atatgcaaat | 300 |
| tcagttctag tagatgaaga tgttgtaaaa gctataaaag attgtgctaa attggcacca | 360 |
| cttcataatg taccaaatat gataggtata aatgcatgta aagagttaat gccagatact | 420 |
| cctatggtgg caacatttga tactgcattc catcaaacac ttcccaatta tgcatatact | 480 |
| tatgcagtac catatgatct atatgaaaaa tatggtgtta gaaatatgg attccacggt | 540 |
| acatcacata aatttgtatc aatagaagca gctaagatga tgggaaagga cataagatct | 600 |
| cttaagatta taacctgcca tttgggaaat ggagctagtg tatgtgcaat tgacggtggt | 660 |
| aagtcaatag atactagtat gggatttact ccacttgcag gtctttgcat gggaactaga | 720 |
| tgtggagata tagatccagc agtgattcct tttctagtaa aatcagtggg aatgtctata | 780 |
| gatgaagtag ataccttaat gaataaaaaa tctggtgtac ttggtgtatc aggagtaagc | 840 |
| agtgatttta gagatgtatt agctgaagaa gctaaaggaa ataagagagc ggaacttgct | 900 |
| ttgaatgttt atacttacag ggttaaatca gtaataggct cttatatagc agctttaaat | 960 |
| ggagttgatt gcatagtatt tacagctgga tctggagaaa attcagaacc tttgagaaga | 1020 |
| agaatatgtg ctggactttc aaatttaggt atagttttag acaaggaaag aaacaatgtt | 1080 |
| atgggaaaac cagctcaaat aagttcgat gattctaaag taaaagtatt tgctattcct | 1140 |
| actaatgagg aacttatgat agctagagat acaaaagaaa tagttgaagg tagataa | 1197 |

<210> SEQ ID NO 16
<211> LENGTH: 1593
<212> TYPE: DNA
<213> ORGANISM: Clostridium tyrobutyricum

<400> SEQUENCE: 16

| | |
|---|---|
| atgaagtcaa aattaatgtc taaggacaag gcagttaaat taataaaaga tggagatact | 60 |
| gttgcagtag gtgcctttgt tggatgtgca catccagagg atattacatc tgaaattgaa | 120 |
| gaaaattata ttgaaaatcg tactcctaaa aatctaacat tgatttatgc tgcgggacaa | 180 |
| ggtgacagcg ctgatagagg actgaatcat tttggacatg aaggattagt cagtaaagta | 240 |
| ataggtggac attgggcatt aagtcctaaa cttcagaaat tagctcttga caataaaata | 300 |
| gaagcgtata atctgcccca gggaataata tcacaattgt atagagatat tgctgctaaa | 360 |
| aggccgggaa ccataaccca tgttggatta agacttttta tagatcctag acttgaaggt | 420 |
| ggaaagttaa atacaattac taaagaaaac atagtagaac ttataaatat aggaggaaaa | 480 |
| gaatatttat tttataaaac tataccattg gatgttgtaa ttttaagagc tacttatgct | 540 |
| gatgaattg gaaatgctac tatggaaaaa gaagcggcaa tattagatgc aacagctatg | 600 |
| gctcaagctg caaagaactc aggaggtata gttatcgtac aagttgaaca agtagtatca | 660 |
| aaaggatctt tagatcctaa aaaagtaaag ataccttgga tatatgtaga tgctatagtt | 720 |
| gtatcacaac ctaaaaatca tatgcagact tttagtgaaa actataatcc atcatattct | 780 |
| ggagaagcaa gatttttagt gaattccata gttcctatgc aacttaatga agaaaggtt | 840 |
| atagccagaa gagcggctat ggagcttgtt ccaaattctg taactaatct tggcattgga | 900 |
| ataccagaag gaatagcgac agttgccaat gaagaaggca ttgcagatga aatgacattg | 960 |

```
actatagaat caggtggtat aggaggagta ccttcaggtg gactgagctt tggtgcttca   1020
actaatcctc aaagcatact tgatcaggca agtcaatttg actattacga tggaggaggt   1080
cttgatgtag catttttagg gcttgctcag tgtgacagag atggtaatat aaatgtaagc   1140
aaatttgggc ctaaaattgc aggttgtgga ggatttatta atataagtca aaattccaaa   1200
aaagttgtgt actgtggaac atttacagca ggtggtttaa aggtcaaagt ggaaaacgga   1260
aaacttaata tagaaaagga tggaaagttc aataaattta tagatactgt tgaacagata   1320
tctttcagtg gtcaatatgc tcagagtatt ggacaaacag tactttatat aactgaaaga   1380
gcagtattta gattgacaaa agaaggtctc tttttagagg aaatagctcc aggtatagat   1440
atgaaaaagg acatattgga tcatatggat tttaggccta aaatatctga aaatttaaag   1500
ataatggatg aaagaatatt taagaagaa ccaataggaa taaatattgg acaatcatca   1560
aaagaattcc caggagaatt aagcaatgta taa                                1593

<210> SEQ ID NO 17
<211> LENGTH: 954
<212> TYPE: DNA
<213> ORGANISM: Clostridium tyrobutyricum

<400> SEQUENCE: 17
atggatgaag ctaagtattt ggataagttt agtaaaaaat ataatgttga aattgaattg     60 tgtaagaag gaccaacttt ggaaaatgcg aatctagcaa gtggatttaa ttgtataagt    120
attattacaa cgccagttga tagaaattta attaaaaaat tttatgaagt tggtgtaagg    180
tttatatcta caagaacaat tggatatgat catatagata ttaaaagtgc tagggagttt    240
ggtattcatg ttggaaatgt aacatattca ccaaatagcg tagctgatta taccataatg    300
atgatactta tgatatcaag gaaaatcaaa actattatgg aacgaagcaa tgtacaagat    360 tattcttta agggagttca aggaaaagaa ttacaaaact taactgtggg gattattgga    420
acggggagaa ttgaaaaaac tgtaataaag catttaagtg gatttgattg taaaatgttg    480
gcctatgata tatataaaga taaaaaatta atcaatatg ttgagtatgt taatctaaaa    540
gaactatttc aaaaaagcaa tattataaca atgcatgtgc cagctacaaa ggataattat    600
catataatag ataagaattc tataacattg atgaaagaag gagtattat tattaataca    660 gccagaggat ctttaataaa taccgatgat ttaattgatg gtagaaaaa gaaaaaaatt    720 ggtggggtag ctttggatgt tatagaaaat gaatcaaata tatattataa tgatctaaaa    780
tgtcaggtac ttgataatag ggatttggca atacttaagt catatcctaa tgttattgtt    840
acacctcata cggcttttta tactgatcag gctgtaagtg atatggttga aaattctatt    900
ttaagttgta ttttattgt tgagaaaaaa gaaaatccat gggaagtttg ttaa           954

<210> SEQ ID NO 18
<211> LENGTH: 948
<212> TYPE: DNA
<213> ORGANISM: Clostridium tyrobutyricum

<400> SEQUENCE: 18
atgaaaatta gaggtataaa aatatccata attggtgctg gttttgtagg ttcgactact     60
gctttctcaa ttatgagttc tggcttggct tcagaaatag taatcgtaga tgtaaataaa    120
gataaggctg aaggagaagc aatggatcta gctcacggag tgtcatttgt aaaacctgtt    180
gatataaaat ctggcgatta caaggataca gaagaatcga atattgttat aataacagca    240
ggttccggtc aaaaacctgg tgaaagcaga ttggatttaa ttaatagaaa ttattctatc    300
```

```
tttaaatcca tagtacctga agttgtaaaa tacagccta aatctatact tttggtagtt      360
tcaaatcccg tggatatact gacttacata acctataaat tatctggatt tccacctgaa      420
agaataatag gttctggtac cgttctagac acctcaagac tcagatatat gataagtgaa      480
aatttcaata tagatgcaag aaatattcac agctatataa taggagaaca tggagattct      540
gaaatagcta catggagttc tacttctatt gccggaatac ctctagaaca atattgcaat      600
ttgatggatg ccagttgcga ttcggattat caggatagga taataaataa tgtaagaaat      660
gcagcttatg aggtaataga acgaaaggga tcaacttatt ttgctgttgc tctagccgtt      720
agacgaattg tagaagcact gtcaagagat gaaaattcaa taatgacagt ttctgcacta      780
tttagtggtg aatacgatgt agataatgtt tacatgggcc ttcctgcagt aataggatct      840
gaaggaattc aaaaaaccct ccgtgttcca ctaaacagtg tagaaaaaac agctttgcaa      900
acttcagctg atacactaaa agatataatt gaaaagttaa atatttaa                  948

<210> SEQ ID NO 19
<211> LENGTH: 1026
<212> TYPE: DNA
<213> ORGANISM: Clostridium tyrobutyricum

<400> SEQUENCE: 19
atgatacaat taaatatatg tatagctata cataaaaaag gaggcagcat tattatgaat       60
tctataaata ataaacttgt aatagttgga gtgggaaatg taggtactgc tgtattgaat      120
actgcattat ctttggatt tgcttcagaa attgcactaa ttgatataga taatgacaag      180
gcaagaggtg aagcattgga ctcaagtcat actacaccct gtacatatag tgtcaatgtg      240
gacatacatg agggaaacta tgaagattgc aaagatgcca atgttattat tatagctgca      300
ggtccaagta tattgaaaga tgataaaaat gatgatagaa cagttcttgc agaaagaaat      360
gtaaaagtaa tgaaagatgt aatgggttct ataagcaagt atacaaagga tgcaataata      420
attataataa caaatccatt ggacacaatg gtatattatg ctgaaaattt ctttggatat      480
cccaaagaaa aagtatttgg aacaggtaca agtcttgatt cagcccgttt tagaaagatc      540
atagcaaata gatacaatct tgaccctaag gatgttcatg ttatatgtt tggtgaacat      600 ggtaatactg catttccagt atggagccat ttgaatgttg agggagtttc agcagatgag      660
cttgataaat tttttcctca tgacaaacca ttggataagg aagaaatagc ttcagatgta      720
gtaaaggttg cctatgatgt acttcatttg aaagggtgta caattcggg cgttgctatg      780 gcggcctgca gaattgccag gcagtatttt atggatgaac atagtatatt gcctgtttcc      840
actactcttg aaggagaata tggattaaaa aatgtagcac tcagtttgcc atgtattata      900
ggaaaaaatg gagttgaaag aaggcttgaa gttcctctta ctgatgaaga aaatgacaaa      960
ctttataaca gtgcaaaaaa tatttttggct acaatgaaag ctgcaggatt aatagaagat     1020
aaataa                                                                1026

<210> SEQ ID NO 20
<211> LENGTH: 1377
<212> TYPE: DNA
<213> ORGANISM: Clostridium tyrobutyricum

<400> SEQUENCE: 20
atggattttg aaaaattatc tgatattata aagacgaaa ataggataaa gataggggaca        60 gatatagagg acaaatattt aagtgatgca ctaaatagga ataaaggtaa agctgatgta       120
```

```
ttgatatttc ctataaatac agaagaagta agcagcataa tgaaaatagc atatgaaaat      180
ggcatacctg ttacaccaag aggagccggt acaggattgg taggtgcaac tattcctacc      240
aggggaggta ttatattaga tctatcctta atgaaaaata tagttgagtt agatgaaaat      300
actcttacag taactgtgca gccgggaatt ttacttgtag atcttcaaaa atttgttgaa      360
agcaagggat ttttctatcc tccagatcca ggagaaaaaa atgcttcaat aggtggaaac      420
ataagtacta atgccggcgg aatgagagct gtaaagtatg gagttacaag agactatgtt      480
atggggttgg aagtagtttt agccgatgga accatactaa atacaggtgg aaaagtaata      540
aagaatagtt ctggacttga tataaaggac ttaataatag gatcagaagg tactcttgca      600
attataacca gggcaatatt aaaacttata ccaaaaccta aaagagtat aagcgctatt      660 attccattta actctttaaa agaaggaata gatacagtca taaaaataat aaaaaagaat      720
gccaatccta cagctattga atttatggaa agtgatgtca ttgaaaatgc agaaagattt      780
ttaaagttaa aatttccttc tgatagggga aaggcatatt tattattgac atttgatgga      840
gatgaagaat ttgaaataga gagtaattac aaaaaagtaa aagaagttgc tttgggaaat      900
aatgccctgg attttatttt gcttgataaa aaggatgaca tagagagaac ctggaaaata      960
agggagcctt tggttacggc agtagaagct gtatctgaac aggagcctat agatatagta     1020
gttccaatag acagatcagc agattttatt aattatacaa agtagcaga aaaggaattt      1080 ggaattaaga taagtagctt tggtcatgct ggcgatggaa atgtacactt atgtgtaatt     1140
agaaatggca tggaagaaaa tctatggaat gaaaaatcga gaaaactact taaagctctt     1200
tatagaaaag ggaagaaact taatggactg ccatctggag agcatggcat aggaattaac     1260
aagaaaccat attttattga tgtaacagat aagataaatg tagagtatat gagaagaata     1320
aaaaaagcct ttgatgaaaa gggaattta aattccggta atcatattc aatatga         1377

<210> SEQ ID NO 21
<211> LENGTH: 1593
<212> TYPE: DNA
<213> ORGANISM: Clostridium tyrobutyricum

<400> SEQUENCE: 21
atgaagtcaa aattaatgtc taaggacaag gcagttaaat taataaaaga tggagatact       60
gttgcagtag gtggctttgt tggatgtgca catccagagg atattacatc tgaaattgaa      120
gaaaattata ttgaaaatcg tactcctaaa atctaacat tgatttatgc tgcgggacaa       180
ggtgacagcg ctgatagagg actgaatcat tttggacatg aaggattagt cagtaaagta      240
ataggtggac attgggcatt aagtcctaaa cttcagaaat tagctcttga caataaaata      300
gaagcgtata atctgcccca gggaataata tcacaattgt atagagatat tgctgctaaa      360
aggccgggaa ccataaccca tgttggatta aagactttta tagatcctag acttgaaggt      420
ggaaagttaa atacaattac taagaaaaac atagtagaac ttataaatat aggaggaaaa      480
gaatatttat tttataaaac tataccattg gatgttgtaa ttttaagagc tacttatgct      540
gatgaatttg gaaatgctac tatggaaaaa gaagcggcaa tattagatgc aacagctatg      600
gctcaagctg caaagaactc aggaggtata gttatcgtac aagttgaaca agtagtatca      660
aaaggatctt agatcctaa aaagtaaag ataccggaa tatgtagaa tgctatagtt          720 gtatcacaac taaaaatca tatgcagact tttagtgaaa actataatcc atcatattct      780
ggagaagcaa gattttagt gaattccata gttcctatgc aacttaatga agaaaggtt        840 atagccagaa gagcggctat ggagcttgtt ccaaattctg taactaatct tggcattgga      900
```

```
ataccagaag gaatagcgac agttgccaat gaagaaggca ttgcagatga aatgacattg    960
actatagaat caggtggtat aggaggagta ccttcaggtg gactgagctt tggtgcttca   1020
actaatcctc aaagcatact tgatcaggca agtcaatttg actattacga tggaggaggt   1080
cttgatgtag catttttagg gcttgctcag tgtgacagag atggtaatat aaatgtaagc   1140
aaatttgggc ctaaaattgc aggttgtgga ggatttatta atataagtca aaattccaaa   1200
aaagttgtgt actgtggaac atttacagca ggtggtttaa aggtcaaagt ggaaaacgga   1260
aaacttaata tagaaaagga tggaaagttc aataaattta tagatactgt tgaacagata   1320
tctttcagtg gtcaatatgc tcagagtatt ggacaaacag tactttatat aactgaaaga   1380
gcagtattta gattgacaaa agaaggtctc tttttagagg aaatagctcc aggtatagat   1440
atgaaaaagg acatattgga tcatatggat tttaggccta aaatatctga aaatttaaag   1500
ataatggatg aaagaatatt taaagaagaa ccaataggaa taaatattgg acaatcatca   1560
aaagaattcc caggagaatt aagcaatgta taa                                1593
```

<210> SEQ ID NO 22
<211> LENGTH: 1450
<212> TYPE: DNA
<213> ORGANISM: Clostridium tyrobutyricum

<400> SEQUENCE: 22

```
atgggagtaa agtttttaaa ggcttgtgat gctgtagaaa tggttaaaga tggagacttg     60
atcgcaacaa gcggttttgt aggtagtctt tgttcagaag aacttagtat agctttagaa    120
aaacgttttg aagagacagg acatccaaaa aatttaacat tagtatattc tgcagctcaa    180
ggagatggaa agggaaaagg agcagatcat tttgcacatg aaggaatgtt aaaaagagtt    240
gcaggtggac attggaattt atcacctaaa ttgggcaaaa tggcagtaga aaataaaatt    300
gaagcatata atcttccaca aggaacaatt gcacaattat ttagagatat tgcaggaaaa    360
agaattggaa ccataactca tgttggatta aatacctttg tagatccaag aattcaaggt    420
ggaaagttaa atgatataac aaaagaagat gtagtaaaac ttataaatat tgagggtcag    480
gaaaaattac tttataaagc tttccctatt gatgtatgtt ttttgagagg atcttttgca    540
gatgaaaatg gtaatatatc acttgaaaga gaagtaggta ctatagatgt actttctata    600
gctcaagctt gtagaaatag cggtgggact gtaattgtac aagtcgaaaa ggtagtttct    660
tcaggtactt tggatccaag acttgtgaag ataccaggta tatatgttga tgtagtggtt    720
gttgccaaac ctgaacatca tgagcagttt tttggttgta atggttatga tccttcatta    780
actggtgaag tgagagttcc tttaaaagct atacaatatc ctgaattaaa tgcaagaaaa    840
ataatagcta gaagagctgc tatggaactc aaaccggatg cagtagtaaa tttaggtata    900
ggaatacctg aagttatatc aatggttgca aatgaagaag gaattggaga atatatgact    960
atgacagtag aagctggagc tgtaggagga gtgcctcttg gcggaactgg ttttggtgca   1020
tgcataaatc ctgaatcaat cttggacgag gcttatcaat ttgattttta tgatggcggt   1080
ggaactgata tagcattttt aggattggcc caagttgaca aaaacgggaa cataaatgta   1140
agtaaatttg gacctcgtat agctggatgc ggtggcttta taaatataac tcaaaatgct   1200
aaaagggtat tgttctgtgg tacatttaca gctggaggac taaaaataga cacaggcgat   1260
ggaaaattaa acataattca agaaggaaga gcaataaaat ttttaaaaca agttgaacag   1320
ataaccttca gtggagaata tgctattaaa acaaagcagc cagttactta tataactgaa   1380
```

-continued agggcagtat ttgaacttaa agaagatgga ctatatatta cagagatagc tccaggtgtt 1440
gatattgaaa 1450

<210> SEQ ID NO 23
<211> LENGTH: 1182
<212> TYPE: DNA
<213> ORGANISM: Clostridium tyrobutyricum

<400> SEQUENCE: 23
atgagtgaag ttgtaattgc aagtgccgtt agaacagcaa taggtaaatt tggaggtagc 60
ttgaagtcag ttccagcaac tgatttagga gctttggtta taaaagaagc attaaaaaga 120
gctaatgtta aaccagaact tgtagatgaa gttgtaatgg gtaatgtatt acaggcaggt 180
ttaggtcaga atccagcaag acaagcattg ataaaatcag gtatacctaa tacagtccct 240
ggatttacta taaataaagt ttgtggttca ggacttagag cagtaagttt agcagctcaa 300
atgataaaag ctggcgatga tgatatcgtt gtagctggtg gaatggaaaa tatgtctgct 360
gctccatatg taatgcctag tgcaagatgg ggacaaagaa tgtttgatgg taagattata 420
gatgaaatgg taaaagacgg actttgggat gcttttaata actatcacat gggtattacg 480
gctgaaaata tagcagaaaa gtggaacata acaagacaaa tgcaggatga atttgcagct 540
gcatcacaac aaaaagcagt agcagctata aaatctggca agtttaaaga tgaaatagtt 600
ccagtagtaa tcaaggatag aaaaaaggga gaaatagtat ttgatactga tgaattccct 660
agagatggtg taactgtcga aggaatatca aaattaaaac cagcatttaa gaaggatggt 720
ggaactgtta cagctgccaa tgcttcaggt ataaatgatg cagctgcagc attagttata 780
atgagtgcag acaaagcaaa agaattggga attaaaccac ttgctaaaat tacttcttat 840
ggatcaaaag gcttggatcc tagcataatg ggatatggac cattccatgc tacaaaacta 900
gcacttaaaa aagctaattt aactgtagat gatttagatt taatagaagc aaacgaagca 960
tttgctgctc agagtttagc tgttgcaaaa gacttgaaat ttgatatgag caaagtaaat 1020
gtaaatggag gagcaatagc acttggacat cctattggag cttcaggcgc aagaatactt 1080
actactttgc tttatgaaat gcagaaaaga gattcaaaac gtggtttagc tacattatgt 1140
ataggcggtg gaatgggaac tgctataatc gttgaaagat aa 1182

<210> SEQ ID NO 24
<211> LENGTH: 936
<212> TYPE: DNA
<213> ORGANISM: Clostridium tyrobutyricum

<400> SEQUENCE: 24
atgaatataa aaagtatatc agttttaggt actggaacta tgggacatgg catagcatta 60
ttttcgtcaa tggctggttt aaatgtaact atgtacggta ggtcagatgc aagtcttaaa 120
agaggattta gtgctataaa agaggactta ggacgattag aatcacaagg agaattagat 180
gatggtactt gtaaaagtat attagataga ataaaagggg tcaaaactat tgaagaagcc 240
tctaaaggaa cagattttgt aatagagtct ttagccgaag acttgcagat caaaagaaaa 300
ttttttgaaa agttggatgc tctttgtaaa tacgatgtta ttcttgctac aaacacttca 360
ggacttagtc ctacaaaaat aggggaagtt acaaaacatc cagagagagt agtggtagct 420
cacttttgga acccacctca attaattcca ttagtagaaa tagtacctgg ggaaaaaact 480
tctaaggata ctgtattaaa gacaaaggaa ttaattgaat ttatagggaa gaaagctgtt 540
tgtatggaaa aagagtgtgc tggttttata ggaaatagat tacagcttgc acttctaaga 600

```
gaggctatgt atatagtaga gcaaggatgg gcaaaaccag aagaagtaga caaggctatg      660
gaatatggac atggtcgaag acttccagtt acaggaccat taagcagtgc agatctaggg      720
ggactggata tattttacaa tatatcatct tatttattta agatctgtg tgattataaa       780 aagccatttg aattaatgaa agaaaagatt gaaaaaggtg attttaggaag taaaagtgga    840 aaaggatttt ataattggtc taaaggggat ttagaaaaaa aacaaaaaga acgaacagac     900
ctacttttat atttcttaaa aaaggatgcc aattaa                               936
```

```
<210> SEQ ID NO 25
<211> LENGTH: 849
<212> TYPE: DNA
<213> ORGANISM: Clostridium tyrobutyricum

<400> SEQUENCE: 25
atgaaaaaaa tatgtgttct tggtgcaggt acaatgggtt ctggaatagc tcaggctttt      60
gcagctaaag gttgtgaagt attaataaga gatattaaag atgaattcgt tgatagagga     120
cttgcaggaa ttaaaaaagg atttgacaag agaatagcaa agggtaaaat ggtacaggca     180
gatgctgatg caatacttgc tagaataagt ggaacagttg acctagaaaa ggcagctgat     240
tgcgatctag taatagaagc agcagttgaa aatatggaga taaagaagca aatatttggt     300
gacttggata aaatatgtaa gcctgaaaca attttagctt ctaatacttc ttcattgtca     360
ataactgaaa tagcatctgc tacaaaaaga caggataaag ttataggaat gcatttctttt    420 aatccagcac ctgtaatgaa attagttgag ataataagag gaatggctac ttcacaagaa     480
acttttgatg cagtaaaaga gtttcaattt gccataggca aggatccagt agaggtggca     540
gaagctccag gattttgttgt aaatagaata ttaatacca tgataaatga agccgtagga     600
atttttgcgg aaggaatagc ttcagcagag gatattgata aagctatgaa acttggtgct     660
aatcatccaa tgggaccact agcattagga gatcttattg gactggatgt atgtcttgca     720
attatggatg tactttataa agaaacaggg gattccaaat acagagctca ctcgctactt     780
agaaaatatg taagagcagg atggcttgga agaaagagca aaaaaggatt ctttgattat     840
tcaaaataa                                                              849
```

```
<210> SEQ ID NO 26
<211> LENGTH: 777
<212> TYPE: DNA
<213> ORGANISM: Clostridium tyrobutyricum

<400> SEQUENCE: 26
atggaaaatg ttatttttaaa agaagagaat ggtattgcag aagttattat taatagacct      60
aaagcactta atgcgttgaa tagtgaaaca ctaaaagaac ttggaaacgt aatcgatggc     120
ataaatgtaa acgataatat taaggcggta atattaacag gttcaggtga aaaatcattt     180
gtagcaggag ctgacatagc acaaatgagt aaactgaatt caatagaagc aacaaaattc     240
tcaagacttg cacaaaatgt gttttcacaa atagaagatc ttcctaaatt agtaatagct     300
gcagtcaatg gatttgctct tggaggaggt tgtgaacttg ccatggcatg tgatataaga     360
tttgcttcga agaaagctaa atttggacaa ccagaagtta atttaggtat actgccaagt     420
tttggaggca cacaaagact tccaagatta gttggaaaag gaatagcaaa agaattaatt     480
ttttctgcag atatgattag tgctgatgaa gcttatcgta taggacttgt caataaagtt     540
tatgaacctg atgagctact ttcaaagtca aaagaatttg cacaaaaggt aatgactaaa     600
```

```
tctccatggg gtgttaaatt ggcaaaagca tcaataaata atggattgga tgttgacttg    660
gaagctggac ttaaatatga agcaaattct tttggattat gtttctcaac tgaagatcaa    720
aaagagggta tgaaagcctt tttggaaaag agaaaagcta atttaaaga ttgttaa       777
```

```
<210> SEQ ID NO 27
<211> LENGTH: 780
<212> TYPE: DNA
<213> ORGANISM: Clostridium tyrobutyricum

<400> SEQUENCE: 27
atgagtttta aaaatgttaa ttttgagaaa gatggaaaga tggttgtaat tacaattaat     60
agacctaagg cacttaatgc acttaactcg gaaacattag ttgaaattga ttcggcaatc    120
gatatggtag ctgaagatga agatgtttta gctgtaatac ttacaggtgc tggaaagtct    180
tttgtagctg gtgcagatat atcagaaatg aaaggtctca atgctattga aggaagaaaa    240
tttggaatat tgggcaacaa ggttttagaa agttggaaa aattggaaaa gcctgttatt    300
gcagcagtta atggttttgc attaggcggt ggttgtgaaa tttccatggc atgtgatata    360
agaatagctt catcaaaagc taaattcgga caaccagagt caggacttgg tattacccca    420
ggttttgggg gaactcaaag acttccaaga ttagtaggac ttggaatggc aaaagaactt    480
atatacactg ccaaaattat aaaagcggat gaagcattta aataggact tgtaaataaa    540 gtagtagaac ctgaagcact tatggatgaa gctaaagcat tagctaatac aataattaac    600
aatgcaccaa tagctgtaaa gttatgtaaa gaggcaataa atagaggaat acagacagat    660
atagatactg gagcagcata cgaatctgaa gtatttgggg aatgctttgc tacagaggat    720
caaaaagaag gtatgggtgc gtttctcgaa aaaagagata aactttttaa aaataaataa    780
```

```
<210> SEQ ID NO 28
<211> LENGTH: 1098
<212> TYPE: DNA
<213> ORGANISM: Clostridium tyrobutyricum

<400> SEQUENCE: 28
atggtaaggg aatttacaga aaatgaagtt aaacctctag cggcagagat agatgagact     60
gagagattcc ctaaagaaac tgtagaaaaa atggctaaat atggaatgat gggtatacct    120
ttcccagtaa aatatggtgg agcaggtgga gacactctat cctatatatt agcagtagaa    180 gaacttttcca aggcttgtgg aacaacgggt gttatacttt cagctcatac atcactttgt    240
gcatcacttc ttgaacagtt tggaacggaa gagcaaaaac aaaatatct ggtaccactt    300 gcaaagggag aaaaacttgg agcatttgga ttaactgaac ctaatgctgg tactgatgct    360
tcaggacaac aaagcttggc tgtactagaa ggagatcatt atatattaaa tggtcaaaaa    420
atatttataa caaatggtgg agcagcagat atatttgtag tatttgcaat gactgataga    480
agcaagggta caagaggaat atcagcattt tacttgaaa agggtatgaa aggttttcg    540 attggaaagc ttgaaaataa aatgggtata agagcgtcat caactactga acttatattt    600
gaagattgta tagttccaaa agagaatttg gtaggaagag aaggaaaagg ctttggtata    660
gcaatgaaaa ctcttgatgg aggaagaatt ggtatagcag cccaggctct aggtatagca    720
gaaggagctt tggaggaagc cgttgaatat atgaaagaaa gaaaacaatt ggaagatca    780 ctttccaaat tccagggatt aggctgggtc gttgctgatc ttgcaaccaa aatagatgcg    840
gcaagatatc ttgtttacaa agcggcatta aataaagatg cacatgtccc ttatacagta    900
gatgcggcaa aggctaaatt aatggcagca gatgttgcta tggaaactac aactaaggtt    960
```

```
gttcaattgt ttggtggata tggatatacc aaggattatc cagtagagag aatgatgaga    1020
gatgcaaaga taactgagat atatgaggga acttctgagg tacaaagaat ggttatttcc    1080
ggaagcatat ttagatag                                                  1098

<210> SEQ ID NO 29
<211> LENGTH: 444
<212> TYPE: DNA
<213> ORGANISM: Clostridium tyrobutyricum

<400> SEQUENCE: 29
atgaataaaa aaatcaaatg gttgcttgta tttttatgga tgattttaat attttccttt     60
tcaagtcaat caggagttgc atctgatgaa aaaagtagat ttattgtata tctatttaat    120
gagtcaggaa taaatcttaa tagtgtattt ggaaatctag caaattttgc agtaaggaaa    180
ttttctcatt tcacagagta ttttatatta tatatattgt tgtttaacgc actatatgag    240
aaatctaaaa tgaagaagac tttttttattg tcaatagtaa tagtatttt atatgcatgt    300 tctgatgaaa tacatcagtt ttttgttcca ggcagatctt caagaataag ggatgttata    360
atagatactt ccggaggttt tgcatcactt ttatgttgtt tgtttcacag tcgtagaaag    420
aataaatata ggagagattt atag                                           444

<210> SEQ ID NO 30
<211> LENGTH: 1164
<212> TYPE: DNA
<213> ORGANISM: Clostridium tyrobutyricum

<400> SEQUENCE: 30
ttgattaact ttaattattc aattccaaca gagattttct ttggaaaggg cagcataagt     60
attctaggaa acaattaaa aagatatggc gctaaagtac ttgttgtata tggtggagga    120
agtataaaga aaaatggaat atatgattg gcaattaaac ttataaagga agtaaaata    180 aaattttggg aattgtcagg tgtagagccc aatcctaaaa tatccagtgt aagacaaggt    240
gtaaaaatat gcagggacaa caggatagat tgtatactgg caataggagg aggcagtgta    300
attgactgtt ctaaagctat agcggcaggc tattattatg gaggagatcc atgggatatt    360
gtaacagacc cttcaaaaat aaagaaagca cttcctgttg cgagtatttt aacattagca    420
gctacaggat cggaaatgga catatttgct gttattacaa atgaagaaac caaggaaaag    480
ttaggtacaa aaagctcata tatggctcca aggttttcca tacttgatcc cacttatact    540
tttacagtat caaaaaaatca gacagcagca ggaacagcag atataatgag tcatatttatg    600 gaaaactatt ttaataatac agaaggtgcc tatgttcagg acagattagc agaggcactc    660
ttaaagacat gtataaaata tggccctata gctcttgaaa aacctgatga ttatgatgca    720
agagccaatt taatgtggac ttcaagtctt gcgataaatg gacttctgga ttatggcaag    780
gtaaaaggtt ggagtgtcca tggcatgaa catgaattaa gtgcatttta tgatattacc    840
catggtgtgg gattggctat attaacaccc tattggatgg aatatgtatt agataataat    900
acagtagaca aatttgtgga atatggaata aatatatggt ctatagataa aaataaagat    960
aaatttacga tagcacatga gtcaatagag aaaacacgcg aattctttaa ttcattggga    1020
cttcctgcca gacttaaaga agtaggcatt gatgaagaga ttttgaaaa aatggctgaa    1080 ggagctacaa gacatggaaa actgggagaa ttcaagccgc tttcaaaaca agatgtcata    1140
aatatatata agtcagcatt ataa                                          1164
```

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gcggcgtgcy taayacatgc                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gggttgcgct cgttgcrgga                                              20

<210> SEQ ID NO 33
<211> LENGTH: 272
<212> TYPE: DNA
<213> ORGANISM: Clostridium tyrobutyricum

<400> SEQUENCE: 33
atggcgaaca atgcattaag aaatatgaac gtcaattcaa ataatgcatc aaaggcaatg    60
gaaaaacttt cttcaggtct tagaataaac agagctggag acgatgcagc aggactagca   120
atatcagaaa aaatgagagg acagataaat ggtttgaatc aggcatcaag taatgcacag   180
gattcaatat cacttataca gactgctgaa ggtgcattaa acgaaactca cagcatactt   240
cagagaatga gaacacttgc tgttcaatca tc                                272

<210> SEQ ID NO 34
<211> LENGTH: 272
<212> TYPE: DNA
<213> ORGANISM: Clostridium tyrobutyricum

<400> SEQUENCE: 34
atggcaaaca atgcattaag aaatatgaac atcaattcag gaaatgcatc aaaggcaatg    60
gaaaaacttt cttcaggtct tagaataaac agagctggag atgacgcagc aggattagca   120
atatcagaaa aaatgagagg acagataaat ggattaaacc aggcatcaag caactcacag   180
gatgctatat cccttataca gactggtgaa ggtgcattaa atgaaactca cagtatactt   240
cagagaatga gaacacttgc agttcaatca tc                                272

<210> SEQ ID NO 35
<211> LENGTH: 162
<212> TYPE: DNA
<213> ORGANISM: Clostridium tyrobutyricum

<400> SEQUENCE: 35
aatagattgg aacatacaat aaataactta ggaacttcat cagaaaactt gacttctgct    60
gaatcaagaa taagagatgt tgatatggca tcagaaatgt ctgagtactc aaagaataac   120
attctttctc agactgctca ggcaatgctt gcacaagcaa at                      162

<210> SEQ ID NO 36
<211> LENGTH: 162

```
<212> TYPE: DNA
<213> ORGANISM: Clostridium tyrobutyricum

<400> SEQUENCE: 36
aatagattgg aacatactat aaacaatctt ggaacttcat cagaaaattt gacttctgct        60
gaatcaagaa tcagagatgt ggatatggca tcagagatgt ctgagtactc aaagaacaat       120
attctttctc aggctgctca ggcaatgctg gctcaagcaa at                         162
```